US010653710B2

(12) United States Patent
Agresta et al.

(10) Patent No.: US 10,653,710 B2
(45) Date of Patent: May 19, 2020

(54) COMBINATION THERAPY FOR TREATING MALIGNANCIES

(71) Applicants: Agios Pharmaceuticals, Inc., Cambridge, MA (US); Celgene Corporation, Summit, NJ (US)

(72) Inventors: Samuel V. Agresta, Lexington, MA (US); Krishnan Viswanadhan, East Hanover, NJ (US); Jorge DiMartino, Belmont, CA (US); Vivek Saroj Kumar Chopra, South San Francisco, CA (US); Kyle J. MacBeth, San Francisco, CA (US); Robert Douglas Knight, Berkeley Heights, NJ (US); Laurie Kenvin, New Hope, PA (US); Qiang Xu, Bernards, NJ (US)

(73) Assignees: Agios Pharmaceuticals, Inc., Cambridge, MA (US); Celgene Corporation, Summit, NJ (US)

( * ) Notice: Subject to any disclaimer, the term of this patent is extended or adjusted under 35 U.S.C. 154(b) by 4 days.

(21) Appl. No.: 15/767,822

(22) PCT Filed: Oct. 14, 2016

(86) PCT No.: PCT/US2016/057042
§ 371 (c)(1),
(2) Date: Apr. 12, 2018

(87) PCT Pub. No.: WO2017/066571
PCT Pub. Date: Apr. 20, 2017

(65) Prior Publication Data
US 2018/0296583 A1 Oct. 18, 2018

Related U.S. Application Data

(60) Provisional application No. 62/242,282, filed on Oct. 15, 2015.

(51) Int. Cl.
| A61K 31/706 | (2006.01) |
| A61K 31/444 | (2006.01) |
| A61K 45/06 | (2006.01) |
| A61K 35/02 | (2015.01) |
| A61P 35/02 | (2006.01) |

(52) U.S. Cl.
CPC .......... *A61K 31/706* (2013.01); *A61K 31/444* (2013.01); *A61K 45/06* (2013.01); *A61P 35/02* (2018.01)

(58) Field of Classification Search
CPC .... A61K 45/06; A61K 31/444; A61K 31/706; A61K 2300/00; A61P 35/02
See application file for complete search history.

(56) References Cited

U.S. PATENT DOCUMENTS

| 2,390,529 | A | 12/1945 | Friedheim |
| 3,755,322 | A | 8/1973 | Winter et al. |
| 3,867,383 | A | 2/1975 | Winter |
| 4,084,053 | A | 4/1978 | Desai et al. |
| 5,021,421 | A | 6/1991 | Hino et al. |
| 5,489,591 | A | 2/1996 | Kobayashi et al. |
| 5,807,876 | A | 9/1998 | Armistead et al. |
| 5,834,485 | A | 11/1998 | Dyke et al. |
| 5,965,559 | A | 10/1999 | Faull et al. |
| 5,965,569 | A | 10/1999 | Camps Garcia et al. |
| 5,984,882 | A | 11/1999 | Rosenschein et al. |
| 6,262,113 | B1 | 7/2001 | Widdowson et al. |
| 6,274,620 | B1 | 8/2001 | Labrecque et al. |
| 6,313,127 | B1 | 11/2001 | Waterson et al. |
| 6,399,358 | B1 | 6/2002 | Williams et al. |
| 6,576,235 | B1 | 6/2003 | Williams et al. |
| 6,723,730 | B2 | 4/2004 | Bakthavatchalam et al. |
| 6,783,965 | B1 | 8/2004 | Sherman et al. |
| 6,979,675 | B2 | 12/2005 | Tidmarsh |
| 7,173,025 | B1 | 2/2007 | Stocker et al. |
| 7,858,782 | B2 | 12/2010 | Tao et al. |
| 8,133,900 | B2 | 3/2012 | Hood et al. |
| 8,257,741 | B2 | 9/2012 | Curatolo et al. |
| 8,263,128 | B2 | 9/2012 | Curatolo et al. |
| 8,337,899 | B2 | 12/2012 | Curatolo et al. |
| 8,367,118 | B2 | 2/2013 | Curatolo et al. |
| 8,431,159 | B2 | 4/2013 | Curatolo et al. |
| 8,465,673 | B2 | 6/2013 | Yasuda et al. |
| 9,474,779 | B2 * | 10/2016 | Lemieux .............. C07D 205/08 |
| 9,850,277 | B2 * | 12/2017 | Popovici-Muller .......................... C07D 205/08 |

(Continued)

FOREIGN PATENT DOCUMENTS

| CN | 101296909 A | 10/2008 |
| CN | 101575408 A | 11/2009 |

(Continued)

OTHER PUBLICATIONS

"Study of orally adminisered AG-120 in subjects with advanced hematologic malignancies with an IDH1 mutation," clinicaltrials.gov retreived Feb. 6, 2017.

(Continued)

*Primary Examiner* — Lawrence E Crane
(74) *Attorney, Agent, or Firm* — Goodwin Procter LLP

(57) ABSTRACT

Provided are methods and compositions for treating hematological malignancies in patients carrying an IDH1 mutation using a combination of an inhibitor of mutant IDH1 enzyme, (S)-N-((S)-1-(2-chlorophenyl)-2-((3,3-difluorocyclobutyl)amino)-2-oxoethyl)-1-(4-cyanopyridin-2-yl)-N-(5-fluoropyridin-3-yl)-5-oxopyrrolidine-2-carboxamide, or a pharmaceutically acceptable salt thereof (COMPOUND 2) and a DNA demethylating agent.

20 Claims, 10 Drawing Sheets

(56) References Cited

U.S. PATENT DOCUMENTS

| | | | |
|---|---|---|---|
| 9,968,595 | B2 | 5/2018 | Gu |
| 10,111,882 | B2 * | 10/2018 | Abella ............... A61K 31/5377 |
| 10,449,184 | B2 | 10/2019 | Gu |
| 2002/0049310 | A1 | 4/2002 | Tateishi et al. |
| 2002/0188027 | A1 | 12/2002 | Robinson et al. |
| 2003/0095958 | A1 | 5/2003 | Bhisetti et al. |
| 2003/0109527 | A1 | 6/2003 | Jin et al. |
| 2003/0207882 | A1 | 11/2003 | Stocker et al. |
| 2003/0213405 | A1 | 11/2003 | Harada et al. |
| 2004/0067234 | A1 | 4/2004 | Einat et al. |
| 2004/0248221 | A1 | 12/2004 | Stockwell |
| 2005/0261268 | A1 | 11/2005 | Arnost et al. |
| 2006/0084645 | A1 | 4/2006 | Pal et al. |
| 2006/0281122 | A1 | 12/2006 | Bryant et al. |
| 2007/0244088 | A1 | 10/2007 | Brickmann et al. |
| 2008/0132490 | A1 | 6/2008 | Bergman et al. |
| 2008/0300208 | A1 | 12/2008 | Einat et al. |
| 2009/0093526 | A1 | 4/2009 | Miller et al. |
| 2009/0163508 | A1 | 6/2009 | Kori et al. |
| 2009/0163545 | A1 | 6/2009 | Goldfarb |
| 2009/0281089 | A1 | 11/2009 | Gunzner et al. |
| 2009/0286752 | A1 | 11/2009 | Etter et al. |
| 2010/0129350 | A1 | 5/2010 | Zacharie et al. |
| 2010/0144722 | A1 | 6/2010 | Alexander et al. |
| 2010/0273808 | A1 | 10/2010 | Armitage et al. |
| 2010/0331307 | A1 | 12/2010 | Salituro et al. |
| 2011/0073007 | A1 | 3/2011 | Yasuda et al. |
| 2011/0086088 | A1 | 4/2011 | Berry |
| 2011/0288065 | A1 | 11/2011 | Fujihara et al. |
| 2012/0121515 | A1 | 5/2012 | Dang et al. |
| 2012/0129865 | A1 | 5/2012 | Wang et al. |
| 2012/0164143 | A1 | 6/2012 | Teeling et al. |
| 2012/0202818 | A1 | 8/2012 | Tao et al. |
| 2012/0238576 | A1 | 9/2012 | Tao et al. |
| 2012/0277233 | A1 | 11/2012 | Tao et al. |
| 2013/0035329 | A1 | 2/2013 | Saunders et al. |
| 2013/0109643 | A1 | 5/2013 | Riggins et al. |
| 2013/0183281 | A1 | 7/2013 | Su et al. |
| 2013/0184222 | A1 | 7/2013 | Popovici-Muller et al. |
| 2013/0190249 | A1 | 7/2013 | Lemieux et al. |
| 2013/0190287 | A1 | 7/2013 | Cianchetta et al. |
| 2013/0197106 | A1 | 8/2013 | Fantin et al. |
| 2014/0094503 | A1 | 4/2014 | Ma et al. |
| 2014/0187435 | A1 | 7/2014 | Dang et al. |
| 2014/0206673 | A1 | 7/2014 | Cao et al. |
| 2014/0213580 | A1 | 7/2014 | Cao et al. |
| 2015/0018328 | A1 | 1/2015 | Konteatis et al. |
| 2015/0031627 | A1 | 1/2015 | Lemieux et al. |
| 2015/0031641 | A1 | 1/2015 | Levine et al. |
| 2015/0044716 | A1 | 2/2015 | Balss et al. |
| 2015/0087600 | A1 | 3/2015 | Popovici-Muller et al. |
| 2015/0240286 | A1 | 8/2015 | Dang et al. |
| 2015/0299115 | A1 | 10/2015 | Popovici-Muller et al. |
| 2016/0130298 | A1 | 5/2016 | Lemieux et al. |
| 2016/0264621 | A1 | 9/2016 | Popovici-Muller et al. |
| 2016/0304556 | A1 | 10/2016 | Popovici-Muller et al. |
| 2017/0007661 | A1 | 1/2017 | Gu |
| 2017/0014396 | A1 | 1/2017 | Gu |
| 2017/0015703 | A1 | 1/2017 | Popovici-Muller et al. |
| 2017/0057994 | A1 | 3/2017 | Lemieux et al. |
| 2018/0296583 | A1 * | 10/2018 | Agresta ................. A61K 45/06 |
| 2018/0303808 | A1 | 10/2018 | Agresta |
| 2018/0303840 | A1 * | 10/2018 | Chopra ................. A61K 31/53 |
| 2018/0325880 | A1 | 11/2018 | Gu |
| 2019/0046512 | A1 | 2/2019 | Amatangelo et al. |

FOREIGN PATENT DOCUMENTS

| | | |
|---|---|---|
| CN | 102659765 A | 9/2012 |
| CN | 103097340 A | 5/2013 |
| DE | 2263878 A1 | 7/1973 |
| DE | 3314663 A1 | 10/1983 |
| DE | 3512630 A1 | 10/1986 |
| EP | 0022958 A1 | 1/1981 |
| EP | 0384228 A1 | 8/1990 |
| EP | 0385237 A2 | 9/1990 |
| EP | 901786 A2 | 3/1999 |
| EP | 0945446 A1 | 9/1999 |
| EP | 1391487 A2 | 2/2004 |
| EP | 1886673 A2 | 2/2008 |
| FR | 2735127 A1 | 12/1996 |
| GB | 1033266 A | 6/1966 |
| JP | H04099768 A | 3/1992 |
| JP | H05140126 A | 6/1993 |
| JP | H09291034 A | 11/1997 |
| JP | H11158073 A | 6/1999 |
| JP | 2004107220 A | 4/2004 |
| JP | 2005264016 A | 9/2005 |
| JP | 2009237115 A | 10/2009 |
| JP | 2010079130 A | 4/2010 |
| JP | 2010181540 A | 8/2010 |
| JP | 4753336 B2 | 8/2011 |
| JP | 2013519858 A | 5/2013 |
| MX | 2013/000614 A | 6/2013 |
| TW | 201028381 A | 8/2010 |
| WO | 1996030343 A1 | 10/1996 |
| WO | 9728128 A1 | 8/1997 |
| WO | 9728129 A1 | 8/1997 |
| WO | 1997044322 A1 | 11/1997 |
| WO | 9932463 A1 | 7/1999 |
| WO | 00002864 A1 | 1/2000 |
| WO | 2001016097 A1 | 3/2001 |
| WO | 2001019788 A2 | 3/2001 |
| WO | 2001019798 A2 | 3/2001 |
| WO | 0147897 A1 | 7/2001 |
| WO | 2001064642 A2 | 9/2001 |
| WO | 2001064643 A2 | 9/2001 |
| WO | 2002100822 A1 | 12/2002 |
| WO | 2002102313 A2 | 12/2002 |
| WO | 030016289 A1 | 2/2003 |
| WO | 2004009562 A1 | 1/2004 |
| WO | 2004046120 A2 | 6/2004 |
| WO | 2004050033 A2 | 6/2004 |
| WO | 2004073619 A2 | 9/2004 |
| WO | 2004074438 A2 | 9/2004 |
| WO | 2004089470 A2 | 10/2004 |
| WO | 2005035507 A2 | 4/2005 |
| WO | 2005060956 A1 | 7/2005 |
| WO | 2005065691 A1 | 7/2005 |
| WO | 2005103015 A1 | 11/2005 |
| WO | 2005120474 A2 | 12/2005 |
| WO | 2006034341 A2 | 3/2006 |
| WO | 2006038594 A1 | 4/2006 |
| WO | 2006070198 A1 | 7/2006 |
| WO | 2006079791 A1 | 8/2006 |
| WO | 2006/110761 A2 | 10/2006 |
| WO | 2007003934 A2 | 1/2007 |
| WO | 2007023186 A1 | 3/2007 |
| WO | 2008036835 A2 | 3/2008 |
| WO | 2008050168 A1 | 5/2008 |
| WO | 2008050186 A1 | 5/2008 |
| WO | 2008052190 A2 | 5/2008 |
| WO | 2008070661 A1 | 6/2008 |
| WO | 2008073670 A2 | 6/2008 |
| WO | 2008076883 A2 | 6/2008 |
| WO | 2008131547 A1 | 11/2008 |
| WO | 2008154026 A1 | 12/2008 |
| WO | 2009013126 A1 | 1/2009 |
| WO | 2009015254 A1 | 1/2009 |
| WO | 2009016410 A2 | 2/2009 |
| WO | 2009118567 A2 | 10/2009 |
| WO | 2009126863 A2 | 10/2009 |
| WO | 2009150248 A1 | 12/2009 |
| WO | 2010007756 A1 | 1/2010 |
| WO | 2010028099 A1 | 3/2010 |
| WO | 2010105243 A1 | 9/2010 |
| WO | 2010129596 A1 | 11/2010 |
| WO | 2010130638 A1 | 11/2010 |
| WO | 2010144338 A1 | 12/2010 |
| WO | 2010144404 A1 | 12/2010 |
| WO | 201105210 A1 | 1/2011 |
| WO | 2011002817 A1 | 1/2011 |
| WO | 2011/027249 A2 | 3/2011 |
| WO | 2011032169 A2 | 3/2011 |

(56) References Cited

FOREIGN PATENT DOCUMENTS

| | | | |
|---|---|---|---|
| WO | 2011047432 | A1 | 4/2011 |
| WO | 2011050210 | A1 | 4/2011 |
| WO | 2011072174 | A1 | 6/2011 |
| WO | 2012006506 | A1 | 1/2012 |
| WO | 2012009678 | A1 | 1/2012 |
| WO | 2012074999 | A1 | 6/2012 |
| WO | 2012078288 | A2 | 6/2012 |
| WO | 2012092442 | A1 | 7/2012 |
| WO | 2012151452 | A1 | 11/2012 |
| WO | 2012160034 | A1 | 11/2012 |
| WO | 2012171337 | A1 | 12/2012 |
| WO | 2012171506 | A1 | 12/2012 |
| WO | 2012173682 | A2 | 12/2012 |
| WO | 2013004332 | A1 | 1/2013 |
| WO | 2013007708 | A1 | 1/2013 |
| WO | 2013016206 | A1 | 1/2013 |
| WO | 2013102431 | A1 | 7/2013 |
| WO | 2013107291 | A1 | 7/2013 |
| WO | 2013107405 | A1 | 7/2013 |
| WO | 2013133367 | A1 | 9/2013 |
| WO | 2014015422 | A1 | 1/2014 |
| WO | 2015/003360 | A2 | 1/2015 |
| WO | 2015127172 | A1 | 8/2015 |
| WO | 2015127173 | A1 | 8/2015 |
| WO | 2015138837 | A1 | 9/2015 |
| WO | 2015138839 | A1 | 9/2015 |
| WO | 2017066566 | A1 | 4/2017 |
| WO | 2017066571 | A1 | 4/2017 |
| WO | 2017096309 | A1 | 6/2017 |
| WO | 2017146795 | A1 | 8/2017 |

OTHER PUBLICATIONS

Birendra et al. "Evidence for clinical differentiation and differentiation syndrome in patients with acute myeloid leukemia and IDH1 mutations treated with the targeted mutant IDH1 inhibitor, AG-120," Clinical Lymphoma, Myeloma & Leukemia, 2016, 16(8):460-5.

Caunt et al. "MEK1 and MEK2 inhibitors and cancer therapy: the long and winding road," Nature Reviews Cancer, 2015, 15(10):577-592.

Dinardo et al. "Characteristics, clinical outcome, and prognostic significance of IDH mutations in AML," American Journal of Hematology, 2015, 90(8):732-736.

Dinardo et al. "Molecular profiling and relationship with clinical response in patients with IDH1 mutation-positive hematologic malignancies receiving AG-120, a first-in-class potent inhibitor of mutant IDH1, in addition to data from the completed dose escalation portion of the phase 1 study," Blood, 2015, 126:1306.

Green et al. "The prognostic significance of IDH1 mutations in younger adult patients with acute myeloid leukemia is dependent on FLT3/ITD status," Blood, 2010, 116(15):2779-2782.

Hansen et al. "AG-120, an oral, selective, first-in-class, potent inhibitor of mutant IDH1, reduces intracellular 2HG and induces cellular differentiation in TF-1 R132H cells and primary human IDH1 mutant AML patent samples treated ex vivo," Blood, 124(21):3734.

Hemerly et al. "Identification of several novel non-p.R132 IDH1 variants in thyroid carcinomas," European Journal of Endocrinology, 2010, 163(5):747-755.

Wei Chao et al. Teaching Materials of the 12th Five-Year Paln for the Relevant Majors of Pharmacy in the Specialty and Polytechnic Colleges, Pharmacy (2nd edition), Henan Science and Technology Press, 2012.

Yuan et al. "Role of IDH1 gene mutation in the genesis of glioblastoma," Medical Journal of Wuhan University, 2011, 32(2):164-166.

Kumar et al. "Pharmaceutical solid dispersion technology: A strategy to improve dissolution of poorly water-soluable drugs," Recent Patents on Drug Delivery and Formulation, 2013, 7:111-121.

Kumar et al., "4-Anilinoquinoline triazines: A novel class of hybrid antimalarial agents" European Journal of Medicinal Chemistry (2011) vol. 46, pp. 676-690.

Kumar et al., "Synthesis and bioevaluation of hybrid 4-aminoquinoline triazines as a new class of antimalarial agents," Bioorganic & Medicinal chemistry Letters (2008) vol. 18, pp. 6530-6533.

Lee et al. "Combinatorial Solid-Phase Synthesis of 6-Aryl-1,3,4-triazines via Suzuki Coupling" Aust. J. Chem. (2011) vol. 64, pp. 540-544.

Liu et al. "Inhibition of Cancer-Associated Mutant Isocitrate Dehydrogenases: Synthesis, Structure—Activity Relationship, and Selective Antitumor Activity" Journal of Medicinal Chemistry (2014) vol. 57, pp. 8307-8318.

Lou. "IDH1: function follows form." SciBX, 2009, 1-2.

Lowe, "Good old medicinal chemistry: what can you get away with?," Blog "In the Pipeline," entry of Nov. 2, 2010.

Lutker et al, "Crystal Polymorphism in a Carbamazepine Derivative: Oxcarbazepine". NIH Public Access. J Pharm Sci. Feb. 2010 ; 99(2): 794-803. doi: 10.1002/jps.21873.

Madsen-Duggan et al. "Lead optimization of 5.6-diarylpyridines as CB1 receptor inverse agonists" Bioorganic & Medicinal Chemistry Letters (2007) vol. 17, pp. 2031-2035.

Maison, "Multicomponent synthesis of novel amino acid-nucleobase chimeras: a versatile approach to PNA-monomers," Bioorganic & Medicinal Chemistry (2000) vol. 8, pp. 1343-1360.

May et al, How many species are there on earth, Science (1988) vol. 241, p. 1441.

McRobbie et al. "MRI from Picture to Proton," Cambridge University Press, 2007, pp. 307-308.

Mikhailichenko, S. N., et al. "sym-triazines. 7. Hydrolysis and cyclization of 1, 3, 5-triazine series mononitriles." Chemistry of Heterocyclic Compounds 42.5 (2006): 642-647.

Mikhaylichenko, Svetlana, et al. "Synthesis and structure of new 1, 2, 3-triazolyl substituted 1, 3, 5-triazines." European Journal of Chemistry 3.1 (2012): 1-9.

Moreno et al. "Identification of diamine linkers with differing reactivity and their applicationin the synthesis of melamine dendrimers" Tetrahedron Letters (2008) vol. 49, pp. 1152-1154.

Moreno et al. "Molecular recognition in dendrimers based on melamine" Polymer Preprints (2005) vol. 46, No. 2, pp. 1127.

Paronikyan et al. "Synthesis and biological activity of 3-piperazinylpyrano [3,4-C] pyridines" Armyanskii Khimicheskii Zhurnal (1990) vol. 43, No. 8, pp. 518-523.

Parsons et al. "An Integrated Genomic Analysis of Human Glioblastoma Multiforme" Science vol. 321 (2008) pp. 1807-1812 and Supplemental Data.

Pitts et al., "Rapid Synthesis of Triazine Inhibitors of Inosine Monophosphate Dehydrogenase," Bioorganic & Medicinal Chemistry Letters (2002) vol. 12, pp. 2137-2140.

Pollard et al, "Cancer. Puzzling patterns of predisposition." Science. Apr. 10, 2009, vol. 324, 1-5,15-16, 18-22,35-38 No. 5924, pp. 192-194.

Popovici-Muller, Janeta et al. Discovery of the First Potent Inhibitors of Mutant IDH1 That Lower Tumor2-HG in Vivo. ACS Medicinal Chemistry Letters. Sep. 17, 2012 (Sep. 17, 2012), vol. 3, No. 10, 850-855.

PubChem CID 4078245 [online]; Sep. 13, 2005 [retrieved on Feb. 4, 2012]; retrieved from http://pubchem.ncbi.nim.nih.gov/; 2d-structure.

PubChem CID 4854170 [online]; Sep. 17, 2005 [retrieved on Feb. 4, 2012]; retrieved from http://pubchem.ncbi.nim.nih.gov/; 2d-structure.

Ramos et al. "Current approaches in the treatment of relapsed and refractory acute myeloid leukemia," Journal of Clinical Medicine, 2015, 4(4):665-695.

Rao et al., "Polymorphism in Drugs and its Significance in Therapeutics". Journal of Scientific & Industrial Research vol. 46 Oct. 1987 pp. 450-455.

Raynaud et al. "Absence of R140Q Mutation of Isocitrate Dehydrogenase 2 in Gliomas and Breast Cancers" Oncology Letters (2010) vol. 1, No. 5, pp. 883-884.

Registry (STN) [online], Aug. 23, 2006 [Retrieved on Jan. 29, 2016] CAS Registration No. 903862-76-0.

Registry (STN) [online], Aug. 23, 2006 [Retrieved on Jan. 29, 2016] CAS Registration No. 903869-26-1.

(56) References Cited

OTHER PUBLICATIONS

Registry (STN) [online], Apr. 13, 2007 [Retrieved on Jan. 29, 2016] CAS Registration No. 929819-92-1.
Registry (STN) [online], Apr. 13, 2007 [Retrieved on Jan. 29, 2016] CAS Registration No. 929971-43-7.
Registry (STN) [online], Jul. 3, 2008, CAS Registration No. 1032461-94-1.
Registry (STN) [online], Jul. 3, 2008, CAS Registration No. 1032470-22-6.
Registry (STN) [online], Jul. 4, 2008, CAS Registration No. 1032747-65-1.
Registry (STN) [online], Apr. 19, 2009 [Retrieved on Jan. 29, 2016] CAS Registration No. 1136498-70-8.
Registry (STN) [online], Aug. 27, 2009 [Retrieved on Jan. 29, 2016] CAS Registration No. 1176756-98-1.
Registry (STN) [online], Apr. 16, 2010, CAS Registration No. 1219379-97-1.
Reitman et al. "Isocitrate Sehydrogenase 1 and 2 Mutations in Cancer: Alterations at a Crossroads of Cellular Metabolism" Journal of the National Cancer Institute, vol. 102, No. 13, pp. 932-941 (2010).
Rohle et al. "An Inhibitor of Mutant IDH1 Delays Growth and Promotes Differentiation of Glioma Cells" Science, vol. 340, No. 6132 pp. 626-630 (2013).
Scharn et al. "Spatially Addressed Synthesis of Amino- and Amino-Oxy-Substituted 1,3,5-Triazine Arrays on Polymeric Membranes" Journal of Combinatorial Chemistry (2000) vol. 2, No. 4, pp. 361-369.
Search Report for SG 11201600185U dated Nov. 16, 2016.
Serajuddin et al. "Solid dispersion of poorly water-soluable drugs: early promises, subsequent problems, and recent breakthroughs," Journal of Pharmaceutical Sciences, 1999, 88(10):1058-1066.
Shahin et al., "Elaborate ligand-based modeling and subsequent synthetic exploration unveil new nanomora Ca2+/Calmodulin-dependent protein kinase II inhibitory leads" Bioorganic & Medicinal Chemistry (2012) vol. 20, pp. 377-400.
Shih et al. "The Role of Mutations in Epigenetic Regulators in Myeloid Malignancies" Nature Reviews Cancer (2012) vol. 12, No. 9, pp. 599-612.
Sirkanyan, S.N. et al Synthesis of new derivatives of piperazine-substituted pyrano[3,4-c]pyridines. Hayastani Kimiakan Handes 2009, vol. 62, No. 3-4 pp. 378-385. English Abstract Only.
Sonoda et al. "Analysis of IDH1 and IDH2 mutations in Japanese glioma patients" Cancer Science, vol. 100, No. 10, pp. 1996-1998 (2009).
Sosnovik et al. "Emerging concepts in molecular MRI." Curr. Op. Biotech., 2007, 18, 4-10.
STN file CA, Registry No. 1023444-33-8, entered STN on May 29, 2008, Chemical Abstracts Index Name "Benzenesulfonamide, 3-[[4-(1,3-benzodioxol-5-ylmethyl)-1-piperazinyl]carbonyl]-N-(4-butylphenyl)-4-methyl-".
STN File CA, Registry No. 1090629-29-0, entered STN on Dec. 28, 2008, Chemical Abstracts Index Name "Benzenesulfonamide, 3-[[4-[(2,5-dimethoxyphenyl)methyl]-1-piperazinyl]carbonyl]-N-(4-methoxyphenyl)-4-methyl-".
STN File CA, Registry No. 134538-28-6, entered STN on Jun. 28, 1991, Chemical Abstracts Index Name "1H-Pyrano[3,4-c]pyridine-5-carbonitrile,3,4-dihydro-3,3-dimethyl-6-[4-(1-oxobutyl)-1-piperazinyl]-8-phenyl-", disclosed in Paronikyan et al. Armyanskii Khimicheskii Zhurnal, 1990, vol. 43, No. 8.
STN File CA, Registry No. 134538-29-7, entered STN on Jun. 28, 1991, Chemical Abstracts Index Name "1H-Pyrano[3,4-c]pyridine-5-carbonitrile,3,4-dihydro-3,3-dimethyl-6-[4-(2-methyl-1-oxopropyl)-1-piperazinyl]-8-phenyl-", disclosed in Paronikyan et al. Armyanskii Khimicheskii Zhurnal, 1990, vol. 43, No. 8.
STN File CA, Registry No. 134538-30-0, entered STN on Jun. 28, 1991, Chemical Abstracts Index Name "1H-Pyrano[3,4-c]pyridine-5-carbonitrile,6-(4-benzoyl-1-piperazinyl)-3,4-dihydro-3,3-dimethyl-8-phenyl-", disclosed in Paronikyan et al. Armyanskii Khimicheskii Zhurnal, 1990, vol. 43, No. 8.

STN File CA, Registry No. 134538-31-1, entered STN on Jun. 28, 1991, Chemical Abstracts Index Name "1H-Pyrano[3,4-c]pyridine-5-carbonitrile,6-[4-(2-furanylcarbonyl)-1-piperazinyl]-3,4-dihydro-3,3-dimethyl-8-phenyl-", disclosed in Paronikyan et al. Armyanskii Khimicheskii Zhurnal, 1990, vol. 43, No. 8.
STN File CA, Registry No. 380466-24-0 entered STN on Jan. 4, 2002, Chemical Abstracts Index Name "Benzenesulfonamide, N-methyl-N-phenyl-3-[[4-(2-pyridinyl)-1-piperazinyl]carbonyl]".
STN file CA, Registry No. 713505-78-3, entered STN on Jul. 21, 2004, Chemical Abstracts Index Name "1-Piperazinecarboxylic acid, 4-[4-methyl-3-[(phenylamino)sulfonyl]benzoyl]-, ethyl ester".
STN File CA, Registry No. 736168-79-9 entered STN on Aug. 31, 2004, Chemical Abstracts Index Name "Benzenesulfonamide, 3,4-difluoro-N-[3-334-(phenylmethyl0-1-piperazinyl]carbonyl]phenyl".
STN File CA, Registry No. 847757-57-7, entered STN on Apr. 1, 2005, Chemical Abstracts Index Name "Benzenesulfonamide, 3-[[4-(1,3-benzodioxol-5-ylmethyl)-1-piperazinyl]carbonyl]-N-(4-ethoxyphenyl)-N,4-dimethyl-" or "Piperazine, 1-(1,3-benzodioxol-5-ylmethyl)-4-[5-[[(4-ethoxyphenyl)methylamino]sulfonyl]-2-methylbenzoyl]-".
STN Registry, L23 Answer 2 of 3 (CAS No. 1032450-21-7), Database: ASINEX Ltd., Entered STN: Jul. 3, 2008 (Jul. 3, 2008).
STN Registry. L23 Answer 1 of 3 (CAS No. 1038821-72-5), Database: ChemDB (University of California Irvine), Entered STN: Aug. 5, 2008 (Aug. 5, 2008).
STN Tokyo, Registry No. 1001833-18-6, Entered STN on Feb. 6, 2008, Chemical Abstracts Index Name "1,4-Benzodioxin-6-sulfonamide, 2,3-dihydro-N-[4- [(4-methyl-I-piperazinyl)carbonyl]phenyl]-".
STN Tokyo, Registry No. 1030142-35-8, Entered STN on Jun. 24, 2008, Chemical Abstracts Index Name "1,4-Benzodioxin-6-sulfonamide, 2,3-dihydro-N-[4- [[4-[(5-methyl-3-isoxazolyl)methyl]-I-piperazinyl]carbonyl]phenyl]-".
STN Tokyo, Registry No. 1031531-78-8, Entered STN on Jun. 29, 2008 Chemical Abstracts Index Name "1,4-Benzodioxin-6-sulfonamide, N-4[4-[(4-acetyl-1-piperazinyl)carbonyl]phenyl]-2,3-dihydro-".
STN Tokyo, Registry No. 1057928-35-4, Entered STN on Oct. 7, 2008, Chemical Abstracts Index Name "1,4-Benzodioxin-6-sulfonamide, 2,3-dihydro-N-[4- [[4-(2-pyridinyl)-1-piperazinyl]carbonyl]phenyl]-".
STN Tokyo, Registry No. 1240875-00-6, entered STN on Sep. 14, 2010, Chemical Abstracts Index Name "1,4-Benzodioxin-6-sulfonamide, 2,3-dihydro-N-[4-[[4-(2-thiazolyl)-1-piperazinyl]carbonyl]phenyl]-".
STN Tokyo, Registry No. 748791-86-8, Entered STN on Sep. 21, 2004, Chemical Abstracts Index Name "1,4-Benzodioxin-6-sulfonamide, N-[4- [[4-(2-furanylcarbonyl)-1-piperazinyl]carbonyl]phenyl]-2,3-dihydro-".
STN Tokyo, Registry No. 878469-24-0, Entered STN on Mar. 29, 2006, Chemical Abstracts Index Name "1,4-Benzodioxin-6-sulfonamide, 2,3-dihydro-N-[4-[[4-(2-pyrimidinyl)-1-piperazinyl]carbonyl]phenyl]-".
STN Tokyo, Registry No. 878474-39-6, Entered STN on Mar. 29, 2006, Chemical Abstracts Index Name "1,4-Benzodioxin-6-sulfonamide, 2,3-dihydro-N[4[(4-phenyl-1-piperazinyl)carbonyl]phenyl]-".
STN Tokyo, Registry No. 878590-33-1, Entered STN on Mar. 30, 2006, Chemical Abstracts Index Name "1,4-Benzodioxin-6-sulfonamide, 2,3-dihydro-N-[4-{{4-(tetrahydro-2-furanyl)methyl]-1-piperazinyl]carbonyl]phenyl]-".
STN Tokyo, Registry No. 878943-66-9 Entered STN on Apr. 2, 2006, Chemical Abstracts Index Name "1,4-Benzodioxin-6-sulfonamide, 3,4-dihydro-N-[[4-(2-pyrimidinyl)-1-piperazinyl]carbonyl]phenyl]-".
STN Tokyo, Registry No. 878956-06-0, Entered STN on Apr. 2, 2006, Chemical Abstracts Index Name "1,4-Benzodioxin-6-sulfonamide, N-[4- [[4-(cyclopropylcarbonyl)-1-piperazinyl]carbonyl]phenyl]-2,3-dihydro-".
STN Tokyo, Registry No. 920679-46-5, Entered STN on Feb. 13, 2007, Chemical Abstracts Index Name "1,4-Benzodioxin-6-sulfonamide, 2,3-dihydro-N-[4- [[4-(4-pyridinyl)-1-piperazinyl]carbonyl]phenyl]-".

(56) References Cited

OTHER PUBLICATIONS

STN Tokyo, Registry No. 920822-52-2, Entered STN on Feb. 14, 2007, Chemical Abstracts Index Name "1,4-Benzodioxin-6-sulfonamide, N-[4- [[4-(4-fluoropheyl)-1-piperazinyl]carbonyl]phenyl] - 2,3dihydro-".
STN Tokyo, Registry No. 920824-56-2, Entered STN on Feb. 14, 2007, Chemical Abstracts Index Name "1,4-Benzodioxin-6-sulfonamide, 2,3-dihydro-N-[4- [[4-(3-thienylmethyl)-1-piperazinyl]carbonyl]phenyl]-".
STN Tokyo, Registry No. 920847-34-3, Entered STN on Feb. 14, 2007, Chemical Abstracts Index Name "1,4-Benzodioxin-6-sulfonamide, 2,3-dihydro-N-[4- [[4-(2-methylphenyl)-1-piperazinyl]carbonyl]phenyl]-".
STN Tokyo, Registry No. 920875-39-4, Entered STN on Feb. 14, 2007, Chemical Abstracts Index Name "1,4-Benzodioxin-6-sulfonamide, 2,3-dihydro-N-[4- [[4-(2-hydroxyphenyl)-1-piperazinyl]carbonyl]phenyl]-".
STN Tokyo, Registry No. 920902-88-1, Entered STN on Feb. 14, 2007, Chemical Abstracts Index Name "1,4-Benzodioxin-6-sulfonamide, 2,3-dihydro-N-[4- [[4-(2-thienylmethyl)-I-piperazinyl]carbonyl]phenyl]-".
STN Tokyo, Registry No. 920921-09-1 Entered STN on Feb. 14, 2007, Chemical Abstracts Index Name "2H-1, 5-Benzodioxepin-7-sulfonamide, 3,4-dihydro-N-[4-[[4-(2pyridinyl)-1-piperazinyl]carbonyl]phenyl]-".
STN Tokyo, Registry No. 920924-42-1, Entered STN on Feb. 14, 2007, Chemical Abstracts Index Name "1,4-Benzodioxin-6-sulfonamide, 2,3-dihydro-N-[4- [[4-(2-pyridinylmethyl)-1-piperazinyl]carbonyl]phenyl]-".
STN Tokyo, Registry No. 941220-77-5, Entered STN on Jul. 4, 2007, Chemical Abstracts Index Name "2H-1, 5-Benzodioxepin-7-sulfonamide, 3,4-dihydro-N-[4-[(4-methyl-I-piperazinyl)carbonyl]phenyl]-".
Struys et al, Investigations by mass isotopomer analysis of the formation of D-2-hydroxyglutarate by cultured lymphoblasts from two patients with D-2-hydroxyglutaric aciduria, FEBS letters vol. 557, pp. 115-120, (2004).
Struys et al. "Mutations in the D-2-hydroxyglutarate dehydrogenase gene cause D-2-hydroxyglutaric aciduria" American Journal of Human Genetics, 2005. 76:358-360.
Struys, EA. et al. "Measurement of Urinary D- and L-2-Hydroxyglutarate Enantiomers by Stable-Isotope-Dilution LiquidChromatography—Tandem Mass Spectrometry after Derivatization with Diacetyi-L-Tartaric Anhydride." Clinical Chemistry (2004)501391-1395.
Takagi et al. "Synthesis of poly(triazinylstyrene) containing nitrogen-bawed ligand and function as metal ion adsorbent and oxidation catalyst" Reactive & Functional Polymers (2006) vol. 31, pp. 1718-1724.
The radiation fact sheet published by the National Cancer Institute, http://www.cancer.gov/about-cancer/treatment/types/radiation-therapy/radiation-fact-sheet, reviewed Jun. 30, 2010.
Thompson, "Metabolic Enzymes as Oncogenes or Tumor Suppressors." The New England 18-22 Journal of Medicine, Feb. 19, 2009, vol. 360, No. 8, pp. 813-815; p. 813, p. 815, col. 1; Fig 1.
Van Schaftingen et al. "L-2-Hydroglutaric aciduria, a disorder of metabolite repair" J Inherit. Metab. Dis. (2009) vol. 32, pp. 135-142.
Wang et al "Facile Synthesis of 2,4-Dianiino-6-alkyi- or 6-Aryl-PyrimidineDerivatives" Journal of Heterocyclic Chemistry (2010) vol. 47 pp. 1056-1061.
Wang et al. "A novel ligand N,N?-di(2-pyridyl)-2,4-diamino-6-phenyl-1,3,5-triazine (dpdapt) and its complexes: [Cu (dpdapt)Cl2] and [Cu(dpdapt)(NO3)(H2O)] Â• NO3 Â• H2O" Polyhedron, 2006. vol. 25, Issue 1. pp. 195-202.
Ward, Patrick S, "The Common Feature of Leukemia-Associated IDH1 and IDH2 Mutations Is a Neomorphic Enzyme Activity Converting [alpha]-Ketoglutarate to 2-Hydroxyglutarate" Cancer cell, vol. 17,Nr:3,pp. 225-234, 2010.
Watanabe et al., "IDH1 Mutations Are Early Events in the Development of Astrocytomas and Oligodendrogliomas". American Journal of Pathology, Apr. 2009 (published online Feb. 26, 2009, vol. 174, No. 4, pp. 1149-1153; Abstract, p. 1150, col. 1.
Written Opinion for SG 11201600185U dated Nov. 16, 2016.
Yan et al., "IDH1 and IDH2 Mutations in Gliomas" The New England Journal of Medicine, 79 Feb. 18-22, 2009, vol. 360, No. 8, pp. 765-773.
Yrjola et al., "Discovery of novel cannabinoid receptor ligands by a virtual screening approach: Further development of 2,4,6-trisubstituted 1,3,5-triazines as CB2 agonists," European Journal of Pharmaceutical Sciences (2013) vol. 48, pp. 9-20.
Zhao et al: "Glioma-derived mutations in IDH1 dominantly inhibit IDH1 catalytic activity and induce HIF-1alpha", Science, vol. 324, No. 5924, Apr. 10, 2009 (Apr. 10, 2009), pp. 261-265.
Zheng et al. "Synthesis and antitumor evaluation of a novel series of triaminotriazine derivatives" Bioorganic & Medicinal Chemistry (2007) vol. 15, pp. 1815-1827.
Zuo et al. "Synthesis of 4-methyl-1,2,3-thiadiazole derivatives via ugi reaction and their biological activities," Journal of Agricultural and Food Chemistry, 2010, 58(5): 2755-2762.
Im et al. "DNMT3A and IDH mutations in acute myeloid leukemia and other myeloid malignancies: Associations with prognosis and potential treatment strategies," Leukemia, 2014, 28:1774-1783.
International Search Report for PCT/US2016/057042 dated Jan. 12, 2017.
Aghili et al. "Hydroxyglutaric aciduria and malignant brain tumor: a case report and literature review", Journal of Neuroncology, 2008. 91:233-236.
Amary et al. "Ollier disease and Maffucci syndrome are caused by somatic mosaic mutations of IDH1 and IDH2," Nature Genetics Letters, 2011, 43(12):1262-1266.
Ansell et al. "The interactions of artificial coenzymes with alcohol dehydrogenase and other NAD(P)(H) dependent enzymes" Journal of Molecular Catalysis B: Enzymatic (1999) vol. 6, No. 1-2, pp. 111-123.
Balss, "Analysis of the IDH1 codon 132 mutation in brain tumors", Acata Neuropathol (2008) vol. 116, pp. 597-602.
Benner et al, "Evolution, language and analogy in functional genomics", Trends in Genetics (2001) vol. 17, pp. 414-418.
Bhushan et al. "Reversed-phase liquid chromatographic resolution of diastereomers of protein and non-protein amino acids prepared with newly synthesized chiral derivatizing reagents based on cyanuric chloride" Amino Acids (2011) vol. 40, pp. 403-409.
Bleeker et al., "IDH1 mutations at residue p. R132 (IDH1 (R132)) occur frequently in high-grade 18-22 gliomas but not in other solid tumors." Hum Muta1., Jan. 2009, vol. 30, No. 1, pp. 7-11.
Braun et al. "Triazine-based polymers: 4. MALDI-MS of triazine-based polyamines" Polymer (1996) vol. 37, No. 5, pp. 777-783.
Burger et al. "Nuclear substituted 3,4-dihydroxyphenethylamines and related derivatives," Journal of American Chemical Society, 1956, 78(17):4419-4422.
Cairns et al. "Oncogenic Isocitrate Dehydrogenase Mutations: Mechanisms, Models, and Clinical Opportunities" Cancer Discovery (2013) vol. 3, Iss 7, pp. 730-741.
Cecil Textbook of Medicine, edited by Bennet, J.C., and Plum F., 20th edition, vol. 1, 1004-1010, 1996.
Chan et al. "Multi-domain hydrogen-bond forming metal chelates: X-ray crystal structuresof dicyclopalladated 2,3-bis[6-(2-amino-4-phenylamino-1 ,3,5-triazinyl)]pyrazine(H2L) [Pd2Br2L] and 2,6-bis[6-(2-amino-4-phenylamino-1,3,5-triazinylium)]-pyridine dichloride" Chemical Communications (1996) No. 1, pp. 81-83.
Chapman et al. "Substituted aminopyrimidine protein kinase B (PknB) inhibitorsshow activity against *Mycobacterium tuberculosis*" Bioorganic & Medicinal Chemistry Letters (2012) vol. 22, pp. 3349-3353.
Chen et al. "Cytotoxicity, Hemolysis, and Acute in Vivo Toxicity of Dendrimers Based on Melamine, Candidate Vehicles for Delivery" J. Am. Chem. Soc. (2004) vol. 126, No. 32, pp. 10044-10048.
Cocco et al. "Synthesis of Triflouromethylated Pyridinecarbonitriles" Journal of Heterocyclic Chemistry, 1995. vol. 32 pp. 543-545.

(56) References Cited

OTHER PUBLICATIONS

Dang et al., "Cancer-associated IDH1 mutations produce 2-hydroxyglutarate." Nature, 10 29-32 Dec. 2009, vol. 462, No. 7274, pp. 739-744.

Dang et al. "IDH Mutations in Glioma and Acute Myeloid Leukemia" Trends in Molecular Medicine (2010) vol. 16, No. 9, pp. 387-397.

Database CA [Online] Chemical Abstracts Service, Columbus,Ohio, US; Ambartsumyan, E. N. et al: "Synthesis and transformations of chloropyrazolylazines", XP002764692, retrieved from STN Database accession No. 2012:876343 * abstract * & Ambartsumyan, E. N. et al: "Synthesis and transformations of chloropyrazolylazines", Hayastani Kimiakan Handes ( 2011 ), 64(4), 544-550 Coden: KZARF3; ISSN: 1561-4190, 2011.

Database CA [Online] Chemical Abstracts Service. Columbus.Ohio. US; Baibulova M. S. et al:Syntheses from pyridylguanamines_ XP002764691. retrieved from STN Database accession No. 1990:406282 * abstract* & Bai Bulova, M. S. et al: Syntheses from pyridylguanamines, Izvestiya Akademii Nauk Kazakhskoi SSR, Seriya Khimicheskaya, (5), 40-2 Coden: Ikakak; ISSN: 0002-3205, 1989.

Database CA [Online] Chemical Abstracts Service. Columbus.Ohio. US; Krimmer. Hans Peter et al: "Reaction of .beta.-mercapto .alpha.-amino acids with nitriles".XP002764690.retrieved from STN Database accession No. 1988:529623* abstract* & Krimmer. Hans Peter et al: "Reaction of .beta.-mercapto .alpha.-amino acids with nitriles".Chemiker-Zeitung â€¢ 111(12). 357-61 Coden: CMKZAT; ISSN: 0009-2894.1987.

Davis et al. "Biochemical, Cellular, and Biophysical Characterization of a Potent Inhibitor of Mutant Isocitrate Dehydrogenase IDH1" The Journal of Biological Chemistry (2014) vol. 289, No. 20, pp. 13717-13725.

Dermer et al., "Another Anniversary for the War on Cancer", Bio/Technology, 1994, 12:320.

Docoslis et al., "Characterization of the Distribution, Polymorphism, and Stability of Nimodipine in Its Solid Dispersions in Polyethylene Glycol by Micro-Raman Spectroscopy and Powder X-Ray Diffraction". The AAPS Journal 2007; 9 (3) Article 43, E361-E370.

Dohner et al. "Acute myeloid leukemia," New England Journal of Medicine, 2015, 373:1136-52.

Dohner et al. "Impact of Genetic Features on Treatment Decisions in AML" American Society of Hematology (2011) pp. 36-42.

Drew, MGB, et al. "Solvent extraction and lanthanide complexation studies with new terdentate ligands containing two 1, 3, 5-triazine moieties." Dalton Transactions 2 (2004): 244-251.

Duanmu et al. "Dendron-Functionalized Superparamagnetic Nanoparticles with Switchable Solubility in Organic and Aqueous Media: Matriced for Homogeneous Catalysis and Potential MRI Contrast Agents" Chem. Mater. (2006) vol. 18, No. 25, pp. 5973-5981.

Enholm, EJ., Jed M. Hastings, and Chris Edwards. "Hydrogen-Bonded Arrays Coupled by Cross-Metathesis." Synlett Feb. 2008 (2008): 203-206.

Extended European Search Report for PCT/CN2014081957 dated Dec. 9, 2016.

Freshney et al.,Culture of Animal Cells, A Manual of Basic Technique, Alan R. Liss, Inc., 1983, New York, p. 4.

Genetics Home Reference. "L2HGDH." accessed at <http://ghr.nlm.nih.gov/gene/L2HGDH> on Sep. 4, 2015.

Gewald et al. "Discovery of triazines as potent, selective and orally active PDE4 inhibitors" Bioorganic & medicinal Chemistry Letters (2013) vol. 23, pp. 4308-4314.

Golub et al., "Molecular Classification of Cancer: Class Discovery and Class Prediction by Gene Expression Monitoring", Science, 286, 531-537, 1999.

Gura. "Systems for identifying new drugs are often faulty," Science, 1997, 278(5340):1041-2.

Hartmann et al. "Type and Frequency of IDH1 and IDH2 mutations are related to astrocytic and oligodendroglial differentiation and age: a study of 1010 diffuse gliomas" Acta Neuropathologica (2009) 118: 469-474.

Ho et al., "Triazine and pyrimidine based ROCK inhibitors with efficacy in spontaneous hypertensive rat model." Bioorganic & Medicinal Chemistry Letters (2009) vol. 19, pp. 6027-6031.

Holmes et al, 750 MHz 1H NMR spectroscopy characterisation of the complex metabolic pattern of urine from patients with inborn errors of metabolism: 2-hydroxyglutaric aciduria and maple syrup urine disease., Journal of Pharmaceutical and Biomedical Analysis (1997) vol. 15, pp. 1647-1659.

Huang et al., "N4-phenyl modifications of N2-(2-hydroxyl)ethyl-6-(pyrrolidin-1-yl)-1,3,5-triazine-2,4-diamines enhance glucocerebrosidase inhibition by small molecules with potential as chemical chaperones for Gaucher disease," Bioorganic & Medicinal Chemistry Letters (2007) vol. 12, pp. 5783-5789.

Irikura et al. "New s-Triazine Derivatives as Depressants for Reticuloendothelial Hyperfunction Induced by Bacterial Endotoxin" Journal of Medicinal Chemistry (2000) vol. 31, pp. 1081-1089.

Jana et al., "Synthesis and Antibacterial Activity of Some Novel 4-Benzyl-piperazinyl-s-triazine Derivatives." Asian Journal of Chemistry (2013) vol. 25, No. 1, pp. 186-190.

Jennings et al, Expression and mutagenesis of mammalian cytosolic NADP+-specific isocitrate dehydrogenase, Biochemistry (1997)vol. 36, pp. 13743-13747.

Johannessen et al. "Rapid conversion of mutant IDH1 from driver to passenger in model of human gliomagenesis," Molecular Cancer Resarch, 2016, 14(10): 976-83.

Johnson et al. "Relationships between drug activity in NCI preclinical in vitro and in vivo models and early clinical trials," British Journal of Cancer, 2001, 84(10): 1424-1431.

Kaila et al. "A convenient one-pot synthesis of trisubstituted 1,3,5-triazines through intermediary amidinothioureas" Tetrahedron Letters (2010) vol. 51, pp. 1486-1489.

Kelarev et al. "Synthesis and properties of sym-triazines. 10 Synthesis of 2,4-diamino-sym-triazines containing a sterically hindered phenol substituent" Chemistry of Heterocyclic Compounds (1992) vol. 28, No. 10, pp. 1189-1193.

Kim et al "Ser95, Asn97, and Thr78 are important for the catalytic function of porcine NADP-dependent isocitrate dehydrogenase" Protein Science (2005) 14: pp. 140-147.

Kim et al. "Identification and Functional Characterization of a Novel, Tissue-specific NAD1-dependent Isocitrate Dehydrogenase b Subunit Isoform" JBC. Dec. 24, 1999, vol. 274 No. 52 pp. 36866-36875.

Koshelev et al. "Synthesis of 1-3,7 N-substituted 2,4-diamino-1,3,5-triazines containing pyridyl groups" Russian Journal of Organic Chemistry (1995) vol. 31, No. 2, pp. 260-263.

Kranendijk et al. "IDH2 Mutations in Patients with D-2-Hydroxyglutaric Aciduria" Science (2010) vol. 330, p. 336.

Krell et al., "IDH mutations in tumorigenesis and their potential role as novel therapeutic targets" Future Oncology (2013) vol. 9, Iss 12, pp. 1923-1935.

Astellas, "Dose escalation study investigating the safety, tolerability, pharmacokinetics, pharmacodynamics of ASP2215 in patients with relapsed or refractory acute myeloid leukemia," (Astellas Pharma Global Development, Inc., https://clinicaltrials.gov/ct2/history/NCT02014558?V_11=View#StudyPageTop, Dec. 12, 2013 (v1), obtained from the internet Jun. 21, 2019).

Brittain et al. "Polymorphism in pharmaceutical solids," 2009, chapter 1, p. 1-10 and chapter 5, 183-226.

Byrn et al. "Pharmaceutical solids: A strategic approach to regulatory considerations," Pharmaceutical Research, 1995, 12(7):945-954.

Caira et al. "Crystalline polymorphism of organic compounds," Topics in Current Chemistry, Springer, Berlin, DE, 1998, vol. 198, pp. 163-208.

Dohner et al. "Impact of genetic features on treatment decisions in AML" ASH Education Program Book, 2011, 1:36-42.

(56) References Cited

OTHER PUBLICATIONS

Emadi et al. "Presence of isocitrate dehydrogenase mutations may predict clinical response to hypomethylating agents in patients with acute myeloid leukemia," American Journal of Hematology, 2015, 90(5):E77-E79.
Friesen et al. "Hydroxypropyl Methylcellulose Acetate Succinate-Based Spray-Dried Dispersions: An Overview," Molecular Pharmaceutics, 2008, 5(6):1003-1019.
Hashida, Design and Evaluation of Oral Administration Formulations, Jiho Inc., 1995, 172-185.
Hashida, Design and Evaluation of Oral Administration Formulations, Jiho Inc., 1995, 76-79.
Lazzarino et al. "Mitoxantrone and etoposide: An effective regimen for refractory or relapsed acute myelogenous leukemia," European Journal of Haematology, 1989, 43:411-416.
Levis et al. "Results of a first-in-human, phase I/II trial of ASP2215, a selective, potent inhibitor of FLT3/Axl in patients with relapsed or refractory (R/R) acute myeloid leukemia," Journal of Clinical Oncology, 2015, 33(15 suppl):7003.
Shafer et al. "Update on rational tareted therapy in AML," Blood Reviews, 2016, 30:275-283.
Shuichi et al. "Long-term follow-up of the randomized JALSG AML 201 study comparing high dose Ara-C therapy with conventional consolidation therapy in adult acute myeloid leukemia (AML)," Blood, 2008, 112(11):135.
Huang et al. "Fundamental aspects of solid dispersion technology for poorly soluble drugs," Acta Pharmaceutica Sinica B, 2014, 4(1):18-25.

* cited by examiner

A. SEQUENTIAL QDx3 AZA + Cmpd2 EPO Differentiation Assay

B. CONCURRENT AZA + Cmpd2 EPO Differentiation Assay

Endpoint Analysis:
✓ Cell pellet color evaluation (hemaglobinization)
✓ HBG, KLF1 qRT-PCR
✓ CD235a FACS
✓ IncuCyte Zoom growth and death analysis

COMBINATION THERAPY FOR TREATING MALIGNANCIES

CLAIM OF PRIORITY

This application is a national stage application under 35 U.S.C. 371 of International Application No. PCT/US2016/057042 filed Oct. 14, 2016, which claims priority from U.S. Ser. No. 62/242,282 filed Oct. 15, 2015, each of which is incorporated herein by reference in its entirety.

FIELD

Provided herein are combination therapies for treating hematological malignancies and solid tumors. In one embodiment, the therapies involve treatment with an IDH1 inhibitor and a DNA demethylating agent.

BACKGROUND

Isocitrate dehydrogenases (IDHs) catalyze the oxidative decarboxylation of isocitrate to 2-oxoglutarate (i.e., α-ketoglutarate). These enzymes belong to two distinct subclasses, one of which utilizes NAD(+) as the electron acceptor and the other NADP(+). Five isocitrate dehydrogenases have been reported: three NAD(+)-dependent isocitrate dehydrogenases, which localize to the mitochondrial matrix, and two NADP(+)-dependent isocitrate dehydrogenases, one of which is mitochondrial and the other predominantly cytosolic. Each NADP(+)-dependent isozyme is a homodimer.

IDH1 (isocitrate dehydrogenase 1 (NADP+), cytosolic) is also known as IDH; IDP; IDCD; IDPC or PICD. The protein encoded by this gene is the NADP(+)-dependent isocitrate dehydrogenase found in the cytoplasm and peroxisomes. It contains the PTS-1 peroxisomal targeting signal sequence. The presence of this enzyme in peroxisomes suggests roles in the regeneration of NADPH for intraperoxisomal reductions, such as the conversion of 2,4-dienoyl-CoAs to 3-enoyl-CoAs, as well as in peroxisomal reactions that consume 2-oxoglutarate, namely the alpha-hydroxylation of phytanic acid. The cytoplasmic enzyme serves a significant role in cytoplasmic NADPH production.

The human IDH1 gene encodes a protein of 414 amino acids. The nucleotide and amino acid sequences for human IDH1 can be found as GenBank entries NM_005896.2 and NP_005887.2 respectively. The nucleotide and amino acid sequences for IDH1 are also described in, e.g., Nekrutenko et al., Mol. Biol. Evol. 15:1674-1684(1998); Geisbrecht et al., J. Biol. Chem. 274:30527-30533(1999); Wiemann et al., Genome Res. 11:422-435(2001); The MGC Project Team, Genome Res. 14:2121-2127(2004); Lubec et al., Submitted (December-2008) to UniProtKB; Kullmann et al., Submitted (June-1996) to the EMBL/GenBank/DDBJ databases; and Sjoeblom et al., Science 314:268-274(2006).

Non-mutant, e.g., wild type, IDH1 catalyzes the oxidative decarboxylation of isocitrate to α-ketoglutarate thereby reducing $NAD^+$ ($NADP^+$) to NADH (NADPH), e.g., in the forward reaction:

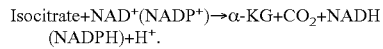

It has been discovered that mutations of IDH1 present in certain cancer cells result in a new ability of the enzyme to catalyze the NAPH-dependent reduction of α-ketoglutarate to R(−)-2-hydroxyglutarate (2HG). The production of 2HG is believed to contribute to the formation and progression of cancer (Dang, L et al, Nature 2009, 462:739-44).

The development of selective inhibitors of an IDH1 mutant enzyme has provided the possibility of therapeutic benefit to AML patients carrying the IDH1 mutation. There have been successful responses in the clinic with decreased blast population and benefit of differentiated functional blood cells. However, the genetic load is present in the patients even with good overall response. Therefore, there is a need for improved therapies for treating cancers having IDH1 mutations.

SUMMARY

In one embodiment, provided herein are methods of treating hematologic malignancies by administering to a subject a combination of a mutant IDH1 inhibitor and a DNA demethylating agent. In one embodiment, the hematologic malignancy is an advanced hematologic malignancy.

In one embodiment, provided herein is a method of treating hematologic malignancies, such as acute myelogenous leukemia (AML), myelodysplastic syndrome (MDS, myeloproliferative neoplasms (MPN), chronic myelomonocytic leukemia (CMML), B-acute lymphoblastic leukemias (B-ALL), or lymphoma (e.g., T-cell lymphoma), each characterized by the presence of a mutant allele of IDH1, comprising administering to a subject a therapeutically effective amount of (S)-N-((S)-1-(2-chlorophenyl)-2-((3,3-difluorocyclobutyl)amino)-2-oxoethyl)-1-(4-cyanopyridin-2-yl)-N-(5-fluoropyridin-3-yl)-5-oxopyrrolidine-2-carboxamide, or a pharmaceutically acceptable salt, solvate, tautomer, stereoisomer, isotopologue, prodrug or a polymorph thereof (COMPOUND 2) and a DNA demethylating agent. In one embodiment, the hematologic malignancy is an advanced hematologic malignancy.

In one embodiment, the DNA demethylating agent is a cytidine analog.

In one embodiment, cytidine analogs useful in the methods provided herein include, but are not limited to, 5-azacitidine (azacitidine), 5-azadeoxycytidine (decitabine), cytarabine, pseudoisocytidine, gemcitabine, zebularine, FCdR, Emtriva, 5,6-dihydro-5-azacitidine and procaine. In one embodiment, the cytidine analog is decitabine or azacitidine. In one embodiment, the cytidine analog is azacitidine.

In one embodiment, provided herein is a method of treating hematologic malignancies, such as acute myelogenous leukemia (AML), myelodysplastic syndrome (MDS), myeloproliferative neoplasms (MPN), chronic myelomonocytic leukemia (CMML), B-acute lymphoblastic leukemias (B-ALL), or lymphoma (e.g., T-cell lymphoma), each characterized by the presence of a mutant allele of IDH1, comprising administering to a subject a therapeutically effective amount of COMPOUND 2 and azacitidine. In one embodiment, the hematologic malignancy is an advanced hematologic malignancy.

In one embodiment, provided herein is a method of treating hematologic malignancies, such as acute myelogenous leukemia (AML), myelodysplastic syndrome (MDS), myeloproliferative neoplasms (MPN), chronic myelomonocytic leukemia (CMML), B-acute lymphoblastic leukemias (B-ALL), or lymphoma (e.g., T-cell lymphoma), each characterized by the presence of a mutant allele of IDH1, comprising administering to a subject a pharmaceutical composition comprising a therapeutically effective amount of COMPOUND 2 and a cytidine analog. In one embodiment, the hematologic malignancy is an advanced hematologic malignancy.

In one embodiment, provided herein is a method of treating hematologic malignancies, such as acute myelogenous leukemia (AML), myelodysplastic syndrome (MDS), myeloproliferative neoplasms (MPN), chronic myelomonocytic leukemia (CMML), B-acute lymphoblastic leukemias (B-ALL), or lymphoma (e.g., T-cell lymphoma), each characterized by the presence of a mutant allele of IDH1, comprising administering to a subject a pharmaceutical composition comprising a therapeutically effective amount of COMPOUND 2 and azacitidine. In one embodiment, the hematologic malignancy is an advanced hematologic malignancy.

In one embodiment, provided herein is a method of treating solid tumors, such as glioma, melanoma, chondrosarcoma, cholangiocarcinoma (including intrahepatic cholangiocarcinoma (IHCC), prostate cancer, colon cancer, or non-small cell lung cancer (NSCLC), each characterized by the presence of a mutant allele of IDH1, comprising administering to a subject a therapeutically effective amount of COMPOUND 2 and a DNA demethylating agent.

In one embodiment, provided herein is a method of treating solid tumors, such as glioma, melanoma, chondrosarcoma, cholangiocarcinoma (including intrahepatic cholangiocarcinoma (IHCC), prostate cancer, colon cancer, or non-small cell lung cancer (NSCLC), each characterized by the presence of a mutant allele of IDH1, comprising administering to a subject a therapeutically effective amount of COMPOUND 2 and azacitidine.

In one embodiment, provided herein is a method of treating solid tumors, such as glioma, melanoma, chondrosarcoma, cholangiocarcinoma (including intrahepatic cholangiocarcinoma (IHCC), prostate cancer, colon cancer, or non-small cell lung cancer (NSCLC), each characterized by the presence of a mutant allele of IDH1, comprising administering to a subject a pharmaceutical composition comprising a therapeutically effective amount of COMPOUND 2 and azacitidine.

In one embodiment, provided herein is a pharmaceutical composition comprising a therapeutically effective amount of COMPOUND 2 and a cytidine analog.

In one embodiment, provided herein is a pharmaceutical composition comprising a therapeutically effective amount of COMPOUND 2 and azacitidine.

DETAILED DESCRIPTION

Figure 1:
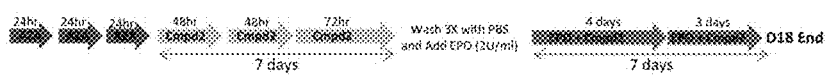
FIG. 1A depicts COMPOUND 2 and azacitidine combination schedule for sequential treatment: 3 days (QD×3) of pre-treatment with azacitidine (AZA), followed by treatment with the COMPOUND 2 for 7 days, followed by erythropoietin (EPO)+COMPOUND 2 for another 7 days. The cells were harvested on Day 18 and subjected to various endpoint assays for monitoring differentiation and death.
FIG. 1B depicts COMPOUND 2 and azacitidine combination schedule for concurrent treatment: treatment for 7 days with the combination of azacitidine and COMPOUND 2, followed by 7 days treatment with azacitidine, COMPOUND 2 and EPO. The cells were harvested on Day 14 and subjected to various endpoint assays for monitoring differentiation and death.
Figure 1:
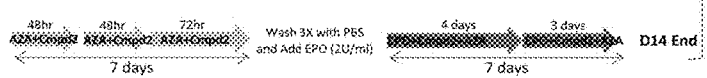

The details of construction and the arrangement of components set forth in the following description or illustrated in the drawings are not meant to be limiting. Other embodiments and different ways to practice the invention are expressly included. Also, the phraseology and terminology used herein is for the purpose of description and should not be regarded as limiting. The use of "including," "comprising," or "having," "containing", "involving", and variations thereof herein, is meant to encompass the items listed thereafter and equivalents thereof as well as additional items.

Definitions

The term a "mutant IDH1 inhibitor" or "inhibitor of IDH1 mutant(s)" means a molecule e.g., a polypeptide, peptide, or small molecule (e.g., a molecule of less than 1,000 daltons), or aptomer, that binds to an IDH1 mutant subunit and inhibits neoactivity, e.g., by inhibiting formation of a dimer, e.g., a homodimer of mutant IDH1 subunits or a heterodimer of a mutant and a wildype subunit. In some embodiments, the neoactivity inhibition is at least about 60%, 70%, 80%, 90%, 95% or 99% as compared to the activity in the absence of the mutant IDH1 inhibitor. In one embodiment, the mutant IDH1 inhibitor is COMPOUND 2.

The term "elevated levels of 2HG" means 10%, 20% 30%, 50%, 75%, 100%, 200%, 500% or more 2HG is present in a subject that carries a mutant IDH1 allele than is present in a subject that does not carry a mutant IDH1 allele. The term "elevated levels of 2HG" may refer to the amount of 2HG within a cell, within a tumor, within an organ comprising a tumor, or within a bodily fluid.

The term "bodily fluid" includes one or more of amniotic fluid surrounding a fetus, aqueous humour, blood (e.g., blood plasma), serum, Cerebrospinal fluid, cerumen, chyme, Cowper's fluid, female ejaculate, interstitial fluid, lymph, breast milk, mucus (e.g., nasal drainage or phlegm), pleural fluid, pus, saliva, sebum, semen, serum, sweat, tears, urine, vaginal secretion, or vomit.

The terms "inhibit" or "prevent" include both complete and partial inhibition and prevention. An inhibitor may completely or partially inhibit the intended target.

The term "subject" is intended to include human and non-human animals. Exemplary human subjects include a human patient (referred to as a patient) having a disorder, e.g., a disorder described herein or a normal subject. The term "non-human animals" of one aspect of the invention includes all vertebrates, e.g., non-mammals (such as chickens, amphibians, reptiles) and mammals, such as non-human primates, domesticated and/or agriculturally useful animals, e.g., sheep, dog, cat, cow, pig, etc.

The term "treat" means decrease, suppress, attenuate, diminish, arrest, or stabilize the development or progression of a disease/disorder (e.g., an hematologic malignancy, including an advanced hematologic malignancy, such as acute myelogenous leukemia (AML), myelodysplastic syndrome (MDS), myeloproliferative neoplasms (MPN), chronic myelomonocytic leukemia (CMML), B-acute lymphoblastic leukemias (B-ALL), or lymphoma (e.g., T-cell lymphoma), or a solid tumor, including glioma, melanoma, chondrosarcoma, cholangiocarcinoma (including intrahepatic cholangiocarcinoma (IHCC), prostate cancer, colon cancer, or non-small cell lung cancer (NSCLC), each characterized by the presence of a mutant allele of IDH1), lessen the severity of the disease/disorder or improve the symptoms associated with the disease/disorder.

An amount of a compound, including a pharmaceutically acceptable salt, solvate, tautomer, stereoisomer, isotopologue, prodrug or a polymorph thereof, effective to treat a disorder, or a "therapeutically effective amount" or "therapeutically effective dose" refers to an amount of the compound, including a pharmaceutically acceptable salt, solvate, tautomer, stereoisomer, isotopologue, prodrug, or a polymorph thereof, which is effective, upon single or multiple dose administration to a subject, in treating a cell, or in curing, alleviating, relieving or improving a subject with a disorder beyond that expected in the absence of such treatment.

The term "co-administering" as used herein with respect to additional cancer therapeutic agents means that the additional cancer therapeutic agent may be administered together with a compound provided herein as part of a single dosage form (such as a composition comprising a compound and a second therapeutic agent as described above) or as separate, multiple dosage forms. Alternatively, the additional cancer therapeutic agent may be administered prior to, consecutively with, or following the administration of a compound provided herein. In such combination therapy treatment, both the compounds provided herein and the second therapeutic agent(s) are administered by conventional methods. The administration of a composition comprising both a compound provided herein and a second therapeutic agent, to a subject does not preclude the separate administration of that same therapeutic agent, any other second therapeutic agent or any compound provided herein to said subject at another time during a course of treatment. The term "co-administering" as used herein with respect to an additional cancer treatment means that the additional cancer treatment may occur prior to, consecutively with, concurrently with or following the administration of a compound provided herein.

The term "DNA demethylating agent" refers to an agent that inhibits the transfer of a methyl group to DNA. In one embodiment, the DNA demethylating agent is a cytidine analog.

The term "a cytidine analog" referred to herein is intended to encompass the free base of the cytidine analog, or a salt, solvate, hydrate, cocrystal, complex, prodrug, precursor, metabolite, and/or derivative thereof. In certain embodiments, a cytidine analog referred to herein encompasses the free base of the cytidine analog, or a salt, solvate, hydrate, cocrystal or complex thereof. In certain embodiments, a cytidine analog referred to herein encompasses the free base of the cytidine analog, or a pharmaceutically acceptable salt, solvate, or hydrate thereof.

The term "substantially free of other stereoisomers" as used herein means a preparation enriched in a compound having a selected stereochemistry at one or more selected stereocenters by at least about 60%, 65%, 70%, 75%, 80%, 85%, 90%, 95%, 96%, 97%, 98%, or 99%.

The term "enriched" means that at least the designated percentage of a preparation is the compound having a selected stereochemistry at one or more selected stereocenters.

The term "crystalline" refers to a solid having a highly regular chemical structure. In particular, a crystalline COMPOUND 2 may be produced as one or more single crystalline forms of COMPOUND 2. For the purposes of this application, the terms "crystalline form", "single crystalline form" and "polymorph" are synonymous; the terms distinguish between crystals that have different properties (e.g., different XRPD patterns and/or different DSC scan results). The term "polymorph" includes pseudopolymorphs, which are typically different solvates of a material, and thus their properties differ from one another. Thus, each distinct polymorph and pseudopolymorph of COMPOUND 2 is considered to be a distinct single crystalline form herein.

The term "substantially crystalline" refers to forms that may be at least a particular weight percent crystalline. Particular weight percentages are 10%, 20%, 30%, 40%, 50%, 60%, 70%, 75%, 80%, 85%, 87%, 88%, 89%, 90%, 91%, 92%, 93%, 94%, 95%, 96%, 97%, 98%, 99%, 99.5%, 99.9%, or any percentage between 10% and 100%. In some embodiments, substantially crystalline refers to a COMPOUND 2 that is at least 70% crystalline. In other embodiments, substantially crystalline refers to a COMPOUND 2 that is at least 90% crystalline.

The term "isolated" refers to forms that may be at least a particular weight percent of a particular crystalline form of compound. Particular weight percentages are 90%, 91%, 92%, 93%, 94%, 95%, 96%, 97%, 98%, 99%, 99.5%, 99.9%, or any percentage between 90% and 100%.

The term "solvate or solvated" means a physical association of a compound, including a crystalline form thereof, of this invention with one or more solvent molecules. This physical association includes hydrogen bonding. In certain instances the solvate will be capable of isolation, for example when one or more solvent molecules are incorporated in the crystal lattice of the crystalline solid. "Solvate or solvated" encompasses both solution-phase and isolable solvates. Representative solvates include, for example, a hydrate, ethanolates or a methanolate.

The term "hydrate" is a solvate wherein the solvent molecule is $H_2O$ that is present in a defined stoichiometric amount, and may, for example, include hemihydrate, monohydrate, dihydrate, or trihydrate.

The term "mixture" is used to refer to the combined elements of the mixture regardless of the phase-state of the combination (e.g., liquid or liquid/crystalline).

The term "seeding" is used to refer to the addition of a crystalline material to initiate recrystallization or crystallization.

The term "antisolvent" is used to refer to a solvent in which compounds, including crystalline forms thereof, are poorly soluble.

The term "pharmaceutically acceptable carrier or adjuvant" refers to a carrier or adjuvant that may be administered to a subject, together with a compound of one aspect of this invention, and which does not destroy the pharmacological activity thereof and is nontoxic when administered in doses sufficient to deliver a therapeutic amount of the compound.

The term "a pharmaceutically-acceptable salt" as used herein refers to non-toxic acid or base addition salts of the compound to which the term refers. Examples of pharmaceutically acceptable salts are discussed in Berge et al., 1977, "Pharmaceutically Acceptable Salts." *J. Pharm. Sci.* Vol. 66, pp. 1-19.

The term "about" means approximately, in the region of, roughly, or around. When the term "about" is used in conjunction with a numerical range, it modifies that range by extending the boundaries above and below the numerical values set forth. In general, the term "about" is used herein to modify a numerical value above and below the stated value by a variance of 10%.

Compounds

COMPOUND 2 is (S)-N-((S)-1-(2-chlorophenyl)-2-((3,3-difluorocyclobutyl)amino)-2-oxoethyl)-1-(4-cyanopyridin-2-yl)-N-(5-fluoropyridin-3-yl)-5-oxopyrrolidine-2-carboxamide, a pharmaceutically acceptable salt, solvate, tautomer, stereoisomer, isotopologue, prodrug, or a polymorph thereof. COMPOUND 2 has the following chemical structure:

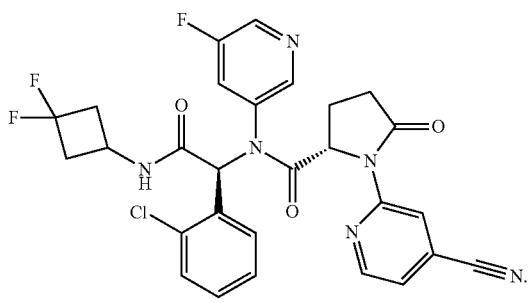 [SMILES: N#Cc1ccnc(N2C(=O)CC[C@H]2C(=O)N(c2cncc(F)c2)[C@H](C(=O)NC2CC(F)(F)C2)c2ccccc2Cl)c1]

COMPOUND 2 may also comprise one or more isotopic substitutions. For example, H may be in any isotopic form ("Isotopologues"), including $^1H$, $^2H$ (D or deuterium), and $^3H$ (T or tritium); C may be in any isotopic form, including $^{12}C$, $^{13}C$, and $^{14}C$; O may be in any isotopic form, including $^{16}O$ and $^{18}O$; and the like. For example, COMPOUND 2 is enriched in a specific isotopic form of H, C and/or O by at least about 60%, 65%, 70%, 75%, 80%, 85%, 90%, 95%, 96%, 97%, 98%, or 99%.

COMPOUND 2 in certain embodiments may also be represented in multiple tautomeric forms, in such instances, one aspect of the invention expressly includes all tautomeric forms of COMPOUND 2 described herein, even though only a single tautomeric form may be represented (e.g., keto-enol tautomers). All such isomeric forms of COMPOUND 2 are expressly included herein. Synthesis of COMPOUND 2 is described in US published application US-2013-0190249-A1 published Jul. 25, 2013, which is incorporated by reference in its entirety.

It may be convenient or desirable to prepare, purify, and/or handle a corresponding salt of COMPOUND 2, for example, a pharmaceutically-acceptable salt. Examples of pharmaceutically acceptable salts are discussed in Berge et al., 1977, "Pharmaceutically Acceptable Salts." *J. Pharm. Sci.* Vol. 66, pp. 1-19.

For example, if COMPOUND 2 is anionic, or has a functional group which may be anionic (e.g., —NH— may be —N—⁻), then a salt may be formed with a suitable cation. Examples of suitable inorganic cations include, but are not limited to, alkali metal ions such as $Na^+$ and $K^+$, alkaline earth cations such as $Ca^{2+}$ and $Mg^{2+}$, and other cations such as $Al^{3+}$. Examples of some suitable substituted ammonium ions are those derived from: ethylamine, diethylamine, dicyclohexylamine, triethylamine, butylamine, ethylenediamine, ethanolamine, diethanolamine, piperazine, benzylamine, phenylbenzylamine, choline, meglumine, and tromethamine, as well as amino acids, such as lysine and arginine. An example of a common quaternary ammonium ion is $N(CH_3)_4^+$.

If COMPOUND 2 is cationic, or has a functional group that may be cationic (e.g., —NHR may be —NH₂R⁺), then a salt may be formed with a suitable anion. Examples of suitable inorganic anions include, but are not limited to, those derived from the following inorganic acids: hydrochloric, hydrobromic, hydroiodic, sulfuric, sulfurous, nitric, nitrous, phosphoric, and phosphorous.

Examples of suitable organic anions include, but are not limited to, those derived from the following organic acids: 2-acetyoxybenzoic, acetic, ascorbic, aspartic, benzoic, camphorsulfonic, cinnamic, citric, edetic, ethanedisulfonic, ethanesulfonic, fumaric, glucoheptonic, gluconic, glutamic, glycolic, hydroxymaleic, hydroxynaphthalene carboxylic, isethionic, lactic, lactobionic, lauric, maleic, malic, methanesulfonic, mucic, oleic, oxalic, palmitic, pamoic, pantothenic, phenylacetic, phenylsulfonic, propionic, pyruvic, salicylic, stearic, succinic, sulfanilic, tartaric, toluenesulfonic, and valeric. Examples of suitable polymeric organic anions include, but are not limited to, those derived from the following polymeric acids: tannic acid, carboxymethyl cellulose.

COMPOUND 2 for use in the methods and pharmaceutical compositions provided herein therefore includes COMPOUND 2 itself, as well as its pharmaceutically acceptable salts, solvates, tautomers, stereoisomers, isotopologues, prodrugs or polymorphs. COMPOUND 2 provided herein may be modified and converted to a prodrug by appending appropriate functionalities to enhance selected biological properties, e.g., targeting to a particular tissue. Such modifications (i.e., prodrugs) are known in the art and include those which increase biological penetration into a given biological compartment (e.g., blood, lymphatic system, central nervous system), increase oral availability, increase solubility to allow administration by injection, alter metabolism and alter rate of excretion. Examples of prodrugs include esters (e.g., phosphates, amino acid (e.g., valine) esters), carbamates and other pharmaceutically acceptable derivatives, which, upon administration to a subject, are capable of providing active compounds.

It has been found that COMPOUND 2 can exist in a variety of solid forms. In one embodiment, provided herein are solid forms that include neat crystal forms. In another embodiment, provided herein are solid forms that include solvated forms and amorphous forms. The present disclosure provides certain solid forms of COMPOUND 2. In certain embodiments, the present disclosure provides compositions comprising COMPOUND 2 in a form described herein. In some embodiments of provided compositions, COMPOUND 2 is present as a mixture of one or more solid forms; in some embodiments of provided compositions, COMPOUND 2 is present in a single form.

In one embodiment, COMPOUND 2 is a single crystalline form, or any one of the single crystalline forms described herein. Synthesis of crystalline forms of COMPOUND 2 is described in international application publications WO 2015/138837 and WO 2015/138839, both published Sep. 17, 2015, both incorporated by reference herein in their entireties. Also provided are pharmaceutical compositions comprising at least one pharmaceutically acceptable carrier or diluent; and COMPOUND 2, wherein COMPOUND 2 is a single crystalline form, or any one of the crystalline forms being described herein. Also provided are uses of COMPOUND 2, wherein COMPOUND 2 is a single crystalline form, or any one of the single crystalline forms described herein, to prepare a pharmaceutical composition.

Provided herein is an assortment of characterizing information to describe the crystalline forms of COMPOUND 2. It should be understood, however, that not all such information is required for one skilled in the art to determine that such particular form is present in a given composition, but that the determination of a particular form can be achieved using any portion of the characterizing information that one skilled in the art would recognize as sufficient for establishing the presence of a particular form, e.g., even a single distinguishing peak can be sufficient for one skilled in the art to appreciate that such particular form is present.

In one embodiment, at least a particular percentage by weight of COMPOUND 2 is crystalline. Particular weight percentages may be 10%, 20%, 30%, 40%, 50%, 60%, 70%, 75%, 80%, 85%, 87%, 88%, 89%, 90%, 91%, 92%, 93%, 94%, 95%, 96%, 97%, 98%, 99%, 99.5%, 99.9%, or any percentage between 10% and 100%. When a particular percentage by weight of COMPOUND 2 is crystalline, the remainder of COMPOUND 2 is the amorphous form of COMPOUND 2. Non-limiting examples of crystalline COMPOUND 2 include a single crystalline form of compound 1 or a mixture of different single crystalline forms. In some embodiments, COMPOUND 2 is at least 90% by weight crystalline. In some other embodiments, COMPOUND 2 is at least 95% by weight crystalline.

In another embodiment, a particular percentage by weight of the crystalline COMPOUND 2 is a specific single crystalline form or a combination of single crystalline forms. Particular weight percentages may be 10%, 20%, 30%, 40%, 50%, 60%, 70%, 75%, 80%, 85%, 87%, 88%, 89%, 90%, 91%, 92%, 93%, 94%, 95%, 96%, 97%, 98%, 99%, 99.5%, 99.9%, or any percentage between 10% and 100%. In another embodiment, COMPOUND 2 is at least 90% by weight of a single crystalline form. In another embodiment, COMPOUND 2 is at least 95% by weight of a single crystalline form.

In the following description of COMPOUND 2, embodiments of the invention may be described with reference to a particular crystalline form of COMPOUND 2, as characterized by one or more properties as discussed herein. The descriptions characterizing the crystalline forms may also be used to describe the mixture of different crystalline forms that may be present in a crystalline COMPOUND 2. However, the particular crystalline forms of COMPOUND 2 may also be characterized by one or more of the characteristics of the crystalline form as described herein, with or without regard to referencing a particular crystalline form.

The crystalline forms are further illustrated by the detailed descriptions and illustrative examples given below. The XRPD peaks described in Tables 1 to 2 may vary by ±0.2° depending upon the instrument used to obtain the data. The intensity of the XRPD peaks described in Tables 1 to 2 may vary by 10%.

Form 1

Figure 5:
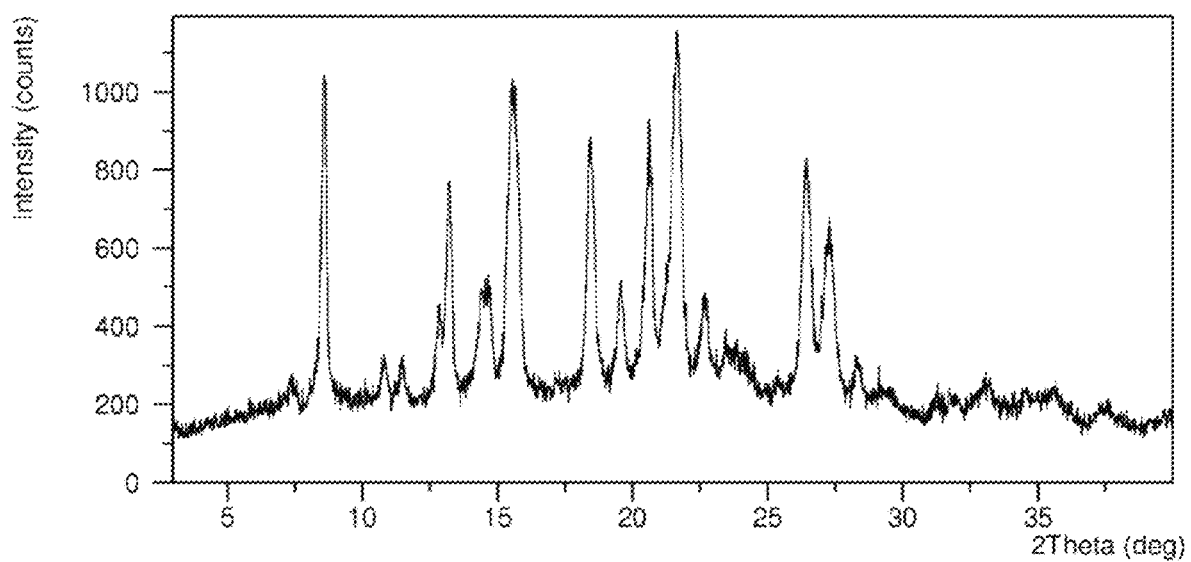
FIG. 5 is an X-ray powder diffractogram (XPRD) of COMPOUND 2 form 1.

In one embodiment, a single crystalline form, Form 1, of COMPOUND 2 is characterized by the X-ray powder diffraction (XRPD) pattern shown in FIG. 5, and data shown in Table 1, obtained using CuKa radiation. In a particular embodiment, the polymorph can be characterized by one or more of the peaks taken from FIG. 5, as shown in Table 1. For example, the polymorph can be characterized by one or two or three or four or five or six or seven or eight or nine of the peaks shown in Table 1.

TABLE 1

| Angle 2-Theta° | Intensity % |
|---|---|
| 8.6 | 90.3 |
| 13.2 | 60.0 |
| 15.6 | 85.5 |
| 18.5 | 72.5 |
| 19.6 | 31.5 |
| 20.6 | 71.6 |
| 21.6 | 100.0 |
| 26.4 | 64.2 |
| 27.3 | 45.6 |

In another embodiment, Form 1 can be characterized by the peaks identified at 2θ angles of 8.6, 15.6, 18.5, 20.6, 21.6, and 26.4°. In another embodiment, Form 1 can be characterized by the peaks identified at 2θ angles of 8.6, 15.6, 18.5, and 21.6°.

Figure 6:
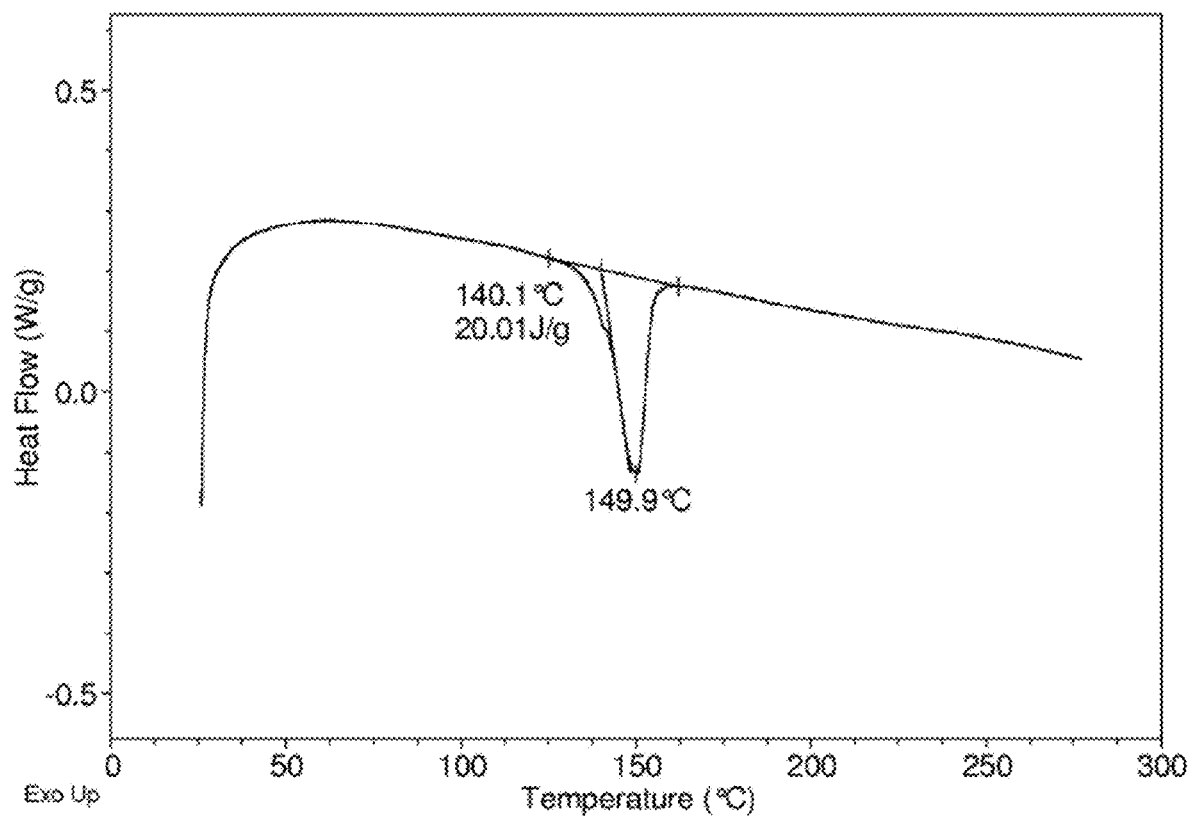
FIG. 6 is a differential scanning calorimetry (DSC) profile of COMPOUND 2 form 1.

In another embodiment, Form 1 can be characterized by the differential scanning calorimetry profile (DSC) shown in FIG. 6. The DSC graph plots the heat flow as a function of temperature from a sample, the temperature rate change being about 10° C./min. The profile is characterized by an endothermic transition with an onset temperature of about 140.1° C. with a melt at about 149.9° C.

Figure 7:
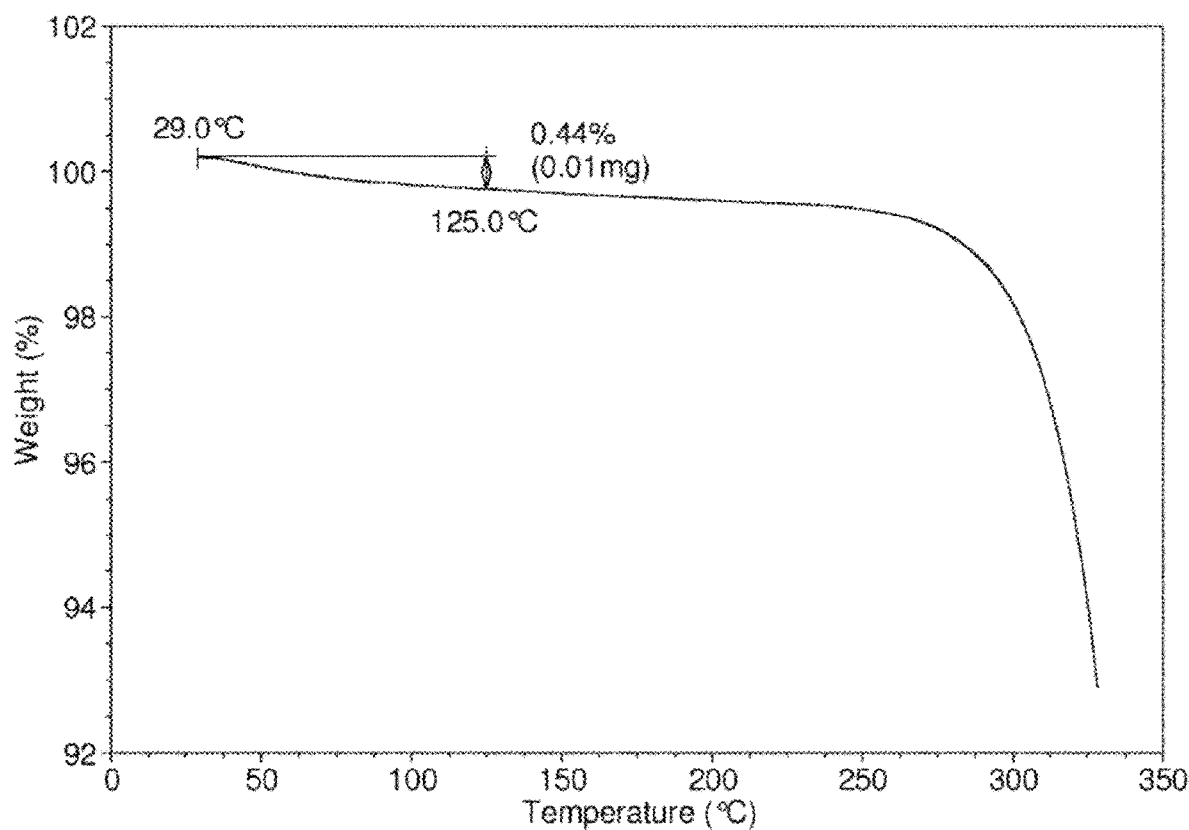
FIG. 7 is a thermal gravimetric analysis (TGA) profile of COMPOUND 2 form 1.

In another embodiment, Form 1 can be characterized by thermal gravimetric analysis (TGA) shown in FIG. 7. The TGA profile graphs the percent loss of weight of the sample as a function of temperature, the temperature rate change being about 10° C./min. The weight loss represents a loss of about 0.44% of the weight of the sample as the temperature is changed from about 29.0° C. to 125.0° C.

Form 2

Figure 8:
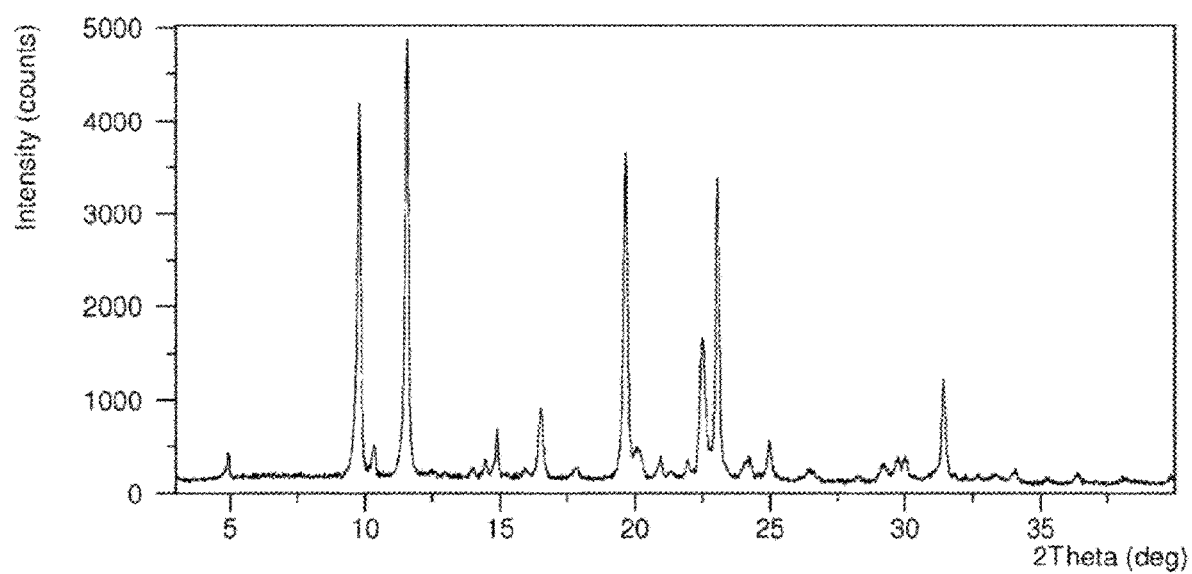
FIG. 8 is an X-ray powder diffractogram (XPRD) of COMPOUND 2 form 2.

In one embodiment, a single crystalline form, Form 2, of the COMPOUND 2 is characterized by the X-ray powder diffraction (XRPD) pattern shown in FIG. 8, and data shown in Table 2, obtained using CuKa radiation. In a particular embodiment, the polymorph can be characterized by one or more of the peaks taken from FIG. 8, as shown in Table 2. For example, the polymorph can be characterized by one or two or three or four or five or six or seven or eight or nine or ten of the peaks shown in Table 2.

TABLE 2

| Angle 2-Theta° | Intensity % |
|---|---|
| 9.8 | 85.6 |
| 11.6 | 100.0 |
| 14.9 | 11.4 |
| 16.5 | 15.3 |
| 19.6 | 75.2 |
| 20.1 | 7.3 |
| 22.5 | 32.6 |
| 23.0 | 69.4 |
| 25.0 | 8.9 |
| 31.4 | 22.0 |

In another embodiment, Form 2 can be characterized by the peaks identified at 2θ angles of 9.8, 11.6, 19.6, 22.5, 23.0, and 31.4°. In another embodiment, Form 2 can be characterized by the peaks identified at 2θ angles of 9.8, 11.6, 19.6, and 23.0°.

Figure 9:
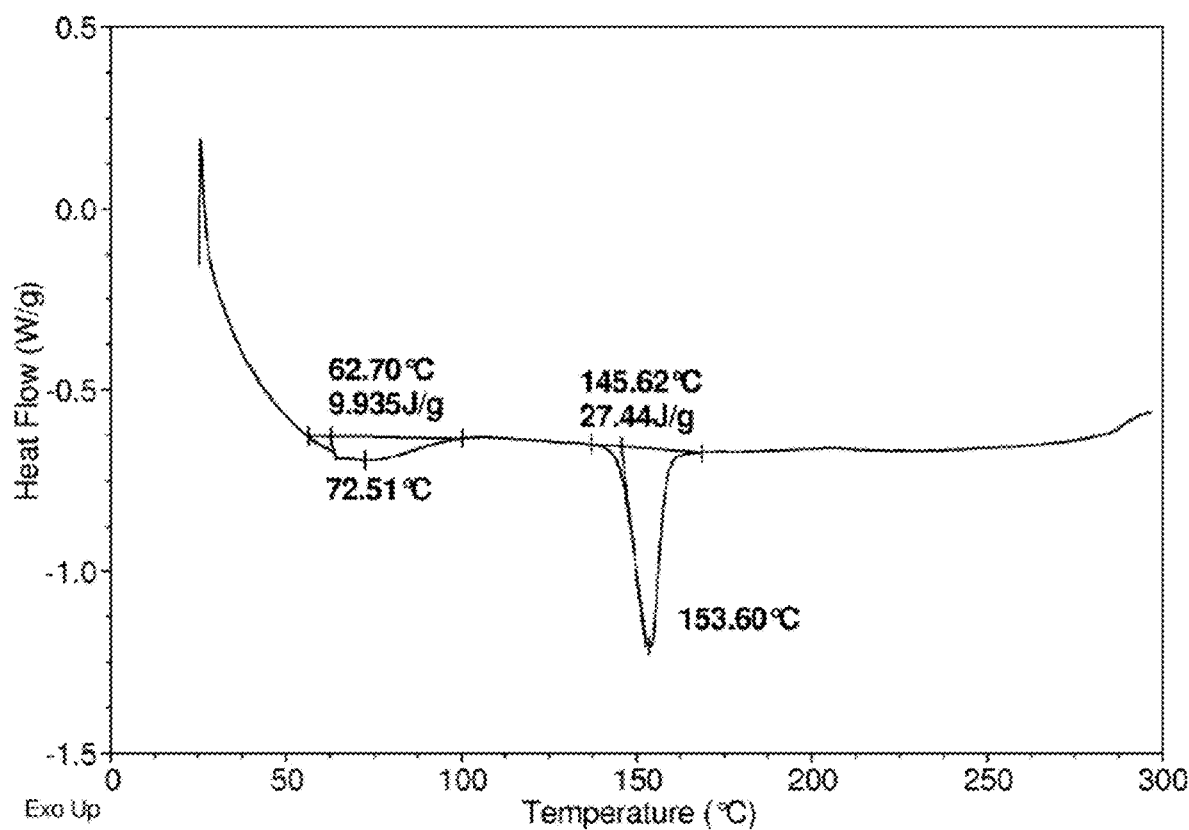
FIG. 9 is a differential scanning calorimetry (DSC) profile of COMPOUND 2 form 2.

In another embodiment, Form 2 can be characterized by the differential scanning calorimetry profile (DSC) shown in FIG. 9. The DSC graph plots the heat flow as a function of temperature from a sample, the temperature rate change being about 10° C./min. The profile is characterized by an endothermic transition with an onset temperature of about 62.7° C. with a melt at about 72.5° C., and an endothermic transition with an onset temperature of about 145.6° C. with a melt at about 153.6° C.

Figure 10:
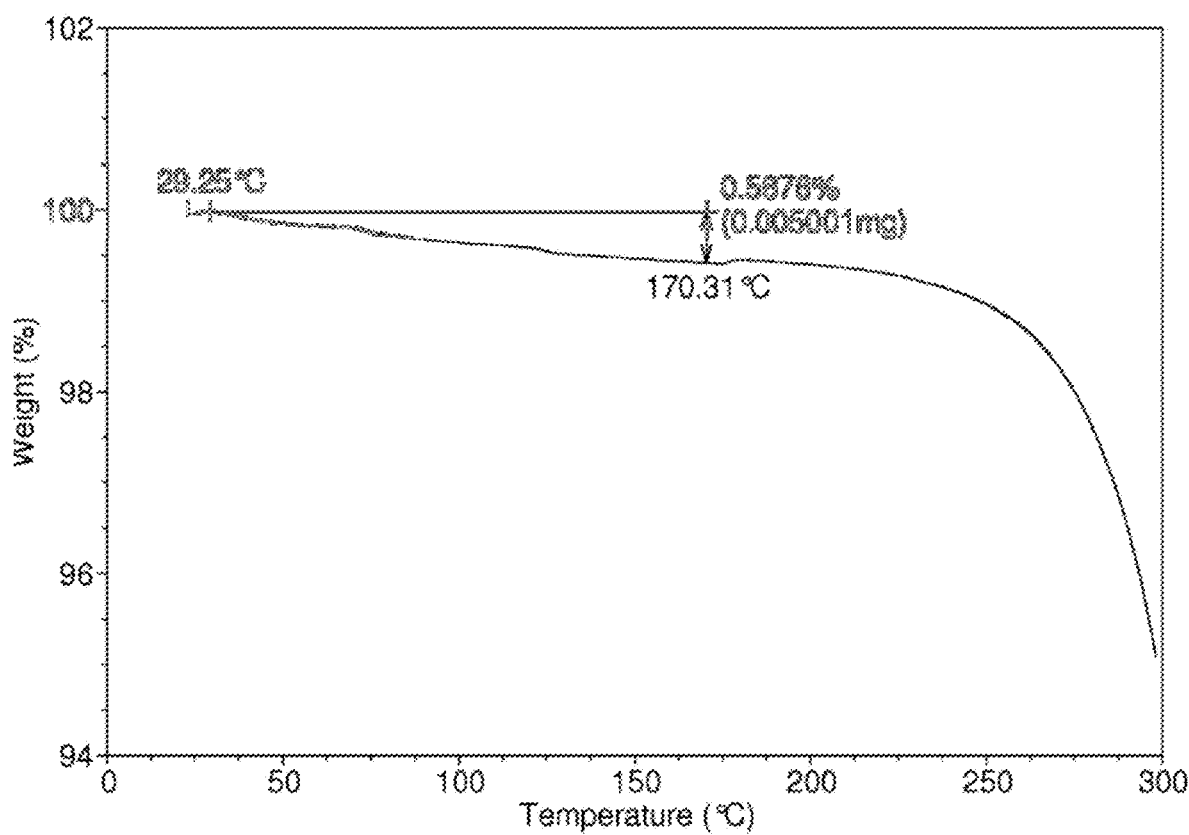
FIG. 10 is a thermal gravimetric analysis (TGA) profile of COMPOUND 2 form 2.

In another embodiment, Form 2 can be characterized by thermal gravimetric analysis (TGA) shown in FIG. 10. The TGA profile graphs the percent loss of weight of the sample as a function of temperature, the temperature rate change being about 10° C./min. The weight loss represents a loss of about 0.57% of the weight of the sample as the temperature is changed from about 29.3° C. to 170.3° C.

Other embodiments are directed to a single crystalline form of COMPOUND 2 characterized by a combination of the aforementioned characteristics of any of the single crystalline forms discussed herein. The characterization may be by any combination of one or more of the XRPD, TGA, and DSC described for a particular polymorph. For example, the single crystalline form of COMPOUND 2 may be characterized by any combination of the XRPD results regarding the position of the major peaks in a XRPD scan; and/or any combination of one or more of parameters derived from data obtained from a XRPD scan. The single crystalline form of COMPOUND 2 may also be characterized by TGA determinations of the weight loss associated with a sample over a designated temperature range; and/or the temperature at which a particular weight loss transition begins. DSC determinations of the temperature associated with the maximum heat flow during a heat flow transition and/or the temperature at which a sample begins to undergo a heat flow transition may also characterize the crystalline form. Weight change in a sample and/or change in sorption/desorption of water per molecule of COMPOUND 2 as determined by water sorption/desorption measurements over a range of relative humidity (e.g., 0% to 90%) may also characterize a single crystalline form of COMPOUND 2.

DNA Demethylating Agents

In one embodiment, the methods provided herein comprise administration or co-administration of one or more DNA demethylating agents. In one embodiment, the DNA demethylating agents are cytidine analogs. In certain embodiments, the cytidine analog is azacitidine) or 5-aza-2'-deoxycytidine (decitabine). In certain embodiments, the cytidine analog is azacitidine. In certain embodiments, the cytidine analog is 5-aza-2'-deoxycytidine (decitabine). In certain embodiments, the cytidine analog is, for example: 1-β-D-arabinofuranosylcytosine (Cytarabine or ara-C); pseudoiso-cytidine (psi ICR); 5-fluoro-2'-deoxycytidine (FCdR); 2'-deoxy-2',2'-difluorocytidine (Gemcitabine); 5-aza-2'-deoxy-2',2'-difluorocytidine; 5-aza-2'-deoxy-2'-fluorocytidine; 1-β-D-ribofuranosyl-2(1H)-pyrimidinone (Zebularine); 2',3'-dideoxy-5-fluoro-3'-thiacytidine (Emtriva); 2'-cyclocytidine (Ancitabine); 1-β-D-arabinofuranosyl-5-azacytosine (Fazarabine or ara-AC); 6-azacitidine (6-aza-CR); 5,6-dihydro-5-azacitidine (dH-aza-CR); $N^4$-pentyloxy-carbonyl-5'-deoxy-5-fluorocytidine (Capecitabine); $N^4$-octadecyl-cytarabine; or elaidic acid cytarabine. In certain embodiments, the cytidine analogs include any compound which is structurally related to cytidine or deoxycytidine and functionally mimics and/or antagonizes the action of cytidine or deoxycytidine.

In certain embodiments, exemplary cytidine analogs have the structures provided below:

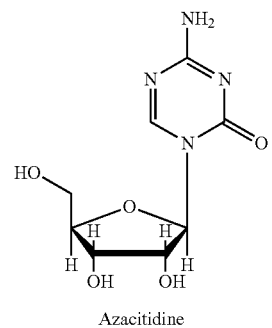

Azacitidine

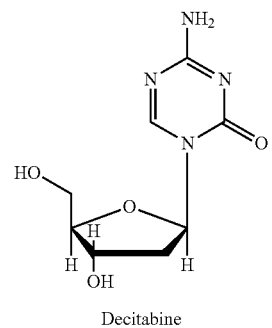

Decitabine

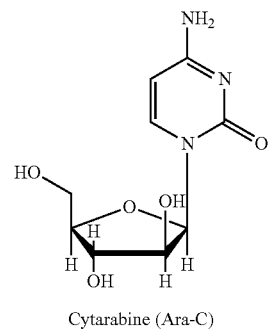

Cytarabine (Ara-C)

-continued

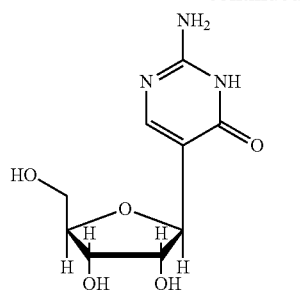

Pseudoisocytidine (psi ICR)

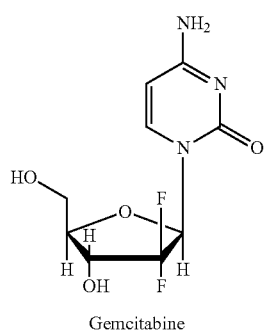

Gemcitabine

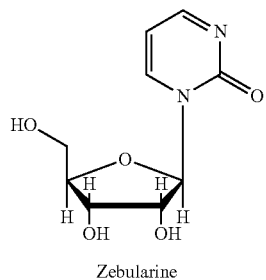

Zebularine

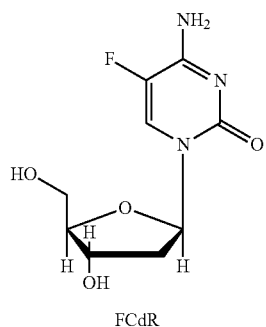

FCdR

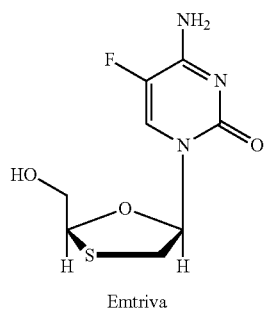

Emtriva

-continued

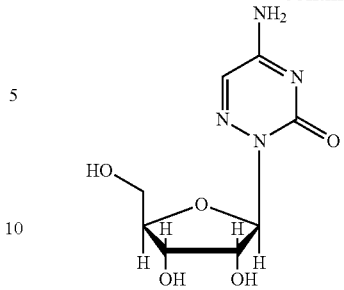

6-Azacytidine

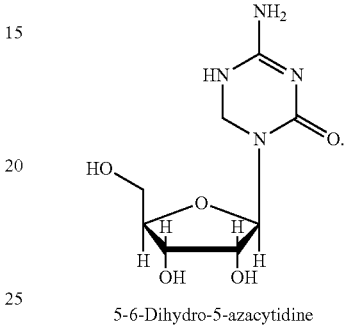

5-6-Dihydro-5-azacytidine

Cytidine analogs for use in the methods provided herein may be prepared using synthetic methods and procedures referenced herein or otherwise available in the literature. For example, particular methods for synthesizing azacitidine and decitabine are disclosed, e.g., in U.S. Pat. No. 7,038,038 and references discussed therein, each of which is incorporated herein by reference. Other cytidine analogs for use in the methods provided herein may be prepared, e.g., using procedures known in the art, or may be purchased from a commercial source. In one embodiment, the cytidine analogs for use in the methods provided herein may be prepared in a particular solid form (e.g., amorphous or crystalline form). See, e.g., U.S. Pat. No. 6,887,855, issued May 8, 2005 and U.S. Pat. No. 6,943,249, issued Sep. 13, 2005, both of which are incorporated herein by reference in their entireties.

In one embodiment, the cytidine analog used in the methods provided herein is a free base, or a pharmaceutically acceptable salt or solvate thereof. In one embodiment, the free base or the pharmaceutically acceptable salt or solvate is a solid. In another embodiment, the free base or the pharmaceutically acceptable salt or solvate is a solid in an amorphous form. In yet another embodiment, the free base or the pharmaceutically acceptable salt or solvate is a solid in a crystalline form. For example, particular embodiments provide azacitidine and decitabine in solid forms, which can be prepared, for example, according to the methods described in U.S. Pat. Nos. 6,887,855; 6,943,249; 7,038,038; 7,078,518; 7,192,781; 7,772,199 and U.S. Patent Application Publication Nos. 2005/027675, each of which is incorporated by reference herein in their entireties. In other embodiments, azacitidine and decitabine in solid forms can be prepared using other methods known in the art.

In one embodiment, cytidine analog used in the methods provided herein is a pharmaceutically acceptable salt of the cytidine analog, which includes, but is not limited to, acetate, adipate, alginate, aspartate, benzoate, benzenesulfonate (besylate), bisulfate, butyrate, citrate, camphorate, camphorsulfonate, cyclopentanepropionate, digluconate, dodecylsulfate, 1,2-ethanedisulfonate (edisylate), ethanesulfonate (esylate), formate, fumarate, glucoheptanoate, glycerophosphate, glycolate, hemisulfate, heptanoate, hexanoate, hydrochloride, hydrobromide, hydroiodide, 2-hydroxyethanesulfonate, lactate, maleate, malonate, methanesulfonate (mesylate), 2-naphthalenesulfonate (napsylate), nicotinate, nitrate, oxalate, palmoate, pectinate, persulfate, 3-phenylpropionate, phosphate, picrate, pivalate, propionate, salicylate, succinate, sulfate, tartrate, thiocyanate, tosylate, or undecanoate salts.

Azacitidine is 4-amino-1-β-D-ribofuranozyl-s-triazin-2(1H)-one, also known as VIDAZA® (Celgene Corporation). Its empirical formula is $C_8H_{12}N_4O_5$, the molecular weight is 244. Azacitidine is a white to off-white solid that is insoluble in acetone, ethanol and methyl ketone; slightly soluble in ethanol/water (50/50), propylene glycol and polyethylene glycol; sparingly soluble in water, water-saturated octanol, 5% dextrose in water, N-methyl-2-pyrrolidone, normal saline and 5% Tween 80 in water, and soluble in dimethylsulfoxide (DMSO).

VIDAZA® is approved for treatment in patients with higher-risk MDS. It is supplied in a sterile form for reconstitution as a suspension for subcutaneous injection or reconstitution as a solution with further dilution for intravenous infusion. Vials of VIDAZA® contain 100 mg of azacitidine and 100 mg of mannitol as a sterile lyophilized powder. The approved dosing schedule is a twice-daily subcutaneous injection or a single daily intravenous infusion on seven consecutive days of a 28-day treatment cycle.

Oral azacitidine is effective and safe in lower-risk myelodisplastic syndrome (MDS) and acute myeloid leukemia (AML) patients. In one embodiment, the dose used in MDS and AML patients is 300 mg once daily based on extended dosing (14 or 21 days of the 28-day treatment cycle). In one embodiment, the starting dose for oral azacitidine is 120 mg and the maximum tolerated dose is 480 mg.

Decitabine is 4-amino-1-(2-deoxy-β-D-erythro-pentofuranosyl)-1,3,5-triazin-2(1H)one, also known as DACOGEN®. Its empirical formula is $C_8H_{12}N_4O_4$, the molecular weight is 228.21. Decitabine is a fine, white to almost white powder that is slightly soluble in ethanol/water (50/50), methanol/water (50/50) and methanol; sparingly soluble in water, and soluble in dimethylsulfoxide (DMSO).

DACOGEN™ is approved for treatment in patients with myelodisplastic syndromes. It is supplied in a clear colorless glass vial as white sterile lyophilized powder for injection. Each 20 mL, as a single dose, glass vial contains 50 mg decitabine, 68 mg monobasic potassium phosphate (potassium dihydrogen phosphate) and 11.6 mg sodium hydrochloride.

Compositions and Routes of Administration

In one embodiment, provided herein is a pharmaceutical composition comprising a therapeutically effective amount of a mutant IDH1 inhibitor and a DNA demethylating agent. In one embodiment, the mutant IDH1 inhibitor is COMPOUND 2.

In one embodiment, provided herein is a pharmaceutical composition comprising a therapeutically effective amount of COMPOUND 2 and azacitidine.

In one embodiment, COMPOUND 2 and azacitidine are formulated as one composition. In another embodiment, COMPOUND 2 and azacitidine are formulated as separate compositions.

In one embodiment, the compounds utilized in the methods provided herein may be formulated together with a pharmaceutically acceptable carrier or adjuvant into pharmaceutically acceptable compositions prior to be administered to a subject. In another embodiment, such pharmaceutically acceptable compositions further comprise additional therapeutic agents in amounts effective for achieving a modulation of disease or disease symptoms, including those described herein.

Pharmaceutically acceptable carriers, adjuvants and vehicles that may be used in the pharmaceutical compositions of one aspect of this invention include, but are not limited to, ion exchangers, alumina, aluminum stearate, lecithin, self-emulsifying drug delivery systems (SEDDS) such as d-α-tocopherol polyethyleneglycol 1000 succinate, surfactants used in pharmaceutical dosage forms such as Tweens or other similar polymeric delivery matrices, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat. Cyclodextrins such as α-, β-, and γ-cyclodextrin, or chemically modified derivatives such as hydroxyalkylcyclodextrins, including 2- and 3-hydroxypropyl-β-cyclodextrins, or other solubilized derivatives may also be advantageously used to enhance delivery of COMPOUND 2 described herein.

In one embodiment, the pharmaceutical composition comprises COMPOUND 2 and an excipient. In one embodiment, the pharmaceutical composition that comprises COMPOUND 2 and an excipient, is for oral administration. In one embodiment, the excipient is a diluent, a binder, a disintegrant, a wetting agent, a stabilizer, a glidant, or a lubricant.

In one embodiment, the pharmaceutical composition comprises COMPOUND 2 and/or azacitidine and an excipient. In one embodiment, the pharmaceutical composition that comprises COMPOUND 2 and/or azacitidine and an excipient, is for oral administration.

Oral delivery formats for COMPOUND 2 and/or azacitidine include, but are not limited to, tablets, capsules, caplets, solutions, suspensions, and syrups, and may also comprise a plurality of granules, beads, powders or pellets that may or may not be encapsulated. Such formats may also be referred to herein as the "drug core" which contains COMPOUND 2 and/or azacitidine.

Particular embodiments herein provide solid oral dosage forms that are tablets or capsules. In certain embodiments, the formulation is a tablet comprising COMPOUND 2 and/or azacitidine. In certain embodiments, the formulation is a capsule comprising COMPOUND 2 and/or azacitidine. In certain embodiments, the tablets or capsules provided herein optionally comprise one or more excipients, such as, for example, glidants, diluents, lubricants, colorants, disintegrants, granulating agents, binding agents, polymers, and coating agents. In certain embodiments, the formulation is an immediate release tablet. In certain embodiments, the formulation is a controlled release tablet releasing the active pharmaceutical ingredient (API), e.g., substantially in the stomach. In certain embodiments, the formulation is a hard gelatin capsule. In certain embodiments, the formulation is a soft gelatin capsule. In certain embodiments, the capsule is a hydroxypropyl methylcellulose (HPMC) capsule. In certain embodiments, the formulation is an immediate release capsule. In certain embodiments, the formulation is an immediate or controlled release capsule releasing the API, e.g., substantially in the stomach. In certain embodiments, the formulation is a rapidly disintegrating tablet that dissolves substantially in the mouth following administration. In certain embodiments, embodiments herein encompass the use of COMPOUND 2 and/or azacitidine for the preparation of a pharmaceutical composition for treating a malignancy, characterized by the presence of a mutant allele of IDH1, wherein the composition is prepared for oral administration.

Particular embodiments herein provide pharmaceutical formulations (e.g., immediate release oral formulations and/or formulations that release the API substantially in the stomach) comprising COMPOUND 2 and/or azacitidine that achieve a particular AUC value (e.g., AUC(0-t) or AUC(0-∞)) in the subject (e.g., human) to which the formulation is orally administered. Particular embodiments provide oral formulations that achieve an AUC value of at least about 25 ng-hr/mL, at least about 50 ng-hr/mL, at least about 75 ng-hr/mL, at least about 100 ng-hr/mL, at least about 150 ng-hr/mL, at least about 200 ng-hr/mL, at least about 250 ng-hr/mL, at least about 300 ng-hr/mL, at least about 350 ng-hr/mL, at least about 400 ng-hr/mL, at least about 450 ng-hr/mL, at least about 500 ng-hr/mL, at least about 550 ng-hr/mL, at least about 600 ng-hr/mL, at least about 650 ng-hr/mL, at least about 700 ng-hr/mL, at least about 750 ng-hr/mL, at least about 800 ng-hr/mL, at least about 850 ng-hr/mL, at least about 900 ng-hr/mL, at least about 950 ng-hr/mL, at least about 1000 ng-hr/mL, at least about 1100 ng-hr/mL, at least about 1200 ng-hr/mL, at least about 1300 ng-hr/mL, at least about 1400 ng-hr/mL, at least about 1500 ng-hr/mL, at least about 1600 ng-hr/mL, at least about 1700 ng-hr/mL, at least about 1800 ng-hr/mL, at least about 1900 ng-hr/mL, at least about 2000 ng-hr/mL, at least about 2250 ng-hr/mL, or at least about 2500 ng-hr/mL. In particular embodiments, the AUC determination is obtained from a time-concentration pharmacokinetic profile obtained from the blood samples of animals or human volunteers following dosing.

Particular embodiments herein provide pharmaceutical formulations (e.g., immediate release oral formulations and/or formulations that release the API substantially in the stomach) comprising COMPOUND 2 and/or azacitidine that achieve a particular maximum plasma concentration ("Cmax") in the subject to which the formulation is orally administered. Particular embodiments provide oral formulations that achieve a Cmax of the COMPOUND 2 and/or citidine analog of at least about 25 ng/mL, at least about 50 ng/mL, at least about 75 ng/mL, at least about 100 ng/mL, at least about 150 ng/mL, at least about 200 ng/mL, at least about 250 ng/mL, at least about 300 ng/mL, at least about 350 ng/mL, at least about 400 ng/mL, at least about 450 ng/mL, at least about 500 ng/mL, at least about 550 ng/mL, at least about 600 ng/mL, at least about 650 ng/mL, at least about 700 ng/mL, at least about 750 ng/mL, at least about 800 ng/mL, at least about 850 ng/mL, at least about 900 ng/mL, at least about 950 ng/mL, at least about 1000 ng/mL, at least about 1100 ng/mL, at least about 1200 ng/mL, at least about 1300 ng/mL, at least about 1400 ng/mL, at least about 1500 ng/mL, at least about 1600 ng/mL, at least about 1700 ng/mL, at least about 1800 ng/mL, at least about 1900 ng/mL, at least about 2000 ng/mL, at least about 2250 ng/mL, or at least about 2500 ng/mL.

Particular embodiments herein provide pharmaceutical formulations (e.g., immediate release oral formulations and/or formulations that release the API substantially in the stomach) comprising COMPOUND 2 and/or azacitidine that achieve a particular time to maximum plasma concentration ("Tmax") in the subject to which the formulation is orally administered. Particular embodiments provide oral formulations that achieve a Tmax of the cytidine analog of less than about 10 min., less than about 15 min., less than about 20 min., less than about 25 min., less than about 30 min., less than about 35 min., less than about 40 min., less than about 45 min., less than about 50 min., less than about 55 min., less than about 60 min., less than about 65 min., less than about 70 min., less than about 75 min., less than about 80 min., less than about 85 min., less than about 90 min., less than about 95 min., less than about 100 min., less than about 105 min., less than about 110 min., less than about 115 min., less than about 120 min., less than about 130 min., less than about 140 min., less than about 150 min., less than about 160 min., less than about 170 min., less than about 180 min., less than about 190 min., less than about 200 min., less than about 210 min., less than about 220 min., less than about 230 min., or less than about 240 min. In particular embodiments, the Tmax value is measured from the time at which the formulation is orally administered.

Particular embodiments herein provide oral dosage forms comprising COMPOUND 2 and/or azacitidine wherein the oral dosage forms have an enteric coating. Particular embodiments provide a permeable or partly permeable (e.g., "leaky") enteric coating with pores. In particular embodiments, the permeable or partly permeable enteric-coated tablet releases the COMPOUND 2 and/or azacitidine in an immediate release manner substantially in the stomach.

Provided herein are dosage forms designed to maximize the absorption and/or efficacious delivery of COMPOUND 2 and/or azacytidine, upon oral administration, e.g., for release substantially in the stomach. Accordingly, certain embodiments herein provide a solid oral dosage form of COMPOUND 2 and/or azacitidine using pharmaceutical excipients designed for immediate release of the API upon oral administration, e.g., substantially in the stomach. Particular immediate release formulations comprise a specific amount of COMPOUND 2 and/or azacitidine and optionally one or more excipients. In certain embodiments, the formulation may be an immediate release tablet or an immediate release capsule (such as, e.g., an HPMC capsule).

Provided herein are methods of making the formulations provided herein comprising COMPOUND 2 and/or azacitidine provided herein (e.g., immediate release oral formulations and/or formulations that release the API substantially in the stomach). In particular embodiments, the formulations provided herein may be prepared using conventional methods known to those skilled in the field of pharmaceutical formulation, as described, e.g., in pertinent textbooks. See, e.g., REMINGTON, THE SCIENCE AND PRACTICE OF PHARMACY, 20th Edition, Lippincott Williams & Wilkins, (2000); ANSEL et al., PHARMACEUTICAL DOSAGE FORMS AND DRUG DELIVERY SYSTEMS, 7th Edition, Lippincott Williams & Wilkins, (1999); GIBSON, PHARMACEUTICAL PREFORMULATION AND FORMULATION, CRC Press (2001).

In particular embodiments, formulations provided herein (e.g., immediate release oral formulations, formulations that release the API substantially in the stomach, or rapidly disintegrating formulations that dissolve substantially in the mouth) comprise COMPOUND 2 and/or azacitidine in a specific amount. In particular embodiments, the specific amount of COMPOUND 2 and/or azacitidine in the formulation is, e.g., about 10 mg. In one embodiment, the specific amount is about 20 mg. In one embodiment, the specific amount is about 40 mg. In one embodiment, the specific amount is about 60 mg. In one embodiment, the specific amount is about 80 mg. In one embodiment, the specific amount is about 100 mg. In one embodiment, the specific amount is about 120 mg. In one embodiment, the specific amount is about 140 mg. In one embodiment, the specific amount is about 160 mg. In one embodiment, the specific amount is about 180 mg. In one embodiment, the specific amount is about 200 mg. In one embodiment, the specific amount is about 220 mg. In one embodiment, the specific amount is about 240 mg. In one embodiment, the specific amount is about 260 mg. In one embodiment, the specific amount is about 280 mg. In one embodiment, the specific amount is about 300 mg. In one embodiment, the specific amount is about 320 mg. In one embodiment, the specific amount is about 340 mg. In one embodiment, the specific amount is about 360 mg. In one embodiment, the specific amount is about 380 mg. In one embodiment, the specific amount is about 400 mg. In one embodiment, the specific amount is about 420 mg. In one embodiment, the specific amount is about 440 mg. In one embodiment, the specific amount is about 460 mg. In one embodiment, the specific amount is about 480 mg. In one embodiment, the specific amount is about 500 mg. In one embodiment, the specific amount is about 600 mg. In one embodiment, the specific amount is about 700 mg. In one embodiment, the specific amount is about 800 mg. In one embodiment, the specific amount is about 900 mg. In one embodiment, the specific amount is about 1000 mg. In one embodiment, the specific amount is about 1100 mg. In one embodiment, the specific amount is about 1200 mg. In one embodiment, the specific amount is about 1300 mg. In one embodiment, the specific amount is about 1400 mg. In one embodiment, the specific amount is about 1500 mg. In one embodiment, the specific amount is about 1600 mg. In one embodiment, the specific amount is about 1700 mg. In one embodiment, the specific amount is about 1800 mg. In one embodiment, the specific amount is about 1900 mg. In one embodiment, the specific amount is about 2000 mg. In one embodiment, the specific amount is about 2100 mg. In one embodiment, the specific amount is about 2200 mg. In one embodiment, the specific amount is about 2300 mg. In one embodiment, the specific amount is about 2400 mg. In one embodiment, the specific amount is about 2500 mg. In one embodiment, the specific amount is about 3000 mg. In one embodiment, the specific amount is about 4000 mg. In one embodiment, the specific amount is about 5000 mg.

In certain embodiments, the formulation is a tablet, wherein the tablet is manufactured using standard, art-recognized tablet processing procedures and equipment. In certain embodiments, the method for forming the tablets is direct compression of a powdered, crystalline and/or granular composition comprising COMPOUND 2 and/or azacitidine alone or in combination with one or more excipients, such as, for example, carriers, additives, polymers, or the like. In certain embodiments, as an alternative to direct compression, the tablets may be prepared using wet granulation or dry granulation processes. In certain embodiments, the tablets are molded rather than compressed, starting with a moist or otherwise tractable material. In certain embodiments, compression and granulation techniques are used.

In certain embodiments, the formulation is a capsule, wherein the capsules may be manufactured using standard, art-recognized capsule processing procedures and equipments. In certain embodiments, soft gelatin capsules may be prepared in which the capsules contain a mixture of COMPOUND 2 and/or the cytidine analog and vegetable oil or non-aqueous, water miscible materials such as, for example, polyethylene glycol and the like. In certain embodiments, hard gelatin capsules may be prepared containing granules of COMPOUND 2 and/or the cytidine analog in combination with a solid pulverulent carrier, such as, for example, lactose, saccharose, sorbitol, mannitol, potato starch, corn starch, amylopectin, cellulose derivatives, or gelatin. In certain embodiments, a hard gelatin capsule shell may be prepared from a capsule composition comprising gelatin and a small amount of plasticizer such as glycerol. In certain embodiments, as an alternative to gelatin, the capsule shell may be made of a carbohydrate material. In certain embodiments, the capsule composition may additionally include polymers, colorings, flavorings and opacifiers as required. In certain embodiments, the capsule comprises HPMC.

In certain embodiments, the formulation of COMPOUND 2 and/or azacitidine is prepared using aqueous solvents without causing significant hydrolytic degradation of azacitidine. In particular embodiments, the formulation of COMPOUND 2 and/or azacitidine is a tablet which contains a coating applied to the drug core using aqueous solvents without causing significant hydrolytic degradation of azacitidine in the formulation. In certain embodiments, water is employed as the solvent for coating the drug core. In certain embodiments, the oral dosage form of COMPOUND 2 and/or azacitidine is a tablet containing a film coat applied to the drug core using aqueous solvents. In particular embodiments, water is employed as the solvent for film-coating. In particular embodiments, the tablet containing COMPOUND 2 and/or azacitidine is film-coated using aqueous solvents without effecting degradation of the pharmaceutical composition. In particular embodiments, water is used as the film coating solvent without effecting degradation of the pharmaceutical composition. In certain embodiments, an oral dosage form comprising COMPOUND 2 and/or azacitidine and an aqueous film coating effects immediate drug release upon oral delivery. In certain embodiments, the oral dosage form comprising COMPOUND 2 and/or azacitidine and an aqueous film coating effects controlled drug release to the upper gastrointestinal tract, e.g., the stomach, upon oral administration. In particular embodiments, a tablet with an aqueous-based film coating comprises COMPOUND 2 and/or azacytidine as the API.

In certain embodiments, provided herein is a controlled release pharmaceutical formulation for oral administration of azacitidine that releases COMPOUND 2 and/or azacitidine substantially in the stomach, comprising: a) a specific amount of COMPOUND 2 and/or azacitidine; b) a drug release controlling component for controlling the release of COMPOUND 2 and/or azacitidine substantially in the upper gastrointestinal tract, e.g., the stomach; and c) optionally one or more excipients. In certain embodiments, the oral dosage form comprising COMPOUND 2 and/or azacitidine is prepared as a controlled release tablet or capsule which includes a drug core comprising the pharmaceutical composition and optional excipients. Optionally, a "seal coat" or "shell" is applied. In certain embodiments, a formulation provided herein comprising COMPOUND 2 and/or azacitidine provided herein is a controlled release tablet or capsule, which comprises a therapeutically effective amount of COMPOUND 2 and/or azacitidine, a drug release controlling component that controls the release of COMPOUND 2 and/or azacitidine substantially in the stomach upon oral administration, and optionally, one or more excipients.

Particular embodiments provide a drug release controlling component that is a polymer matrix, which swells upon exposure to gastric fluid to effect the gastric retention of the formulation and the sustained release of COMPOUND 2 and/or azacitidine from the polymer matrix substantially in the stomach. In certain embodiments, such formulations may be prepared by incorporating COMPOUND 2 and/or azacitidine into a suitable polymeric matrix during formulation. Examples of such formulations are known in the art. See, e.g., Shell et al., U.S. Patent Publication No. 2002/0051820 (application Ser. No. 09/990,061); Shell et al., U.S. Patent Publication No. 2003/0039688 (application Ser. No. 10/045,823); Gusler et al., U.S. Patent Publication No. 2003/0104053 (application Ser. No. 10/029,134), each of which is incorporated herein by reference in its entirety.

In certain embodiments, the drug release controlling component may comprise a shell surrounding the drug-containing core, wherein the shell releases COMPOUND 2 and/or azacitidine from the core by, e.g., permitting diffusion of COMPOUND 2 and/or azacitidine from the core and promoting gastric retention of the formulation by swelling upon exposure to gastric fluids to a size that is retained in the stomach. In certain embodiments, such formulations may be prepared by first compressing a mixture of COMPOUND 2 and/or azacitidine and one or more excipients to form a drug core, and compressing another powdered mixture over the drug core to form the shell, or enclosing the drug core with a capsule shell made of suitable materials. Examples of such formulations are known in the art. See, e.g., Berner et al., U.S. Patent Publication No. 2003/0104062 application Ser. No. 10/213,823), incorporated herein by reference in its entirety.

In certain embodiments, the pharmaceutical formulations provided herein contain COMPOUND 2 and/or azacitidine and, optionally, one or more excipients to form a "drug core." Optional excipients include, e.g., diluents (bulking agents), lubricants, disintegrants, fillers, stabilizers, surfactants, preservatives, coloring agents, flavoring agents, binding agents, excipient supports, glidants, permeation enhancement excipients, plasticizers and the like, e.g., as known in the art. It will be understood by those in the art that some substances serve more than one purpose in a pharmaceutical composition. For instance, some substances are binders that help hold a tablet together after compression, yet are also disintegrants that help break the tablet apart once it reaches the target delivery site. Selection of excipients and amounts to use may be readily determined by the formulation scientist based upon experience and consideration of standard procedures and reference works available in the art.

In certain embodiments, formulations provided herein comprise one or more binders. Binders may be used, e.g., to impart cohesive qualities to a tablet, and thus ensure that the tablet remains intact after compression. Suitable binders include, but are not limited to, starch (including corn starch and pregelatinized starch), gelatin, sugars (including sucrose, glucose, dextrose and lactose), polyethylene glycol, propylene glycol, waxes, and natural and synthetic gums, e.g., acacia sodium alginate, polyvinylpyrrolidone, cellulosic polymers (including hydroxypropyl cellulose, hydroxypropylmethylcellulose, methyl cellulose, ethyl cellulose, hydroxyethyl cellulose, carboxymethyl cellulose and the like), veegum, carbomer (e.g., carbopol), sodium, dextrin, guar gum, hydrogenated vegetable oil, magnesium aluminum silicate, maltodextrin, polymethacrylates, povidone (e.g., KOLLIDON, PLASDONE), microcrystalline cellulose, among others. Binding agents also include, e.g., acacia, agar, alginic acid, cabomers, carrageenan, cellulose acetate phthalate, ceratonia, chitosan, confectioner's sugar, copovidone, dextrates, dextrin, dextrose, ethylcellulose, gelatin, glyceryl behenate, guar gum, hydroxyethyl cellulose, hydroxyethylmethyl cellulose, hydroxypropyl cellulose, hydroxypropyl starch, hypromellose, inulin, lactose, magnesium aluminum silicate, maltodextrin, maltose, methylcellulose, poloxamer, polycarbophil, polydextrose, polyethylene oxide, polymethylacrylates, povidone, sodium alginate, sodium carboxymethylcellulose, starch, pregelatinized starch, stearic acid, sucrose, and zein. The binding agent can be, relative to the drug core, in the amount of about 2% w/w of the drug core; about 4% w/w of the drug core, about 6% w/w of the drug core, about 8% w/w of the drug core, about 10% w/w of the drug core, about 12% w/w of the drug core, about 14% w/w of the drug core, about 16% w/w of the drug core, about 18% w/w of the drug core, about 20% w/w of the drug core, about 22% w/w of the drug core, about 24% w/w of the drug core, about 26% w/w of the drug core, about 28% w/w of the drug core, about 30% w/w of the drug core, about 32% w/w of the drug core, about 34% w/w of the drug core, about 36% w/w of the drug core, about 38% w/w of the drug core, about 40% w/w of the drug core, about 42% w/w of the drug core, about 44% w/w of the drug core, about 46% w/w of the drug core, about 48% w/w of the drug core, about 50% w/w of the drug core, about 52% w/w of the drug core, about 54% w/w of the drug core, about 56% w/w of the drug core, about 58% w/w of the drug core, about 60% w/w of the drug core, about 62% w/w of the drug core, about 64% w/w of the drug core, about 66% w/w of the drug core; about 68% w/w of the drug core, about 70% w/w of the drug core, about 72% w/w of the drug core, about 74% w/w of the drug core, about 76% w/w of the drug core, about 78% w/w of the drug core, about 80% w/w of the drug core, about 82% w/w of the drug core, about 84% w/w of the drug core, about 86% w/w of the drug core, about 88% w/w of the drug core, about 90% w/w of the drug core, about 92% w/w of the drug core, about 94% w/w of the drug core, about 96% w/w of the drug core, about 98% w/w of the drug core, or more, if determined to be appropriate. In certain embodiments, a suitable amount of a particular binder is determined by one of ordinary skill in the art.

In certain embodiments, formulations provided herein comprise one or more diluents. Diluents may be used, e.g., to increase bulk so that a practical size tablet is ultimately provided. Suitable diluents include dicalcium phosphate, calcium sulfate, lactose, cellulose, kaolin, mannitol, sodium chloride, dry starch, microcrystalline cellulose (e.g., AVICEL), microfine cellulose, pregelitinized starch, calcium carbonate, calcium sulfate, sugar, dextrates, dextrin, dextrose, dibasic calcium phosphate dihydrate, tribasic calcium phosphate, kaolin, magnesium carbonate, magnesium oxide, maltodextrin, mannitol, polymethacrylates (e.g., EUDRAGIT), potassium chloride, sodium chloride, sorbitol and talc, among others. Diluents also include, e.g., ammonium alginate, calcium carbonate, calcium phosphate, calcium sulfate, cellulose acetate, compressible sugar, confectioner's sugar, dextrates, dextrin, dextrose, erythritol, ethylcellulose, fructose, fumaric acid, glyceryl palmitostearate, isomalt, kaolin, lacitol, lactose, mannitol, magnesium carbonate, magnesium oxide, maltodextrin, maltose, medium-chain triglycerides, microcrystalline cellulose, microcrystalline silicified cellulose, powered cellulose, polydextrose, polymethylacrylates, simethicone, sodium alginate, sodium chloride, sorbitol, starch, pregelatinized starch, sucrose, sulfobutylether-β-cyclodextrin, talc, tragacanth, trehalose, and xylitol. Diluents may be used in amounts calculated to obtain a desired volume for a tablet or capsule; in certain embodiments, a diluent is used in an amount of about 5% or more, about 10% or more, about 15% or more, about 20% or more, about 22% or more, about 24% or more, about 26% or more, about 28% or more, about 30% or more, about 32% or more, about 34% or more, about 36% or more, about 38% or more, about 40% or more, about 42% or more, about 44% or more, about 46% or more, about 48% or more, about 50% or more, about 52% or more, about 54% or more, about 56% or more, about 58% or more, about 60% or more, about 62% or more, about 64% or more, about 68% or more, about 70% ore more, about 72% or more, about 74% or more, about 76% or more, about 78% or more, about 80% or more, about 85% or more, about 90% or more, or about 95% or more, weight/weight, of a drug core; between about 10% and about 90% w/w of the drug core; between about 20% and about 80% w/w of the drug core; between about 30% and about 70% w/w of the drug core; between about 40% and about 60% w/w of the drug core. In certain embodiments, a suitable amount of a particular diluent is determined by one of ordinary skill in the art.

In certain embodiments, formulations provided herein comprise one or more lubricants. Lubricants may be used, e.g., to facilitate tablet manufacture; examples of suitable lubricants include, for example, vegetable oils such as peanut oil, cottonseed oil, sesame oil, olive oil, corn oil, and oil of theobroma, glycerin, magnesium stearate, calcium stearate, and stearic acid. In certain embodiments, stearates, if present, represent no more than approximately 2 weight % of the drug-containing core. Further examples of lubricants include, e.g., calcium stearate, glycerin monostearate, glyceryl behenate, glyceryl palmitostearate, magnesium lauryl sulfate, magnesium stearate, myristic acid, palmitic acid, poloxamer, polyethylene glycol, potassium benzoate, sodium benzoate, sodium chloride, sodium lauryl sulfate, sodium stearyl fumarate, stearic acid, talc, and zinc stearate. In particular embodiments, the lubricant is magnesium stearate. In certain embodiments, the lubricant is present, relative to the drug core, in an amount of about 0.2% w/w of the drug core, about 0.4% w/w of the drug core, about 0.6% w/w of the drug core, about 0.8% w/w of the drug core, about 1.0% w/w of the drug core, about 1.2% w/w of the drug core, about 1.4% w/w of the drug core, about 1.6% w/w of the drug core, about 1.8% w/w of the drug core, about 2.0% w/w of the drug core, about 2.2% w/w of the drug core, about 2.4% w/w of the drug core, about 2.6% w/w of the drug core, about 2.8% w/w of the drug core, about 3.0% w/w of the drug core, about 3.5% w/w of the drug core, about 4% w/w of the drug core, about 4.5% w/w of the drug core, about 5% w/w of the drug core, about 6% w/w of the drug core, about 7% w/w of the drug core, about 8% w/w of the drug core, about 10% w/w of the drug core, about 12% w/w of the drug core, about 14% w/w of the drug core, about 16% w/w of the drug core, about 18% w/w of the drug core, about 20% w/w of the drug core, about 25% w/w of the drug core, about 30% w/w of the drug core, about 35% w/w of the drug core, about 40% w/w of the drug core, between about 0.2% and about 10% w/w of the drug core, between about 0.5% and about 5% w/w of the drug core, or between about 1% and about 3% w/w of the drug core. In certain embodiments, a suitable amount of a particular lubricant is determined by one of ordinary skill in the art.

In certain embodiments, formulations provided herein comprise one or more disintegrants. Disintegrants may be used, e.g., to facilitate disintegration of the tablet, and may be, e.g., starches, clays, celluloses, algins, gums or cross-linked polymers. Disintegrants also include, e.g., alginic acid, carboxymethylcellulose calcium, carboxymethylcellulose sodium (e.g., AC-DI-SOL, PRIMELLOSE), colloidal silicon dioxide, croscarmellose sodium, crospovidone (e.g., KOLLIDON, POLYPLASDONE), guar gum, magnesium aluminum silicate, methyl cellulose, microcrystalline cellulose, polacrilin potassium, powdered cellulose, pregelatinized starch, sodium alginate, sodium starch glycolate (e.g., EXPLOTAB) and starch. Additional disintegrants include, e.g., calcium alginate, chitosan, sodium docusate, hydroxypropyl cellulose, and povidone. In certain embodiments, the disintegrant is, relative to the drug core, present in the amount of about 1% w/w of the drug core, about 2% w/w of the drug core, about 3% w/w of the drug core, about 4% w/w of the drug core, about 5% w/w of the drug core, about 6% w/w of the drug core, about 7% w/w of the drug core, about 8% w/w of the drug core, about 9% w/w of the drug core, about 10% w/w of the drug core, about 12% w/w of the drug core, about 14% w/w of the drug core, about 16% w/w of the drug core, about 18% w/w of the drug core, about 20% w/w of the drug core, about 22% w/w of the drug core, about 24% w/w of the drug core, about 26% w/w of the drug core, about 28% w/w of the drug core, about 30% w/w of the drug core, about 32% w/w of the drug core, greater than about 32% w/w of the drug core, between about 1% and about 10% w/w of the drug core, between about 2% and about 8% w/w of the drug core, between about 3% and about 7% w/w of the drug core, or between about 4% and about 6% w/w of the drug core. In certain embodiments, a suitable amount of a particular disintegrant is determined by one of ordinary skill in the art.

In certain embodiments, formulations provided herein comprise one or more stabilizers. Stabilizers (also called absorption enhancers) may be used, e.g., to inhibit or retard drug decomposition reactions that include, by way of example, oxidative reactions. Stabilizing agents include, e.g., d-Alpha-tocopheryl polyethylene glycol 1000 succinate (Vitamin E TPGS), acacia, albumin, alginic acid, aluminum stearate, ammonium alginate, ascorbic acid, ascorbyl palmitate, bentonite, butylated hydroxytoluene, calcium alginate, calcium stearate, calcium carboxymethylcellulose, carrageenan, ceratonia, colloidal silicon dioxide, cyclodextrins, diethanolamine, edetates, ethylcellulose, ethyleneglycol palmitostearate, glycerin monostearate, guar gum, hydroxypropyl cellulose, hypromellose, invert sugar, lecithin, magnesium aluminum silicate, monoethanolamine, pectin, poloxamer, polyvinyl alcohol, potassium alginate, potassium polacrilin, povidone, propyl gallate, propylene glycol, propylene glycol alginate, raffinose, sodium acetate, sodium alginate, sodium borate, sodium carboxymethyl cellulose, sodium stearyl fumarate, sorbitol, stearyl alcohol, sufobutyl-b-cyclodextrin, trehalose, white wax, xanthan gum, xylitol, yellow wax, and zinc acetate. In certain embodiments, the stabilizer is, relative to the drug core, present in the amount of about 1% w/w of the drug core, about 2% w/w of the drug core, about 3% w/w of the drug core, about 4% w/w of the drug core, about 5% w/w of the drug core, about 6% w/w of the drug core, about 7% w/w of the drug core, about 8% w/w of the drug core, about 9% w/w of the drug core, about 10% w/w of the drug core, about 12% w/w of the drug core, about 14% w/w of the drug core, about 16% w/w of the drug core, about 18% w/w of the drug core, about 20% w/w of the drug core, about 22% w/w of the drug core, about 24% w/w of the drug core, about 26% w/w of the drug core, about 28% w/w of the drug core, about 30% w/w of the drug core, about 32% w/w of the drug core, between about 1% and about 10% w/w of the drug core, between about 2% and about 8% w/w of the drug core, between about 3% and about 7% w/w of the drug core, or between about 4% and about 6% w/w of the drug core. In certain embodiments, a suitable amount of a particular stabilizer is determined by one of ordinary skill in the art.

In certain embodiments, formulations provided herein comprise one or more glidants. Glidants may be used, e.g., to improve the flow properties of a powder composition or granulate or to improve the accuracy of dosing. Excipients that may function as glidants include, e.g., colloidal silicon dioxide, magnesium trisilicate, powdered cellulose, starch, tribasic calcium phosphate, calcium silicate, powdered cellulose, colloidal silicon dioxide, magnesium silicate, magnesium trisilicate, silicon dioxide, starch, tribasic calcium phosphate, and talc. In certain embodiments, the glidant is, relative to the drug core, present in the amount of less than about 1% w/w of the drug core, about 1% w/w of the drug core, about 2% w/w of the drug core, about 3% w/w of the drug core, about 4% w/w of the drug core, about 5% w/w of the drug core, about 6% w/w of the drug core, about 7% w/w of the drug core, about 8% w/w of the drug core, about 9% w/w of the drug core, about 10% w/w of the drug core, about 12% w/w of the drug core, about 14% w/w of the drug core, about 16% w/w of the drug core, about 18% w/w of the drug core, about 20% w/w of the drug core, about 22% w/w of the drug core, about 24% w/w of the drug core, about 26% w/w of the drug core, about 28% w/w of the drug core, about 30% w/w of the drug core, about 32% w/w of the drug core, between about 1% and about 10% w/w of the drug core, between about 2% and about 8% w/w of the drug core, between about 3% and about 7% w/w of the drug core, or between about 4% and about 6% w/w of the drug core. In certain embodiments, a suitable amount of a particular glidant is determined by one of ordinary skill in the art.

In certain embodiments, formulations provided herein comprise one or more permeation enhancers (also called, e.g., permeability enhancers). In certain embodiments, the permeation enhancer enhances the uptake of azacitidine through the gastrointestinal wall (e.g., the stomach). In certain embodiments, the permeation enhancer alters the rate and/or amount of azacitidine that enters the bloodstream. In particular embodiments, d-alpha-tocopheryl polyethylene glycol-1000 succinate (Vitamin E TPGS) is used as a permeation enhancer. In particular embodiments, one or more other suitable permeation enhancers are used, including, e.g., any permeation enhancer known in the art.

In one embodiment, the pharmaceutical compositions provided herein may be administered orally, parenterally, by inhalation spray, topically, rectally, nasally, buccally, vaginally or via an implanted reservoir, preferably by oral administration or administration by injection. In one embodiment, the pharmaceutical compositions may contain any conventional non-toxic pharmaceutically-acceptable carriers, adjuvants or vehicles. In some cases, the pH of the formulation may be adjusted with pharmaceutically acceptable acids, bases or buffers to enhance the stability of the formulated compound or its delivery form. The term parenteral as used herein includes subcutaneous, intracutaneous, intravenous, intramuscular, intraarticular, intraarterial, intrasynovial, intrasternal, intrathecal, intralesional and intracranial injection or infusion techniques.

In one embodiment, the pharmaceutical compositions provided herein may be in the form of a sterile injectable preparation, for example, as a sterile injectable aqueous or oleaginous suspension. This suspension may be formulated according to techniques known in the art using suitable dispersing or wetting agents (such as, for example, Tween 80) and suspending agents. The sterile injectable preparation may also be a sterile injectable solution or suspension in a non-toxic parenterally acceptable diluent or solvent, for example, as a solution in 1,3-butanediol. Among the acceptable vehicles and solvents that may be employed are mannitol, water, Ringer's solution and isotonic sodium chloride solution. In addition, sterile, fixed oils are conventionally employed as a solvent or suspending medium. For this purpose, any bland fixed oil may be employed including synthetic mono- or diglycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant, or carboxymethyl cellulose or similar dispersing agents which are commonly used in the formulation of pharmaceutically acceptable dosage forms such as emulsions and or suspensions. Other commonly used surfactants such as Tweens or Spans and/or other similar emulsifying agents or bioavailability enhancers which are commonly used in the manufacture of pharmaceutically acceptable solid, liquid, or other dosage forms may also be used for the purposes of formulation.

In one embodiment, the pharmaceutical compositions provided herein may also be administered in the form of suppositories for rectal administration. These compositions can be prepared by mixing a compound of one aspect of this invention with a suitable non-irritating excipient which is solid at room temperature but liquid at the rectal temperature and therefore will melt in the rectum to release the active components. Such materials include, but are not limited to, cocoa butter, beeswax and polyethylene glycols.

Topical administration of the pharmaceutical compositions provided herein is useful when the desired treatment involves areas or organs readily accessible by topical application. For application topically to the skin, the pharmaceutical composition should be formulated with a suitable ointment containing the active components suspended or dissolved in a carrier. Carriers for topical administration of the compounds of one aspect of this invention include, but are not limited to, mineral oil, liquid petroleum, white petroleum, propylene glycol, polyoxyethylene polyoxypropylene compound, emulsifying wax and water. Alternatively, the pharmaceutical composition can be formulated with a suitable lotion or cream containing the active compound suspended or dissolved in a carrier with suitable emulsifying agents. Suitable carriers include, but are not limited to, mineral oil, sorbitan monostearate, polysorbate 60, cetyl esters wax, cetearyl alcohol, 2-octyldodecanol, benzyl alcohol and water. The pharmaceutical compositions provided herein may also be topically applied to the lower intestinal tract by rectal suppository formulation or in a suitable enema formulation. Topically-transdermal patches are also included herein.

In one embodiment, the pharmaceutical compositions provided herein may be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other solubilizing or dispersing agents known in the art.

When the compositions provided herein comprise a combination of COMPOUND 2 and azacitidine, both the COMPOUND 2 and azacitidine should be present at dosage levels of between about 1 to 100%, and more preferably between about 5 to 95% of the dosage normally administered in a monotherapy regimen. Azacitidine may be administered separately, as part of a multiple dose regimen, from the compounds of one aspect of this invention. Alternatively, azacitidine may be part of a single dosage form, mixed together with COMPOUND 2 in a single composition.

In one embodiment, the compositions provided herein can, for example, be administered by injection, intravenously, intraarterially, subdermally, intraperitoneally, intramuscularly, or subcutaneously; or orally, buccally, nasally, transmucosally, topically, in an ophthalmic preparation, or by inhalation, with a dosage ranging from about 0.5 to about 100 mg/kg of body weight, alternatively dosages between 1 mg and 1000 mg/dose, every 4 to 120 hours, or according to the requirements of the particular drug. The methods herein contemplate administration of an effective amount of compound or compound composition to achieve the desired or stated effect. In one embodiment, the pharmaceutical compositions are administered from about 1 to about 6 times per day or alternatively, as a continuous infusion. Such administration can be used as a chronic or acute therapy. The amount of active ingredient that may be combined with the carrier materials to produce a single dosage form varies depending upon the host treated and the particular mode of administration. A typical preparation contains from about 5% to about 95% active compound (w/w). Alternatively, such preparations contain from about 20% to about 80% active compound.

Lower or higher doses than those recited above may be required. Specific dosage and treatment regimens for any particular subject depends upon a variety of factors, including the activity of the specific compound employed, the age, body weight, general health status, sex, diet, time of administration, rate of excretion, drug combination, the severity and course of the disease, condition or symptoms, the subject's disposition to the disease, condition or symptoms, and the judgment of the treating physician.

Upon improvement of a subject's condition, a maintenance dose of a compound, composition or combination provided herein may be administered, if necessary. Subsequently, the dosage or frequency of administration, or both, may be reduced, as a function of the symptoms, to a level at which the improved condition is retained when the symptoms have been alleviated to the desired level. Subjects may, however, require intermittent treatment on a long-term basis upon any recurrence of disease symptoms.

Solid Dispersions of COMPOUND 2

In certain embodiment, COMPOUND 2 is administered in compositions, comprising COMPOUND 2, and one or more polymer(s) as part of a solid dispersion (e.g., an amorphous solid dispersion). In some embodiments, the solid dispersion comprises COMPOUND 2, and one or more polymer(s). In some embodiments, the solid dispersion comprises COMPOUND 2, one or more polymer(s), and one or more surfactant(s). In some embodiments, the solid dispersion comprises COMPOUND 2, and one polymer. In some embodiments, the solid dispersion comprises COMPOUND 2, one polymer, and a surfactant.

In certain embodiment, the solid dispersions provided herein, comprising COMPOUND 2, enhance the solubility of COMPOUND 2 relative to a neat crystalline form of COMPOUND 2 (e.g., Form 1 or Form 2), and thus provide improved exposure upon oral dosing of the solid dispersion to a subject. In one embodiment, the solid dispersion comprises COMPOUND 2, one or more polymer(s), and optionally one or more solubility enhancing surfactant.

For example, the aqueous solubility of Form 1 is about 0.025 mg/mL to about 0.035 mg/mL and the aqueous solubility of Form 2 is about 0.008 mg/mL to about 0.010 mg/mL.

Form 2 has a solubility of about 0.018 mg/mL in fasted state simulated intestinal fluid (FASSIF) at a pH of 6.1 at 4 hours. In comparison, amorphous spray-dried dispersions have a solubility of about 0.05 mg/mL to about 0.50 mg/mL in FASSIF at 3 hours.

In some embodiments, the solid dispersion exhibits at least about 20%, at least about 30%, at least about 40%, at least about 50%, at least about 60%, at least about 70%, at least about 80%, or at least about 90% higher exposure of COMPOUND 2, when administered to a subject as compared to administration of in-situ amorphous COMPOUND 2. In some embodiments, the solid dispersion exhibits at least about 20%, at least about 30%, at least about 40%, at least about 50%, at least about 60%, at least about 70%, at least about 80%, or at least about 90% higher exposure of COMPOUND 2, when administered to a subject as compared to administration of neat crystalline COMPOUND 2.

In rat and monkey pharmacokinetics studies, modest exposure improvement is observed upon administration of solid dispersion oral dosage forms as compared to in-situ amorphous dosing shows. For example, a solid dispersion containing 50% w/w COMPOUND 2 and 50% w/w Polyvinyl Acetate Phthalate (PVAP) has approximately two-fold higher exposure as compared to in-situ amorphous COMPOUND 2 in male Sprague Dawley rats. There is no significant difference in exposure between a solid dispersion containing 70% w/w COMPOUND 2 and 30% w/w oral dosage form as compared to in-situ amorphous COMPOUND 2. In male cynomolgus monkeys, the exposure of a solid dispersion containing 50% w/w COMPOUND 2 and 50% w/w hydroxypropylmethylcellulose acetate succinate, also known as hpromellose acetate succinate, (HPMCAS) shows no significant difference as compared to the in-situ amorphous COMPOUND 2. Similarly, a solid dispersion containing 50% w/w COMPOUND 2 and 50% w/w hydroxypropylmethylcellulose also known as hypromellose phthalate (HPMC-Phthalate) shows no significant difference as compared to the in-situ amorphous COMPOUND 2. While in-situ amorphous therapeutic compounds are commonly used for dosing in animal studies, they are not suitable dosage forms for dosing in humans.

As described in the rat pharmacokinetics study of Example 4, COMPOUND 2 exposure is improved when solid dispersion dosage forms are administered as compared to neat crystalline COMPOUND 2 Form 2.

In some embodiments, at least a portion of COMPOUND 2, in the solid dispersion is in the amorphous state (e.g., at least about 50%, at least about 55%, at least about 60%, at least about 65%, at least about 70%, at least about 75%, at least about 80%, at least about 85%, at least about 90%, at least about 95%, at least about 98%, or at least about 99%). In other embodiments, the solid dispersion is substantially free of crystalline COMPOUND 2.

In some embodiments, the composition is an amorphous solid (e.g. spray dried) dispersion comprising COMPOUND 2, and a polymer. The amorphous solid dispersion can include, e.g., less than about 30%, less than about 20%, less than about 15%, less than about 10%, less than about 5%, less than about 4%, less than about 3%, less than about 2%, or less than about 1% of crystalline COMPOUND 2, e.g., be substantially free of crystalline COMPOUND 2.

In one embodiment, the solid dispersion exhibits a predetermined level of physical and/or chemical stability. E.g., the solid dispersion retains about 50%, about 60%, about 70%, about 80%, about 90%, about 95%, about 98%, or about 99%, of amorphous COMPOUND 2, when stored at 25° C. in a closed water tight container, e.g., an amber glass vial, high density polyethylene (HDPE) container or double polyethylene bags with twisted nylon tie placed in an HDPE container with desiccant.

In some embodiments, the polymer increases the chemical or physical stability (e.g., as measured by a Modulated Differential Scanning calorimeter) of COMPOUND 2, when stored (e.g., at 2-8° C., e.g. 4° C. or at room temperature) by at least about 10% (e.g., by at least about 20%, by at least about 30%, by at least about 40%, by at least about 50%, by at least about 60%, by at least about 70%, by at least about 80%, or by at least about 90%) compared to amorphous COMPOUND 2, without being in the presence of the polymer.

A solid dispersion generally exhibits a glass transition temperature, where the dispersion makes a transition from a glassy solid to a rubbery composition. In general, the higher the glass transition temperature, the greater the physical stability of the dispersion. The existence of a glass transition temperature generally indicates that at least a large portion of the composition (e.g., dispersion) is in an amorphous state. The glass transition temperature (Tg) of a solid dispersion suitable for pharmaceutical applications is generally at least about 50° C. In some embodiments, higher temperatures are preferred. Therefore, in some embodiments, a solid dispersion disclosed herein has a Tg of at least about 100° C. (e.g., at least about 100° C., at least about 105° C., at least about 110° C., at least about 115° C., at least about 120° C., at least about 125° C., at least about 130° C., at least about 135° C., at least about 140° C., at least about 150° C., at least about 160° C., at least about 170° C., at least about 175° C., at least about 180° C., or at least about 190° C.). In some embodiments, the Tg is up to about 200° C. In some embodiments, the Tg is up to about 130° C. (e.g., at least about 110° C., at least about 111° C., at least about 112° C., at least about 113° C., at least about 114° C., at least about 115° C., at least about 116° C., at least about 117° C., at least about 118° C., at least about 119° C., at least about 120° C., at least about 121° C., at least about 122° C., at least about 123° C., at least about 124° C., at least about 125° C., at least about 126° C., at least about 127° C., at least about 128° C., at least about 129° C., or at least about 130° C.). Unless otherwise noted, the glass transition temperatures disclosed herein are measured under dry conditions.

In some embodiments the solid dispersion has a higher glass transition temperature than the glass transition temperature of amorphous COMPOUND 2, without being in the presence of the polymer(s). In some embodiments, the solid dispersion has a relaxation rate that is lower than the relaxation rate of amorphous COMPOUND 2, without being in the presence of the polymer(s).

Examples of polymers in the solid dispersion include cellulose derivatives (e.g., hydroxypropylmethylcellulose also known as hypromellose, (HPMC), hydroxypropylmethylcellulose phthalate, also known as hypromellose phthalate (HPMCP), hydroxypropylmethylcellulose acetate succinate, also known as hpromellose acetate succinate, (HPMCAS), hydroxypropylcellulose (HPC)), ethylcellulose, or cellulose acetate phthalate; polyvinylpyrrolidones (PVP); polyethylene glycols (PEG); polyvinyl alcohols (PVA); polyvinyl esters, such as Polyvinyl Acetate Phthalate (PVAP); acrylates, such as polymethacrylate (e.g., Eudragit® E); cyclodextrins (e.g., .beta.-cyclodextrin); Poly (D, L-lactide) (PLA), Poly (D,L-lactide, co-glycolide acid (PLGA); and copolymers and derivatives thereof, including for example polyvinylpyrrolidone-vinyl acetate (PVP-VA), Polyvinyl caprolactam-polyvinyl, and acetate-polyethyleneglycol copolymer, Methylacrylate/methacrylic acid copolymer; Soluplus; Copovidone; and mixtures thereof.

In some embodiments, the solid dispersion includes one water-soluble polymer. In some embodiments, the solid dispersion includes one partially water-soluble polymer. In some embodiments, the polymer is a cellulose polymer.

In some embodiments, the polymer is HPMCAS (e.g., HPMCAS of different grades: HPMCAS-M, HPMCAS-MG or HPMCAS-HG). In some embodiments, the polymer is PVAP. In some embodiments, the polymer is HPMC (e.g., HPMC of different grades: HMPC60SH50, HPMCE50 or HPMCE15). In some embodiments, the polymer is HPMCP (e.g., HPMCP of different grades: e.g., HMPCP-HP55).

In some embodiments, the polymer is a pH-dependent enteric polymer. Such pH-dependent enteric polymers include, but are not limited to, cellulose derivatives (e.g., cellulose acetate phthalate (CAP)), HPMCP, HPMCAS, carboxymethylcellulose (CMC) or a salt thereof (e.g., a sodium salt such as (CMC-Na)); cellulose acetate trimellitate (CAT), hydroxypropylcellulose acetate phthalate (HP-CAP), hydroxypropylmethyl-cellulose acetate phthalate (HPMCAP), and methylcellulose acetate phthalate (MCAP), polymethacrylates (e.g., Eudragit S), or mixtures thereof.

In some embodiments, the polymer is hydroxypropylmethylcellulose acetate succinate, also known as hypromellose acetate succinate, (HPMCAS), e.g., HMPCAS-HG.

In another embodiment, the polymer(s) is an insoluble cross-linked polymer, for example a polyvinylpyrrolidone (e.g., Crospovidone). In another embodiment, the polymer(s) is polyvinylpyrrolidone (PVP).

In some embodiments, the one or more polymer(s) is present in the solid dispersion in an amount of between about 10% w/w and 90% w/w (e.g., between about 20% w/w and about 80% w/w; between about 30% w/w and about 70% w/w; between about 40% w/w and about 60% w/w; or between about 15% w/w and about 35% w/w). In some embodiments, the polymer(s) is present in the solid dispersion in an amount of from about 10% w/w to about 80% w/w, for example from about 30% w/w to about 75% w/w, or from about 40% w/w to about 65% w/w, or from about 45% w/w to about 55% w/w, for example, about 46% w/w, about 47% w/w, about 48% w/w, about 49% w/w, about 50% w/w, about 51% w/w, about 52% w/w, about 53% w/w, or about 54% w/w. In some embodiments, the polymer(s) is present in the solid dispersion in an amount of about 48% w/w, about 48.5% w/w, about 49% w/w, about 49.5% w/w, about 50% w/w, about 50.5% w/w, about 51% w/w, about 51.5% w/w, about 52% w/w, or about 52.5% w/w.

In some embodiments, the polymer(s) is present in the solid dispersion in an amount of from about 30% w/w to about 70% w/w. In some embodiments, the polymer(s) is present in the solid dispersion in an amount of from about 35% w/w to about 65% w/w. In some embodiments, the polymer(s) is present in the solid dispersion in an amount of from about 40% w/w to about 60% w/w. In some embodiments, the polymer(s) is present in the solid dispersion in an amount of from about 45% w/w to about 55% w/w. In some embodiments, the polymer(s) is present in the solid dispersion in an amount of about 50% w/w.

In some embodiments, COMPOUND 2, is present in the solid dispersion in an amount of from about 10% w/w and 90% w/w (e.g., between about 20% w/w and about 80% w/w; between about 30% w/w and about 70% w/w; between about 40% w/w and about 60% w/w; or between about 15% w/w and about 35% w/w). In some embodiments, COMPOUND 2, is present in the solid dispersion in an amount of from about 10% w/w to about 80% w/w, for example from about 30% w/w to about 75% w/w, or from about 40% w/w to about 65% w/w, or from about 45% w/w to about 55% w/w, for example, about 46% w/w, about 47% w/w, about 48% w/w, about 49% w/w, about 50% w/w, about 51% w/w, about 52% w/w, about 53% w/w, or about 54% w/w. In some embodiments, COMPOUND 2, is present in the solid dispersion in an amount of about 48% w/w, about 48.5% w/w, about 49% w/w, about 49.5% w/w, about 50% w/w, about 50.5% w/w, about 51% w/w, about 51.5% w/w, about 52% w/w, or about 52.5% w/w.

In some embodiments, COMPOUND 2, is present in the solid dispersion in an amount of from about 30% w/w to about 70% w/w. In some embodiments, COMPOUND 2, is present in the solid dispersion in an amount of from about 35% w/w to about 65% w/w. In some embodiments, COMPOUND 2, is present in the solid dispersion in an amount of from about 40% w/w to about 60% w/w. In some embodiments, COMPOUND 2, is present in the solid dispersion in an amount of from about 45% w/w to about 55% w/w. In some embodiments, COMPOUND 2, is present in the solid dispersion in an amount of about 50% w/w.

In another embodiment, the solid dispersion includes about 20% w/w to about 80% w/w COMPOUND 2, and about 20% w/w to about 80% of polymer(s). In another embodiment, the solid dispersion includes about 25% w/w to about 75% w/w COMPOUND 2, and about 25% w/w to about 75% of polymer(s). In another embodiment, the solid dispersion includes about 30% w/w to about 70% w/w COMPOUND 2, and about 30% w/w to about 70% of polymer(s). In another embodiment, the solid dispersion includes about 35% w/w to about 65% w/w COMPOUND 2, and about 35% w/w to about 65% of polymer(s). In another embodiment, the solid dispersion includes about 40% w/w to about 60% w/w COMPOUND 2, and about 40% w/w to about 60% of polymer(s). In another embodiment, the solid dispersion includes about 45% w/w to about 55% w/w COMPOUND 2, and about 45% w/w to about 55% of polymer(s). In another embodiment, the solid dispersion includes about 50% w/w COMPOUND 2, and about 50% w/w of polymer(s).

In another embodiment, the solid dispersion includes about 45% w/w to about 55% w/w COMPOUND 2, and about 45% w/w to about 55% w/w HPMCAS (e.g., HPMCAS-MG or HPMCAS-HG, or other grades such as LF, MF, HF, or LG) or PVAP. In another embodiment, the solid dispersion includes about 50% w/w COMPOUND 2, and about 50% w/w of HPMCAS.

In some embodiments, the solid dispersion also includes a surfactant or inert pharmaceutically acceptable substance. Examples of surfactants in the solid dispersion include sodium lauryl sulfate (SLS), vitamin E or a derivative thereof (e.g., vitamin E TPGS), Docusate Sodium, sodium dodecyl sulfate, polysorbates (such as Tween 20 and Tween 80), poloxamers (such as Poloxamer 335 and Poloxamer 407), glyceryl monooleate, Span 65, Span 25, Capryol 90, pluronic copolymers (e.g., Pluronic F108, Pluronic P-123), and mixtures thereof. In some embodiments, the surfactant is SLS. In some embodiments, the surfactant is vitamin E or a derivative thereof (e.g., vitamin E TPGS).

In some embodiments, the surfactant is present in the solid dispersion in an amount of from about 0.1% w/w to about 10% w/w, for example from about 0.5% w/w to about 2% w/w, or from about 1% w/w to about 3% w/w, from about 1% w/w to about 4% w/w, or from about 1% w/w to about 5% w/w. In some embodiments, the surfactant is present in the solid dispersion in an amount of about 0.1% w/w, about 0.2% w/w, about 0.3% w/w, about 0.4% w/w, about 0.5% w/w, about 0.6% w/w, about 0.7% w/w, about 0.8% w/w, about 0.9% w/w, or about 1% w/w. In some embodiments, the surfactant is present in the solid dispersion in an amount of about 0.5% w/w, about 1% w/w, about 1.5% w/w, about 2% w/w, about 2.5% w/w, about 3% w/w, about 3.5% w/w, about 4% w/w, about 4.5% w/w, or about 5% w/w.

Processes for Preparing Solid Dispersions

In some embodiments, the solid dispersion may be prepared according to a process described herein. In general, methods that could be used include those that involve rapid removal of solvent or solvent mixture from a mixture or cooling a molten sample. Such methods include, but are not limited to, rotational evaporation, freeze-drying (i.e., lyophilization), vacuum drying, melt congealing, and melt extrusion. One embodiment of this disclosure involves solid dispersion obtained by spray-drying. In one embodiment, the product obtained by spray drying is dried to remove the solvent or solvent mixture.

Preparations disclosed herein, e.g., a pharmaceutical composition, can be obtained by spray-drying a mixture comprising COMPOUND 2, one or more polymer(s), and an appropriate solvent or solvent mixture. Spray drying involves atomization of a liquid mixture containing, e.g., a solid and a solvent or solvent mixture, and removal of the solvent or solvent mixture. The solvent or solvent mixture can also contain a nonvolatile solvent, such as glacial acetic acid. Atomization may be done, for example, through a two-fluid or pressure or electrosonic nozzle or on a rotating disk.

Spray drying converts a liquid feed to a dried particulate form. Spray drying generally involves the atomization of a liquid feed solution into a spray of droplets and contacting the droplets with hot air or gas in a drying chamber. The sprays are generally produced by either rotary (wheel) or nozzle atomizers. Evaporation of moisture from the droplets and formation of dry particles proceed under controlled temperature and airflow conditions.

Optionally, a secondary drying process such as fluidized bed drying or vacuum drying, may be used to reduce residual solvents (and other additives, such as glacial acetic acid) to pharmaceutically acceptable levels. Typically, spray-drying involves contacting a highly dispersed liquid suspension or solution (e.g., atomized solution), and a sufficient volume of hot air or gas (e.g., nitrogen, e.g., pure nitrogen) to produce evaporation and drying of the liquid droplets. The preparation to be spray dried can be any solution, coarse suspension, slurry, colloidal dispersion, or paste that may be atomized using the selected spray-drying apparatus. In a standard procedure, the preparation is sprayed into a current of warm filtered air (or into gas, e.g., nitrogen) that evaporates the solvent and conveys the dried product to a collector (e.g., a cyclone). The spent air or gas is then exhausted with the solvent (or solvent mixture including any additives such as glacial acetic acid), (e.g., then filtered) or alternatively the spent air or gas is sent to a condenser to capture and potentially recycle the solvent or solvent mixture. For example, if a gas (e.g., nitrogen) is used, the gas is then optionally recycled, heated again and returned to the unit in a closed loop system. Commercially available types of apparatus may be used to conduct the spray-drying. For example, commercial spray dryers are manufactured by Buchi Ltd. and Niro (e.g., the PSD line of spray driers manufactured by Niro).

Spray-drying typically employs solids loads of material from about 1% to about 30% or up to about 50% (i.e., therapeutically active compound plus and excipients), preferably at least about 10%. In some embodiments, solids loads of less than 10% may result in poor yields and unacceptably long run-times. In general, the upper limit of solids loads is governed by the viscosity of (e.g., the ability to pump) the resulting solution and the solubility of the components in the solution. Generally, the viscosity of the solution can determine the size of the particle in the resulting powder product.

Techniques and methods for spray-drying may be found in Perry's Chemical Engineering Handbook, 6th Ed., R. H. Perry, D. W. Green & J. O. Maloney, eds., McGraw-Hill Book Co. (1984); and Marshall "Atomization and Spray-Drying" 50, Chem. Eng. Prog. Monogr. Series 2 (1954). In general, the spray-drying is conducted with an inlet temperature of from about 40° C. to about 200° C., for example, from about 70° C. to about 150° C., preferably from about 40° C. to about 60° C., about 50° C. to about 55° C., or about 80° C. to about 110° C., e.g., about 90° C. The spray-drying is generally conducted with an outlet temperature of from about 20° C. to about 100° C., for example from about 25° C. to about 30° C. (e.g., about 26° C.), about 40° C. to about 50° C., about 50° C. to about 65° C., e.g., about 56° C. to about 58° C.

Removal of the solvent or solvent mixture may require a subsequent drying step, such as tray drying, fluid bed drying (e.g., from about room temperature to about 100° C.), vacuum drying, microwave drying, rotary drum drying or biconical vacuum drying (e.g., from about room temperature to about 200° C.).

In one embodiment, the spray-drying is fluidized spray drying (FSD). The steps in FSD can include, for example: preparing a liquid feed solution (e.g., containing COMPOUND 2, and optionally a polymer(s) and/or surfactant(s), dissolved or suspended in solvent(s)); atomizing (e.g., with a pressure nozzle, a rotary atomizer or disk, two-fluid nozzle or other atomizing methods) the feed solution upon delivery into the drying chamber of a spray dryer, e.g., operating in FSD mode; drying the feed solution in the drying chamber with heated air or a heated gas (e.g., nitrogen) to obtain a product, wherein larger particles of product separate out, e.g., drop out, while fines are carried by a stream of air or gas up to the top of the drying chamber (e.g., by natural convection) and to a cyclone, and re-introducing (e.g., at the top of the drying chamber or axially to the middle of the chamber) the fines into the drying chamber, wherein the re-introduced fines can agglomerate with newly formed product to generate an agglomerated product, wherein if the agglomerated product is large enough, it will separate out, if it is not large enough to separate out, the agglomerated product will be carried by convection to the top of the chamber and to the cyclone and re-introduced into the chamber. This process repeats until an agglomerated product that is large enough to drop out is formed. The fines can be re-introduced from the cyclone to the drying chamber via a feed pipe.

In some embodiments, rather than drying the feed solution with heated air or a heated gas, the feed solution can instead be spray congealed, e.g., the chamber is at room temperature (e.g., 21±4° C.) or is cooled, e.g., cooled gas (e.g., nitrogen) is used for the process.

FSD can further include collecting the agglomerated product in a first fluidizing chamber; which can be followed by discharging the agglomerated product from the first fluidizing chamber to a second fluidizing chamber, wherein a post-drying process can occur.

The agglomerated product (e.g., that separates out in the drying chamber) can then be transferred from the second fluidizing chamber to a third fluidizing chamber, where the agglomerated product is cooled. The agglomerated product (e.g., a solid dispersion of an amorphous compound) can then be further processed. For example, the product can be directly compressed. The product can optionally be blended with a surfactant, excipient, or pharmaceutically acceptable carrier, e.g., prior to direct compression. The product can optionally be further processed, e.g., milled, granulated, blended, and/or mixed with a melt granulate, surfactant, excipient, and/or pharmaceutically acceptable carrier.

FSD can be performed in a commercial spray dryer operating in fluidized spray dryer mode (FSD mode). FSD can be accomplished in either open cycle mode or closed cycle mode (e.g., the drying gas, e.g., nitrogen, is recycled). Examples of suitable spray dryers for use in FSD include dryers from Niro (e.g., the PSD line of spray driers manufactured by Niro: PHARMASD™; Chemical or SD line dryers). FSD can essentially be performed in any spray dryer that is configured to allow for the re-introduction of fines into the drying chamber.

Additional post drying, e.g., in a vacuum or fluidized bed dryer or a double cone or biconical post-dryer or a tumble dryer, can be performed if needed/applicable to remove further solvents. In some embodiments, a post-drying step is performed.

To remove the solvent or solvent mixture, vacuum drying, spray drying, fluidized spray drying, tray drying, lyophilization, rotovapping, and other drying procedures may be applied. Applying any of these methods using appropriate processing parameters, according to this disclosure, would provide COMPOUND 2 in an amorphous state in the final solid dispersion product. Upon use of appropriate conditions (e.g., low outlet temperatures in the spray dryer, use of low boiling point solvents, use of heated gas) that result in a dispersion, e.g., powder, with desirable properties (e.g., median particle size (d50) of 40-200 microns 9 e.g., 40-150 microns), powder bulk density of >0.2 g/ml (e.g., 0.2 to 0.5 g/ml), or >0.25 g/ml, improved powder flowability (e.g., low cohesion forces, low interparticle internal friction); and/or dry powder with low OVIs (Organic Volatile Impurities), e.g., below ICH limits and/or user specifications), the dispersion can be directly compressed into a dosage form.

In some embodiments, the inlet temperature is between about 50° C. and about 200° C., e.g., between about 60° C. and about 150° C., between about 70° C. and about 100° C., between about 60° C. and about 95° C., between about 65° C. and about 85° C., between about 70° C. and about 90° C., between about 85° C. and about 95° C., or between about 70° C. and about 85° C.

In some embodiments, the outlet temperature is between about room temperature (e.g., USP room temperature (e.g., 21±4° C.)) and about 80° C., e.g., between about 25° C. and about 75° C., between about 30° C. and about 65° C., between about 35° C. and about 70° C., between about 40° C. and about 65° C., between about 45° C. and about 60° C., between about 35° C. and about 45° C., between about 35° C. and about 40° C., or between about 37° C. and about 40° C.

In some embodiments, the temperature set points of the fluidized beds (the temperature for each bed being selected independently from the temperature selected for another bed) is between about room temperature (e.g., USP room temperature (e.g., 21±4° C.)) and about 100° C., e.g., between about 30° C. and about 95° C., between about 40° C. and about 90° C., between about 50° C. and about 80° C., between about 60° C. and about 85° C., between about 65° C. and about 95° C., or between about 80° C. and about 95° C.

FSD can be performed on a mixture containing COMPOUND 2. For example, FSD can be performed on a mixture containing COMPOUND 2, and one or more polymer(s), and optionally one or more surfactant(s), and optionally one or more additional excipients(s)) to obtain a solid dispersion of amorphous COMPOUND 2 thereof, e.g., that can be directly compressed into an oral dosage form (e.g., tablet). Alternatively, the dispersion can be blended with one or more excipients prior to compression.

In one embodiment, the process for preparing a solid dispersion of COMPOUND 2 comprises:

a) forming a mixture of COMPOUND 2, one or more polymer(s), and one or more solvent(s); and b) rapidly removing the solvent(s) from the solution to form a solid amorphous dispersion comprising COMPOUND 2 and the one or more polymer(s). The one or more polymer(s) and one or more solvent(s) may be any of those disclosed herein.

In some embodiments, the solvent is removed by spray drying. In some embodiments the solid dispersion is tray dried using a convection tray dryer. In some embodiments, the solid dispersion is screened.

In one embodiment, COMPOUND 2 is crystalline. In another embodiment, COMPOUND 2 is amorphous.

As would be appreciated by one of skill in the art, spray drying may be done and is often done in the presence of an inert gas such as nitrogen. In certain embodiments, processes that involve spray drying may be done in the presence of a supercritical fluid involving carbon dioxide or a mixture including carbon dioxide.

In another embodiment, the process for preparing a solid dispersion of COMPOUND 2 comprises:

a) forming a mixture of COMPOUND 2, a polymer, and a solvent; and b) spray-drying the mixture to form a solid dispersion comprising COMPOUND 2 and the polymer.

Post-drying and/or polishing the wet spray dried dispersion to below ICH or given specifications for residual solvents can optionally be performed.

These processes may be used to prepare the pharmaceutical compositions disclosed herein. The amounts and the features of the components used in the processes may be as disclosed herein.

In some embodiments, the solvent comprises one or more volatile solvent(s) to dissolve or suspend COMPOUND 2 and the polymer(s). In some embodiments, the one or more solvent(s) completely dissolves COMPOUND 2 and the polymer(s).

In some embodiments, the one or more solvent(s) is a volatile solvent (e.g., methylene chloride, acetone, methanol, ethanol, chloroform, tetrahydrofuran (THF), or a mixture thereof). Examples of suitable volatile solvents include those that dissolve or suspend the therapeutically active compound either alone or in combination with another co-solvent. In some embodiments, the solvent(s) completely dissolves the therapeutically active compound. In some embodiments, the solvent is acetone. In some embodiments, the solvent is methanol.

In some embodiments, the solvent is a non-volatile solvent (e.g., organic acids such as glacial acetic acid, dimethyl sulfoxide (DMSO), dimethylformamide (DMF), or water). In some embodiments, a non-volatile solvent is a component in a solvent system. For example the non-volatile solvent is present as a component in a solvent from about 1% to about 20% w/w (e.g., from about 3% w/w to about 15% w/w, from about 4% w/w to about 12% w/w, or from about 5% w/w to about 10% w/w).

In some embodiments, the solvent is a mixture of solvents. For example, the solvent can include from about 0% to about 30% acetone and from about 70% to about 100% methanol, or the solvent can include from about 0% to about 40% acetone and from about 60% to about 100% methanol. Other exemplary ratios of methanol to acetone include 80:20, 75:25, 70:30, 60:40, 55:45, and 50:50.

In some embodiments, the solvent is a combination of solvents including at least one non-volatile solvent. For example, the solvent is a combination of components that includes both a volatile solvent and a non-volatile solvent. In some embodiments, the solvent system is a combination of a volatile solvent or combination of solvents such as methanol and acetone with a non-volatile solvent such as glacial acetic acid. For example, the solvent system comprises from about 40% to about 80% methanol, from about 20% to about 35% acetone, and from about 1% to about 15% glacial acetic acid (e.g., from about 50% to about 70% methanol, from about 25% to about 30% acetone, and from about 3% to about 12% glacial acetic acid).

In some embodiments, the solvent system is a combination of a volatile solvent or combination of solvents such as methanol and acetone with a non-volatile solvent such as water. For example, the solvent system comprises from about 40% to about 80% methanol, from about 20% to about 35% acetone, and from about 0.1% to about 15% water (e.g., from about 50% to about 70% methanol, from about 25% to about 30% acetone, and from about 1% to about 5% water).

In certain embodiments, the pharmaceutical compositions of the solid dispersion may be made by a process described herein. For example, a solid dispersion of: (a) COMPOUND 2 and (b) one or more polymer(s), and optionally one or more surfactant(s) and optionally one or more additional excipient(s).

Pharmaceutical Compositions Containing Solid Dispersions of COMPOUND 2

In certain embodiments, provided herein are pharmaceutical compositions, comprising: (a) a solid dispersion, comprising COMPOUND 2 and a polymer; and (b) one or more pharmaceutically acceptable carrier(s). Examples of pharmaceutically acceptable carriers are fillers, disintegrants, wetting agents, glidants, and lubricants.

In some embodiments, the pharmaceutical compositions may be orally administered in any orally acceptable dosage form including, but not limited to, capsules, tablets, emulsions and aqueous suspensions, dispersions and solutions.

In some embodiments the pharmaceutical composition is a tablet.

In some embodiments the pharmaceutical composition comprises a directly compressed dosage form of COMPOUND 2.

In some embodiments, the pharmaceutical composition also includes a filler. The filler can be, for example, microcrystalline cellulose, lactose, mannitol, ethyl cellulose, sorbitol, starch, sucrose, calcium phosphate, powdered cellulose, silicified microcrystalline cellulose, isomalt, or mixtures thereof. In some embodiments, the filler is microcrystalline cellulose.

In some embodiments, the filler is present in the pharmaceutical composition in an amount of between about 10% w/w and 50% w/w (e.g., between about 15% w/w and about 45% w/w; between about 20% w/w and about 40% w/w; between about 25% w/w and about 35% w/w; or between about 28% w/w and about 32% w/w). In some embodiments, the filler is present in the pharmaceutical composition in an amount of from about 20% w/w to about 35% w/w, for example from about 25% w/w to about 34% w/w, or from about 26% w/w to about 33% w/w, or from about 27% w/w to about 32% w/w, for example, about 28% w/w, about 28.5% w/w, about 29% w/w, about 29.5% w/w about 30% w/w, about 30.5% w/w, about 31% w/w, or about 31.5% w/w. In some embodiments, the filler is present in the pharmaceutical composition in an amount of about 29% w/w, about 29.1% w/w, about 29.2% w/w, about 29.3% w/w, about 29.4% w/w, about 29.5% w/w, about 29.6% w/w, about 29.7% w/w, about 29.8% w/w, about 29.9% w/w, or about 30% w/w. In some embodiments, the filler is present in the pharmaceutical composition in an amount of between about 25% w/w and about 35% w/w. In some embodiments, the filler is present in the pharmaceutical composition in an amount of about 29.5% w/w.

In some embodiments, the pharmaceutical composition also includes a disintegrant. The disintegrant can be, for example, colloidal silicon dioxide, powdered cellulose, calcium silicate, crospovidone, calcium alginate, methyl cellulose, chitosan, carboxy methyl cellulose, croscarmellose sodium, carboxymethyl starch, sodium alginate, sodium starch glycolate, pregelatinized starch, or mixtures thereof. In some embodiments, the disintegrant is croscarmellose sodium.

In some embodiments, the disintegrant is present in the pharmaceutical composition in an amount of between about 1% w/w and 15% w/w (e.g., between about 3% w/w and about 12% w/w; between about 4% w/w and about 10% w/w; between about 5% w/w and about 7% w/w; or between about 6% w/w and about 7% w/w). In some embodiments, the disintegrant is present in the pharmaceutical composition in an amount of about 3% w/w, about 3.5% w/w, about 4% w/w, about 49.5% w/w about 5% w/w, about 5.5% w/w, about 6% w/w, or about 6.5% w/w, about 7% w/w, about 7.5% w/w, about 8% w/w, about 8.5% w/w, about 9% w/w, about 9.5% w/w, or about 10% w/w. In some embodiments, the disintegrant is present in the pharmaceutical composition in an amount of between about 5% w/w and about 7% w/w. In some embodiments, the disintegrant is present in the pharmaceutical composition in an amount of about 6% w/w.

In some embodiments, the pharmaceutical composition also includes a wetting agent. The wetting agent can be, for example, sodium lauryl sulfate, sodium dodecyl sulfate, polysorbates (such as Tween 20 and Tween 80), poloxamers (such as Poloxamer 335 and Poloxamer 407), glyceryl monooleate, or mixtures thereof. In some embodiments, the wetting agent is sodium lauryl sulfate.

In some embodiments, the wetting agent is present in the pharmaceutical composition in an amount of between about 0.1% w/w and 2% w/w (e.g., between about 0.5% w/w and about 2% w/w; between about 0.5% w/w and about 1.5% w/w; or between about 1% w/w and about 1.5% w/w). In some embodiments, the wetting agent is present in the pharmaceutical composition in an amount of about 0.1% w/w, about 0.2% w/w, about 0.3% w/w, about 0.4% w/w about 0.5% w/w, about 0.6% w/w, about 0.7% w/w, or about 0.8% w/w, about 0.9% w/w, about 1% w/w, about 1.1% w/w, about 1.2% w/w, about 1.3% w/w, about 1.4% w/w, about 1.5% w/w, about 1.6% w/w, about 1.7% w/w, about 1.8% w/w, about 1.9% w/w, or about 2% w/w. In some embodiments, the wetting agent is present in the pharmaceutical composition in an amount of between about 0.5% w/w and about 1.5% w/w. In some embodiments, the wetting agent is present in the pharmaceutical composition in an amount of about 1% w/w.

In some embodiments, the pharmaceutical composition also includes a glidant. The glidant can be, for example, silicon dioxide, colloidal silicon dioxide, tribasic calcium phosphate, magnesium stearate, magnesium trisilicate, powdered cellulose, talc, starch, and mixtures thereof. In some embodiments, the glidant is colloidal silicon dioxide.

In some embodiments, the glidant is present in the pharmaceutical composition in an amount of between about 0.1% w/w and 5% w/w (e.g., between about 1% w/w and about 4% w/w; between about 1% w/w and about 3% w/w; or between about 1.5% w/w and about 2.5% w/w). In some embodiments, the glidant is present in the pharmaceutical composition in an amount of about 0.5% w/w, about 1% w/w, about 1.5% w/w, about 2% w/w about 2.5% w/w, about 3% w/w, about 3.5% w/w, or about 4% w/w, about 4.5% w/w, or about 5% w/w. In some embodiments, the glidant is present in the pharmaceutical composition in an amount of about 1.1% w/w, about 1.2% w/w, about 1.3% w/w, about 1.4% w/w, about 1.5% w/w, about 1.6% w/w, about 1.7% w/w, about 1.8% w/w, about 1.9% w/w, about 2% w/w, 2.1% w/w, about 2.2% w/w, about 2.3% w/w, about 2.4% w/w, about 2.5% w/w, about 2.6% w/w, about 2.7% w/w, about 2.8% w/w, about 2.9% w/w, or about 3% w/w. In some embodiments, the glidant is present in the pharmaceutical composition in an amount of between about 1% w/w and about 3% w/w. In some embodiments, the glidant is present in the pharmaceutical composition in an amount of about 2% w/w.

In some embodiments, the pharmaceutical composition also includes a lubricant. The lubricant can be, for example, magnesium stearate, talc, sodium stearyl fumarate, glyceryl behenate, hydrogenated vegetable oil, zinc stearate, calcium stearate, sucrose stearate, polyvinyl alcohol, magnesium lauryl sulfate, or mixtures thereof. In some embodiments, the lubricant is magnesium stearate.

In some embodiments, the lubricant is present in the pharmaceutical composition in an amount of between about 0.1% w/w and 5% w/w (e.g., between about 1% w/w and about 4% w/w; between about 1% w/w and about 3% w/w; or between about 1% w/w and about 2% w/w). In some embodiments, the lubricant is present in the pharmaceutical composition in an amount of about 0.5% w/w, about 1% w/w, about 1.5% w/w, about 2% w/w about 2.5% w/w, about 3% w/w, about 3.5% w/w, or about 4% w/w, about 4.5% w/w, or about 5% w/w. In some embodiments, the lubricant is present in the pharmaceutical composition in an amount of about 0.1% w/w, about 0.2% w/w, about 0.3% w/w, about 0.4% w/w, about 0.5% w/w, about 0.6% w/w, about 0.7% w/w, about 0.8% w/w, about 0.9% w/w, about 1% w/w, about 1.1% w/w, about 1.2% w/w, about 1.3% w/w, about 1.4% w/w, about 1.5% w/w, about 1.6% w/w, about 1.7% w/w, about 1.8% w/w, about 1.9% w/w, about 2% w/w, 2.1% w/w, about 2.2% w/w, about 2.3% w/w, about 2.4% w/w, or about 2.5% w/w. In some embodiments, the lubricant is present in the pharmaceutical composition in an amount of between about 0.5% w/w and about 2.5% w/w. In some embodiments, the lubricant is present in the pharmaceutical composition in an amount of about 1.5% w/w.

In some embodiments, the solid dispersion makes up about 25% to 85% by weight of the total weight of the pharmaceutical composition. In some embodiments, the solid dispersion makes up about 50% to about 70% by weight of the total weight of the pharmaceutical composition.

In some embodiments, the COMPOUND 2 makes up about 15% to 45% of the total weight of the pharmaceutical composition, and the one or more polymer(s) makes up about 15% to 45% of the total weight of the pharmaceutical composition.

In some embodiments, the COMPOUND 2 makes up about 20% w/w of the pharmaceutical composition, the one or more polymer(s) makes up about 40% w/w of the pharmaceutical composition.

In some embodiments, the COMPOUND 2 makes up about 25% w/w of the pharmaceutical composition, the one or more polymer(s) makes up about 35% w/w of the pharmaceutical composition.

In some embodiments, the COMPOUND 2 makes up about 30% w/w of the pharmaceutical composition, the one or more polymer(s) makes up about 30% w/w of the pharmaceutical composition.

In some embodiments, the COMPOUND 2 makes up about 35% w/w of the pharmaceutical composition, the one or more polymer(s) makes up about 25% w/w of the pharmaceutical composition.

In some embodiments, the solid dispersion makes up from between about 50% w/w to about 70% w/w of the pharmaceutical composition, the filler makes up from between about 25% w/w to about 35% w/w of the pharmaceutical composition, the disintegrant makes up from between about 5% w/w to about 7% w/w of the pharmaceutical composition, the wetting agent makes up from between about 0.5% w/w to about 1.5% w/w of the pharmaceutical composition, the glidant makes up from between about 1% w/w to about 3% w/w of the pharmaceutical composition, the lubricant makes up from between about 0.5% w/w to about 2.5% w/w of the pharmaceutical composition thereby totaling 100% by weight of the composition.

In some embodiments, the solid dispersion makes up about 60% w/w of the pharmaceutical composition, the filler makes up about 29.5% w/w of the pharmaceutical composition, the disintegrant makes up about 6% w/w of the pharmaceutical composition, the wetting agent makes up about 1% w/w of the pharmaceutical composition, the glidant makes up about 2% w/w of the pharmaceutical composition, the lubricant makes up about 1.5% w/w of the pharmaceutical composition.

In some embodiments, the pharmaceutical composition comprises, from between about 25% w/w to about 35% w/w of COMPOUND 2 from between about 25% w/w to about 35% w/w of hypromellose acetate succinate (HPMCAS), from between about 25% w/w to about 35% w/w of microcrystalline cellulose, from between about 5% w/w to about 7% w/w croscarmellose sodium, from between about 0.5% w/w to about 1.5% w/w sodium lauryl sulfate, about from between about 1% w/w to about 3% w/w colloidal silicon dioxide, and rom between about 0.5% w/w to about 2.5% w/w of magnesium stearate, thereby totaling 100% by weight of the composition.

In some embodiments, the pharmaceutical composition comprises, about 30% w/w of COMPOUND 2 about 30% w/w of hypromellose acetate succinate (HPMCAS), about 29.5% w/w of microcrystalline cellulose, about 6% w/w croscarmellose sodium, about 1% w/w sodium lauryl sulfate, about 2% w/w colloidal silicon dioxide, and about 1.5% w/w of magnesium stearate.

In some embodiments, the solid dispersion, filler, disintegrant, wetting agent, glidant, and lubricant are added intragranularly. In some embodiments, an additional amount of the filler, disintegrant, glidant, and lubricant are added extragranularly.

In some embodiments, the pharmaceutical composition comprises, the following intragranularly added components: the solid dispersion makes up from about 50% w/w to about 70% w/w of the pharmaceutical composition, the filler makes up from about 18% w/w to about 26% w/w of the pharmaceutical composition, disintegrant makes up from about 2% w/w to about 6% w/w of the pharmaceutical composition, wetting agent makes up from about 0.5% w/w to about 1.5% w/w of the pharmaceutical composition, glidant makes up from about 0.5% w/w to about 1.5% w/w of the pharmaceutical composition, and lubricant makes up from about 0.25% w/w to about 1% w/w of the pharmaceutical composition.

In some embodiments, a the pharmaceutical composition comprises the following extragranularly added components: an additional amount of the filler makes up from about 4% w/w to about 12% w/w of the pharmaceutical composition, an additional amount of the disintegrant makes up from about 1% w/w to about 3% w/w of the pharmaceutical composition, an additional amount of the glidant makes up from about 0.5% w/w to about 1.5% w/w of the pharmaceutical composition, and an additional amount of the lubricant makes up from about 0.5% w/w to about 1.5% w/w of the pharmaceutical composition, and are added extragranularly.

In some embodiments, the pharmaceutical composition comprises, the following intragranularly added components: the solid dispersion makes up about 60% w/w of the pharmaceutical composition, the filler makes up about 21.5% w/w of the pharmaceutical composition, disintegrant makes up about 4% w/w of the pharmaceutical composition, wetting agent makes up about 1% w/w of the pharmaceutical composition, glidant makes up about 1% w/w of the pharmaceutical composition, and lubricant makes up about 0.5% w/w of the pharmaceutical composition.

In some embodiments, a the pharmaceutical composition comprises the following extragranularly added components: an additional amount of the filler makes up about 8% w/w of the pharmaceutical composition, an additional amount of the disintegrant makes up about 2% w/w of the pharmaceutical composition, an additional amount of the glidant makes up about 1% w/w of the pharmaceutical composition, and an additional amount of the lubricant makes up about 1% w/w of the pharmaceutical composition, and are added extragranularly.

In some embodiments, the pharmaceutical composition comprises, the following intragranularly added components: the solid dispersion comprising COMPOUND 2 and hypromellose acetate succinate (HPMCAS), makes up from about 50% w/w to about 70% w/w of the pharmaceutical composition, microcrystalline cellulose makes up from about 18% w/w to about 26% w/w of the pharmaceutical composition, croscarmellose sodium makes up from about 2% w/w to about 6% w/w of the pharmaceutical composition, sodium lauryl sulfate makes up from about 0.5% w/w to about 1.5% w/w of the pharmaceutical composition, colloidal silicon dioxide makes up from about 0.5% w/w to about 1.5% w/w of the pharmaceutical composition, and magnesium stearate makes up from about 0.25% w/w to about 1% w/w of the pharmaceutical composition.

In some embodiments, a the pharmaceutical composition comprises the following extragranularly added components: an additional amount of microcrystalline cellulose makes up from about 4% w/w to about 12% w/w of the pharmaceutical composition, an additional amount of croscarmellose sodium makes up from about 1% w/w to about 3% w/w of the pharmaceutical composition, an additional amount of colloidal silicon dioxide makes up from about 0.5% w/w to about 1.5% w/w of the pharmaceutical composition, and an additional amount of magnesium stearate makes up from about 0.5% w/w to about 1.5% w/w of the pharmaceutical composition, and are added extragranularly.

In some embodiments, the pharmaceutical composition comprises, the following intragranularly added components: the solid dispersion comprising COMPOUND 2 and hypromellose acetate succinate (HPMCAS), makes up about 60% w/w of the pharmaceutical composition, microcrystalline cellulose makes up about 21.5% w/w of the pharmaceutical composition, croscarmellose sodium makes up about 4% w/w of the pharmaceutical composition, sodium lauryl sulfate makes up about 1% w/w of the pharmaceutical composition, colloidal silicon dioxide makes up about 1% w/w of the pharmaceutical composition, and magnesium stearate makes up about 0.5% w/w of the pharmaceutical composition.

In some embodiments, a the pharmaceutical composition comprises the following extragranularly added components: an additional amount of microcrystalline cellulose makes up about 8% w/w of the pharmaceutical composition, an additional amount of croscarmellose sodium makes up about 2% w/w of the pharmaceutical composition, an additional amount of colloidal silicon dioxide makes up about 1% w/w of the pharmaceutical composition, and an additional amount of magnesium stearate makes up about 1% w/w of the pharmaceutical composition, and are added extragranularly.

Methods of Use

In certain embodiments, the inhibitory activity of COMPOUND 2 against IDH1 mutants (e.g., IDH1 R132H, IDH1 R132C, IDH1 R132L, IDH1 R132V, IDH1 R132S or IDH1 R132GF) can be tested by methods described in Example A of PCT Publication No. WO 2013/107291 and US Publication No. US 2013/0190249, hereby incorporated by reference in their entireties, or analogous methods.

In one embodiment, provided herein is a method of treating hematological malignancies by administering to a subject a combination of a mutant IDH1 inhibitor and a DNA demethylating agent. In one embodiment, the hematologic malignancy is an advanced hematologic malignancy.

In one embodiment, provided herein is a method of treating solid tumors by administering to a subject a combination of a mutant IDH1 inhibitor and a DNA demethylating agent.

In one embodiment, the mutant IDH1 inhibitor is COMPOUND 2.

In one embodiment, the DNA demethylating agent is azacitidine.

In one embodiment, provided herein is a method of treating hematologic malignancies, such as acute myelogenous leukemia (AML), myelodysplastic syndrome (MDS), myeloproliferative neoplasms (MPN), chronic myelomonocytic leukemia (CMML), B-acute lymphoblastic leukemias (B-ALL), or lymphoma (e.g., T-cell lymphoma), each characterized by the presence of a mutant allele of IDH1, comprising administering to a subject a therapeutically effective amount of
COMPOUND 2 and azacitidine. In one embodiment, the hematologic malignancy is an advanced hematologic malignancy.

In one embodiment, provided herein is a method of treating hematologic malignancies, such as acute myelogenous leukemia (AML), myelodysplastic syndrome (MDS), myeloproliferative neoplasms (MPN), chronic myelomonocytic leukemia (CMML), B-acute lymphoblastic leukemias (B-ALL), or lymphoma (e.g., T-cell lymphoma), each characterized by the presence of a mutant allele of IDH1, comprising administering to a subject a therapeutically effective amount of COMPOUND 2, or a solid suspension thereof, and azacitidine. In one embodiment, the hematologic malignancy is an advanced hematologic malignancy.

In one embodiment, provided herein is a methods of treating hematologic malignancies, such as acute myelogenous leukemia (AML), myelodysplastic syndrome (MDS), myeloproliferative neoplasms (MPN), chronic myelomonocytic leukemia (CMML), B-acute lymphoblastic leukemias (B-ALL), or lymphoma (e.g., T-cell lymphoma), each characterized by the presence of a mutant allele of IDH1, comprising administering to a subject a therapeutically effective amount of a single crystalline form of COMPOUND 2 and azacitidine. In one embodiment, the single crystalline form of COMPOUND 2 is any percentage between 90% and 100% pure. In one embodiment, the hematologic malignancy is an advanced hematologic malignancy.

In one embodiment, provided herein is a method of treating hematologic malignancies, such as acute myelogenous leukemia (AML), myelodysplastic syndrome (MDS), myeloproliferative neoplasms (MPN), chronic myelomonocytic leukemia (CMML), B-acute lymphoblastic leukemias (B-ALL), or lymphoma (e.g., T-cell lymphoma), each characterized by the presence of a mutant allele of IDH1, comprising administering to a subject a pharmaceutical composition comprising a therapeutically effective amount of COMPOUND 2 and azacitidine. In one embodiment, the hematologic malignancy is an advanced hematologic malignancy.

In one embodiment, provided herein is a method of treating an hematologic malignancy, such as acute myelogenous leukemia (AML), myelodysplastic syndrome (MDS), myeloproliferative neoplasms (MPN), chronic myelomonocytic leukemia (CMML), B-acute lymphoblastic leukemias (B-ALL), or lymphoma (e.g., T-cell lymphoma), each characterized by the presence of a mutant allele of IDH1, comprising administering to a subject a pharmaceutical composition comprising a therapeutically effective amount of a single crystalline form of COMPOUND 2 and azacitidine. In one embodiment, the single crystalline form of COMPOUND 2 is any percentage between 90% and 100% pure. In one embodiment, the hematologic malignancy is an advanced hematologic malignancy.

In one embodiment, provided herein is a method of treating a solid tumor, such as glioma, melanoma, chondrosarcoma, cholangiocarcinoma, sarcoma, or non-small cell lung cancer, each characterized by the presence of a mutant allele of IDH1, comprising administering to a subject a therapeutically effective amount of COMPOUND 2, or a crystalline form thereof, and azacitidine.

In one embodiment, provided herein is a method of treating a solid tumor, such as glioma, melanoma, chondrosarcoma, cholangiocarcinoma, sarcoma, or non-small cell lung cancer, each characterized by the presence of a mutant allele of IDH1, comprising administering to a subject a therapeutically effective amount of COMPOUND 2 and azacitidine.

In one embodiment, provided herein is a method of treating a solid tumor, such as glioma, melanoma, chondrosarcoma, cholangiocarcinoma (including intrahepatic cholangiocarcinoma (IHCC), prostate cancer, colon cancer, or non-small cell lung cancer (NSCLC), each characterized by the presence of a mutant allele of IDH1, comprising administering to a subject a therapeutically effective amount of COMPOUND 2, or a solid suspension thereof, and azacitidine.

In one embodiment, provided herein is a methods of treating a solid tumor, such as glioma, melanoma, chondrosarcoma, cholangiocarcinoma (including intrahepatic cholangiocarcinoma (IHCC), prostate cancer, colon cancer, or non-small cell lung cancer (NSCLC), each characterized by the presence of a mutant allele of IDH1, comprising administering to a subject a therapeutically effective amount of a single crystalline form of COMPOUND 2 and azacitidine. In one embodiment, the single crystalline form of COMPOUND 2 is any percentage between 90% and 100% pure.

In one embodiment, provided herein is a method of treating a solid tumor, such as glioma, melanoma, chondrosarcoma, cholangiocarcinoma (including intrahepatic cholangiocarcinoma (IHCC), prostate cancer, colon cancer, or non-small cell lung cancer (NSCLC), each characterized by the presence of a mutant allele of IDH1, comprising administering to a subject a pharmaceutical composition comprising a therapeutically effective amount of COMPOUND 2 and azacitidine.

In one embodiment, provided herein is a method of treating a solid tumor, such as glioma, melanoma, chondrosarcoma, cholangiocarcinoma (including intrahepatic cholangiocarcinoma (IHCC), prostate cancer, colon cancer, or non-small cell lung cancer (NSCLC), each characterized by the presence of a mutant allele of IDH1, comprising administering to a subject a pharmaceutical composition comprising a therapeutically effective amount of a single crystalline form of COMPOUND 2 and azacitidine. In one embodiment, the single crystalline form of COMPOUND 2 is any percentage between 90% and 100% pure.

In one embodiment, the malignancy to be treated is characterized by a mutant allele of IDH1, wherein the IDH1 mutation results in a new ability of the enzyme to catalyze the NAPH dependent reduction of a ketoglutarate to R( ) 2 hydroxyglutarate in a patient. In one aspect of this embodiment, the mutant IDH1 has an R132X mutation. In one aspect of this embodiment, the R132X mutation is selected from R132H, R132C, R132L, R132V, R132S and R132G. In another aspect, the R132X mutation is R132H or R132C. In yet another aspect, the R132X mutation is R132H.

A malignancy can be analyzed by sequencing cell samples to determine the presence and specific nature of (e.g., the changed amino acid present at) a mutation at amino acid 132 of IDH1.

Without being bound by theory, applicants believe that mutant alleles of IDH1 wherein the IDH1 mutation results in a new ability of the enzyme to catalyze the NAPH-dependent reduction of α-ketoglutarate to R(−)-2-hydroxyglutarate, and in particular R132H mutations of IDH1, characterize a subset of all types of cancers, without regard to their cellular nature or location in the body. Thus, the compounds, and methods desribed herein are useful to treat an hematologic malignancy, including an advanced hematologic malignancy, such as acute myelogenous leukemia (AML), myelodysplastic syndrome (MDS), myeloproliferative neoplasms (MPN), chronic myelomonocytic leukemia (CMML), B-acute lymphoblastic leukemias (B-ALL), or lymphoma (e.g., T-cell lymphoma), each characterized by the presence of a mutant allele of IDH1 imparting such activity and in particular an IDH1 R132H or R132C mutation. In another aspect, the compounds, and methods desribed herein are useful to treat a solid tumor, such as glioma, melanoma, chondrosarcoma, cholangiocarcinoma (including intrahepatic cholangiocarcinoma (IHCC), prostate cancer, colon cancer, or non-small cell lung cancer (NSCLC), each characterized by the presence of a mutant allele of IDH1 imparting such activity and in particular an IDH1 R132H or R132C mutation.

In one embodiment the malignancy is a tumor wherein at least 30, 40, 50, 60, 70, 80 or 90% of the tumor cells carry an IDH1 mutation, and in particular an an IDH1 R132H or R132C mutation, at the time of diagnosis or treatment.

In one embodiment, the efficacy of treatment of malignancy is monitored by measuring the levels of 2HG in the subject. Typically levels of 2HG are measured prior to treatment, wherein an elevated level is indicated for the use of COMPOUND 2. Once the elevated levels are established, the level of 2HG is determined during the course of and/or following termination of treatment to establish efficacy. In certain embodiments, the level of 2HG is only determined during the course of and/or following termination of treatment. A reduction of 2HG levels during the course of treatment and following treatment is indicative of efficacy. Similarly, a determination that 2HG levels are not elevated during the course of or following treatment is also indicative of efficacy. Typically, 2HG measurements are utilized together with other well-known determinations of efficacy of malignancy treatment, such as reduction in number and size of tumors and/or other cancer-associated lesions, improvement in the general health of the subject, and alterations in other biomarkers that are associated with malignancy treatment efficacy.

2HG can be detected in a sample by the methods of PCT Publication No. WO 2011/050210 and US Publication No. US2012/0121515 hereby incorporated by reference in their entirety, or by analogous methods. In an exemplary method, 2HG can be detected in a sample by LC/MS. The sample is mixed 80:20 with methanol, and centrifuged at 3,000 rpm for 20 minutes at 4 degrees Celsius. The resulting supernatant can be collected and stored at −80 degrees Celsius prior to LC-MS/MS to assess 2-hydroxyglutarate levels. A variety of different liquid chromatography (LC) separation methods can be used. Each method can be coupled by negative electrospray ionization (ESI, −3.0 kV) to triple-quadrupole mass spectrometers operating in multiple reaction monitoring (MRM) mode, with MS parameters optimized on infused metabolite standard solutions. Metabolites can be separated by reversed phase chromatography using 10 mM tributyl-amine as an ion pairing agent in the aqueous mobile phase, according to a variant of a previously reported method (Luo et al. *J Chromatogr A* 1147, 153-64, 2007). One method allows resolution of TCA metabolites: t=0, 50% B; t=5, 95% B; t=7, 95% B; t=8, 0% B, where B refers to an organic mobile phase of 100% methanol. Another method is specific for 2-hydroxyglutarate, running a fast linear gradient from 50%-95% B (buffers as defined above) over 5 minutes. A Synergi Hydro-RP, 100 mm×2 mm, 2.1 μm particle size (Phenomonex) can be used as the column, as described above. Metabolites can be quantified by comparison of peak areas with pure metabolite standards at known concentration. Metabolite flux studies from $^{13}$C-glutamine can be performed as described, e.g., in Munger et al. Nat Biotechnol 26, 1179-86, 2008.

In one embodiment, 2HG is directly evaluated.

In another embodiment, a derivative of 2HG formed in process of performing the analytic method is evaluated. By way of example such a derivative can be a derivative formed in MS analysis. Derivatives can include a salt adduct, e.g., a Na adduct, a hydration variant, or a hydration variant which is also a salt adduct, e.g., a Na adduct, e.g., as formed in MS analysis.

In another embodiment a metabolic derivative of 2HG is evaluated. Examples include species that build up or are elevated, or reduced, as a result of the presence of 2HG, such as glutarate or glutamate that will be correlated to 2HG, e.g., R-2HG.

Exemplary 2HG derivatives include dehydrated derivatives such as the compounds provided below or a salt adduct thereof:

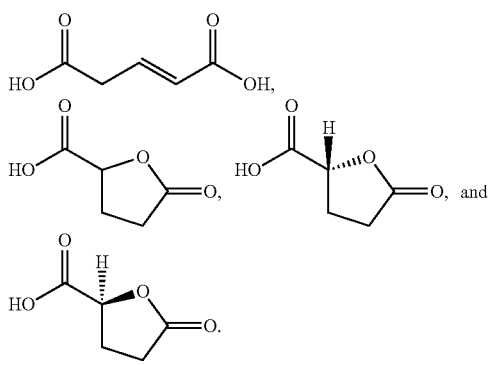

2HG is known to accumulate in the inherited metabolic disorder 2-hydroxyglutaric aciduria. This disease is caused by deficiency in the enzyme 2-hydroxyglutarate dehydrogenase, which converts 2HG to α-KG (Struys, E. A. et al. Am J Hum Genet 76, 358-60 (2005)). Patients with 2-hydroxyglutarate dehydrogenase deficiencies accumulate 2HG in the brain as assessed by MRI and CSF analysis, develop leukoencephalopathy, and have an increased risk of developing brain tumors (Aghili, M., Zahedi, F. & Rafiee, *J Neurooncol* 91, 233-6 (2009); Kolker, S., Mayatepek, E. & Hoffmann, G. F. *Neuropediatrics* 33, 225-31 (2002); Wajner, M., Latini, A., Wyse, A. T. & Dutra-Filho, C. S. *J Inherit Metab Dis* 27, 427-48 (2004)). Furthermore, elevated brain levels of 2HG result in increased ROS levels (Kolker, S. et al. *Eur J Neurosci* 16, 21-8 (2002); Latini, A. et al. *Eur J Neurosci* 17, 2017-22 (2003)), potentially contributing to an increased risk of cancer. The ability of 2HG to act as an NMDA receptor agonist may contribute to this effect (Kolker, S. et al. *Eur J Neurosci* 16, 21-8 (2002)). 2HG may also be toxic to cells by competitively inhibiting glutamate and/or αKG utilizing enzymes. These include transaminases which allow utilization of glutamate nitrogen for amino and nucleic acid biosynthesis, and αKG-dependent prolyl hydroxylases such as those which regulate Hifl-alpha levels.

Thus, according to another embodiment, provided herein is a method of treating 2-hydroxyglutaric aciduria, particularly D-2-hydroxyglutaric aciduria, in a subject by administering to the subject COMPOUND 2 and azacitidine.

Treatment methods described herein can additionally comprise various evaluation steps prior to and/or following treatment with COMPOUND 2 and azacitidine.

In one embodiment, prior to and/or after treatment with COMPOUND 2 and azacitidine, the method further comprises the step of evaluating the growth, size, weight, invasiveness, stage and/or other phenotype of the malignancy.

In one embodiment, prior to and/or after treatment with COMPOUND and azacitidine, the method further comprises the step of evaluating the IDH1 genotype of the malignancy. This may be achieved by ordinary methods in the art, such as DNA sequencing, immuno analysis, and/or evaluation of the presence, distribution or level of 2HG.

In one embodiment, prior to and/or after treatment with COMPOUND 2 and azacitidine, the method further comprises the step of determining the 2HG level in the subject. This may be achieved by spectroscopic analysis, e.g., magnetic resonance-based analysis, e.g., MRI and/or MRS measurement, sample analysis of bodily fluid, such as serum or spinal cord fluid analysis, or by analysis of surgical material, e.g., by mass-spectroscopy.

In one embodiment, COMPOUND 2 and azacitidine are administered concurrently. In one embodiment, COMPOUND 2 and azacitidine are administered sequentially.

In one embodiment, depending on the disease to be treated and the subject's condition, COMPOUND 2 may be administered by oral, parenteral (e.g., intramuscular, intraperitoneal, intravenous, CIV, intracisternal injection or infusion, subcutaneous injection, or implant), inhalation, nasal, vaginal, rectal, sublingual, or topical (e.g., transdermal or local) routes of administration. COMPOUND 2 may be formulated alone or together with one or more active agent(s), in suitable dosage unit with pharmaceutically acceptable excipients, carriers, adjuvants and vehicles, appropriate for each route of administration.

In one embodiment, the amount of COMPOUND 2 administered in the methods provided herein may range, e.g., between about 5 mg/day and about 2,000 mg/day. In one embodiment, the range is between about 10 mg/day and about 2,000 mg/day. In one embodiment, the range is between about 20 mg/day and about 2,000 mg/day. In one embodiment, the range is between about 50 mg/day and about 1,000 mg/day. In one embodiment, the range is between about 100 mg/day and about 1,000 mg/day. In one embodiment, the range is between about 100 mg/day and about 500 mg/day. In one embodiment, the range is between about 150 mg/day and about 500 mg/day. In one embodiment, the range is or between about 150 mg/day and about 250 mg/day. In certain embodiments, particular dosages are, e.g., about 10 mg/day. In one embodiment, the dose is about 20 mg/day. In one embodiment, the dose is about 50 mg/day. In one embodiment, the dose is about 75 mg/day. In one embodiment, the dose is about 100 mg/day. In one embodiment, the dose is about 120 mg/day. In one embodiment, the dose is about 150 mg/day. In one embodiment, the dose is about 200 mg/day. In one embodiment, the dose is about 250 mg/day. In one embodiment, the dose is about 300 mg/day. In one embodiment, the dose is about 350 mg/day. In one embodiment, the dose is about 400 mg/day. In one embodiment, the dose is about 450 mg/day. In one embodiment, the dose is about 500 mg/day. In one embodiment, the dose is about 600 mg/day. In one embodiment, the dose is about 700 mg/day. In one embodiment, the dose is about 800 mg/day. In one embodiment, the dose is about 900 mg/day. In one embodiment, the dose is about 1,000 mg/day. In one embodiment, the dose is about 1,200 mg/day. In one embodiment, the dose is or about 1,500 mg/day. In certain embodiments, particular dosages are, e.g., up to about 10 mg/day. In one embodiment, the particular dose is up to about 20 mg/day. In one embodiment, the particular dose is up to about 50 mg/day. In one embodiment, the particular dose is up to about 75 mg/day. In one embodiment, the particular dose is up to about 100 mg/day. In one embodiment, the particular dose is up to about 120 mg/day. In one embodiment, the particular dose is up to about 150 mg/day. In one embodiment, the particular dose is up to about 200 mg/day. In one embodiment, the particular dose is up to about 250 mg/day. In one embodiment, the particular dose is up to about 300 mg/day. In one embodiment, the particular dose is up to about 350 mg/day. In one embodiment, the particular dose is up to about 400 mg/day. In one embodiment, the particular dose is up to about 450 mg/day. In one embodiment, the particular dose is up to about 500 mg/day. In one embodiment, the particular dose is up to about 600 mg/day. In one embodiment, the particular dose is up to about 700 mg/day. In one embodiment, the particular dose is up to about 800 mg/day. In one embodiment, the particular dose is up to about 900 mg/day. In one embodiment, the particular dose is up to about 1,000 mg/day. In one embodiment, the particular dose is up to about 1,200 mg/day. In one embodiment, the particular dose is up to about 1,500 mg/day.

In one embodiment, the amount of COMPOUND 2 in the pharmaceutical composition or dosage form provided herein may range, e.g., between about 5 mg and about 2,000 mg. In one embodiment, the range is between about 10 mg and about 2,000 mg. In one embodiment, the range is between about 20 mg and about 2,000 mg. In one embodiment, the range is between about 50 mg and about 1,000 mg. In one embodiment, the range is between about 50 mg and about 500 mg. In one embodiment, the range is between about 50 mg and about 250 mg. In one embodiment, the range is between about 100 mg and about 500 mg. In one embodiment, the range is between about 150 mg and about 500 mg. In one embodiment, the range is between about 150 mg and about 250 mg. In certain embodiments, particular amounts are, e.g., about 10 mg. In one embodiment, the particular amount is about 20 mg. In one embodiment, the particular amount is about 50 mg. In one embodiment, the particular amount is about 75 mg. In one embodiment, the particular amount is about 100 mg. In one embodiment, the particular amount is about 120 mg. In one embodiment, the particular amount is about 150 mg. In one embodiment, the particular amount is about 200 mg. In one embodiment, the particular amount is about 250 mg. In one embodiment, the particular amount is about 300 mg. In one embodiment, the particular amount is about 350 mg. In one embodiment, the particular amount is about 400 mg. In one embodiment, the particular amount is about 450 mg. In one embodiment, the particular amount is about 500 mg. In one embodiment, the particular amount is about 600 mg. In one embodiment, the particular amount is about 700 mg. In one embodiment, the particular amount is about 800 mg. In one embodiment, the particular amount is about 900 mg. In one embodiment, the particular amount is about 1,000 mg. In one embodiment, the particular amount is about 1,200 mg. In one embodiment, the particular amount is or about 1,500 mg. In certain embodiments, particular amounts are, e.g., up to about 10 mg. In one embodiment, the particular amount is up to about 20 mg. In one embodiment, the particular amount is up to about 50 mg. In one embodiment, the particular amount is up to about 75 mg. In one embodiment, the particular amount is up to about 100 mg. In one embodiment, the particular amount is up to about 120 mg. In one embodiment, the particular amount is up to about 150 mg. In one embodiment, the particular amount is up to about 200 mg. In one embodiment, the particular amount is up to about 250 mg. In one embodiment, the particular amount is up to about 300 mg. In one embodiment, the particular amount is up to about 350 mg. In one embodiment, the particular amount is up to about 400 mg. In one embodiment, the particular amount is up to about 450 mg. In one embodiment, the particular amount is up to about 500 mg. In one embodiment, the particular amount is up to about 600 mg. In one embodiment, the particular amount is up to about 700 mg. In one embodiment, the particular amount is up to about 800 mg. In one embodiment, the particular amount is up to about 900 mg. In one embodiment, the particular amount is up to about 1,000 mg. In one embodiment, the particular amount is up to about 1,200 mg. In one embodiment, the particular amount is up to about 1,500 mg.

In one embodiment, COMPOUND 2 can be delivered as a single dose such as, e.g., a single bolus injection, or oral tablets or pills; or over time such as, e.g., continuous infusion over time or divided bolus doses over time. In one embodiment, compound 1 can be administered repetitively if necessary, for example, until the patient experiences stable disease or regression, or until the patient experiences disease progression or unacceptable toxicity. Stable disease or lack thereof is determined by methods known in the art such as evaluation of patient's symptoms, physical examination, visualization of the tumor that has been imaged using X-ray, CAT, PET, or MRI scan and other commonly accepted evaluation modalities.

In certain embodiments, COMPOUND 2 is administered to a patient in cycles (e.g., daily administration for one week, then a rest period with no administration for up to three weeks). Cycling therapy involves the administration of an active agent for a period of time, followed by a rest for a period of time, and repeating this sequential administration. Cycling therapy can reduce the development of resistance, avoid or reduce the side effects, and/or improves the efficacy of the treatment.

In one embodiment, a method provided herein comprises administering COMPOUND 2 in 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, or greater than 40 cycles. In one embodiment, the median number of cycles administered in a group of patients is about 1. In one embodiment, the median number of cycles administered in a group of patients is about 2. In one embodiment, the median number of cycles administered in a group of patients is about 3. In one embodiment, the median number of cycles administered in a group of patients is about 4. In one embodiment, the median number of cycles administered in a group of patients is about 5. In one embodiment, the median number of cycles administered in a group of patients is about 6. In one embodiment, the median number of cycles administered in a group of patients is about 7. In one embodiment, the median number of cycles administered in a group of patients is about 8. In one embodiment, the median number of cycles administered in a group of patients is about 9. In one embodiment, the median number of cycles administered in a group of patients is about 10. In one embodiment, the median number of cycles administered in a group of patients is about 11. In one embodiment, the median number of cycles administered in a group of patients is about 12. In one embodiment, the median number of cycles administered in a group of patients is about 13. In one embodiment, the median number of cycles administered in a group of patients is about 14. In one embodiment, the median number of cycles administered in a group of patients is about 15. In one embodiment, the median number of cycles administered in a group of patients is about 16. In one embodiment, the median number of cycles administered in a group of patients is about 17. In one embodiment, the median number of cycles administered in a group of patients is about 18. In one embodiment, the median number of cycles administered in a group of patients is about 19. In one embodiment, the median number of cycles administered in a group of patients is about 20. In one embodiment, the median number of cycles administered in a group of patients is about 21. In one embodiment, the median number of cycles administered in a group of patients is about 22. In one embodiment, the median number of cycles administered in a group of patients is about 23. In one embodiment, the median number of cycles administered in a group of patients is about 24. In one embodiment, the median number of cycles administered in a group of patients is about 25. In one embodiment, the median number of cycles administered in a group of patients is about 26. In one embodiment, the median number of cycles administered in a group of patients is about 27. In one embodiment, the median number of cycles administered in a group of patients is about 28. In one embodiment, the median number of cycles administered in a group of patients is about 29. In one embodiment, the median number of cycles administered in a group of patients is about 30. In one embodiment, the median number of cycles administered in a group of patients is greater than about 30 cycles.

In certain embodiments, treatment cycles comprise multiple doses of COMPOUND 2 administered to a subject in need thereof over multiple days (e.g., 1, 2, 3, 4, 5, 6, 7, 8, 9, 10, 11, 12, 13, 14, or greater than 14 days), optionally followed by treatment dosing holidays (e.g., 1, 2, 3, 4, 5, 6, 7, 8, 9, 10, 11, 12, 13, 14, 15, 16, 17, 18, 19, 20, 21, 22, 23, 24, 25, 26, 27, 28, or greater than 28 days).

In one embodiment, depending on the disease to be treated and the subject's condition, azacitidine may be administered by oral, parenteral (e.g., intramuscular, intraperitoneal, intravenous, CIV, intracisternal injection or infusion, subcutaneous injection, or implant), inhalation, nasal, vaginal, rectal, sublingual, or topical (e.g., transdermal or local) routes of administration. Azacitidine may be formulated, alone or together with COMPOUND 2 and/or one or more active agent(s), in suitable dosage unit with pharmaceutically acceptable excipients, carriers, adjuvants and vehicles, appropriate for each route of administration.

In one embodiment, azacitidine is administered by, e.g., intravenous (IV), subcutaneous (SC) or oral routes. Certain embodiments herein provide co-administration of azacitidine with COMPOUND 2 and/or one or more additional active agents to provide a synergistic therapeutic effect in subjects in need thereof. The co-administered active agent(s) may be cancer therapeutic agents, as described herein. In certain embodiments, the co-administered active agent(s) may be inhibitors of IDH1. In certain embodiments, the co-administered agent(s) may be dosed, e.g., orally or by injection (e.g., IV or SC).

In certain embodiments, treatment cycles comprise multiple doses of azacitidine administered to a subject in need thereof over multiple days (e.g., 1, 2, 3, 4, 5, 6, 7, 8, 9, 10, 11, 12, 13, 14, or greater than 14 days), optionally followed by treatment dosing holidays (e.g., 1, 2, 3, 4, 5, 6, 7, 8, 9, 10, 11, 12, 13, 14, 15, 16, 17, 18, 19, 20, 21, 22, 23, 24, 25, 26, 27, 28, or greater than 28 days). Suitable dosage amounts for the methods provided herein include, e.g., therapeutically effective amounts and prophylactically effective amounts. For example, in certain embodiments, the amount of azacitidine administered in the methods provided herein may range, e.g., between about 50 $mg/m^2$/day and about 2,000 $mg/m^2$/day. In certain embodiments, the amount of azacitidine is between about 100 $mg/m^2$/day and about 1,000 $mg/m^2$/day. In certain embodiments, the amount of azacitidine is between about 100 $mg/m^2$/day and about 500 $mg/m^2$/day. In certain embodiments, the amount of azacitidine is between about 50 $mg/m^2$/day and about 500 $mg/m^2$/day. In certain embodiments, the amount of azacitidine is between about 50 $mg/m^2$/day and about 200 $mg/m^2$/day. In certain embodiments, the amount of azacitidine is between about 50 $mg/m^2$/day and about 100 $mg/m^2$/day. In certain embodiments, the amount of azacitidine is between about 50 $mg/m^2$/day and about 75 $mg/m^2$/day. In certain embodiments, the amount of azacitidine is between about 120 $mg/m^2$/day and about 250 $mg/m^2$/day. In certain embodiments, the particular dosage is about 50 $mg/m^2$/day. In one embodiment, the particular dosage is about 60 $mg/m^2$/day. In one embodiment, the particular dosage is about 75 $mg/m^2$/day. In one embodiment, the particular dosage is about 80 $mg/m^2$/day. In one embodiment, the particular dosage is about 100 $mg/m^2$/day. In one embodiment, the particular dosage is about 120 $mg/m^2$/day. In one embodiment, the particular dosage is about 140 $mg/m^2$/day. In one embodiment, the particular dosage is about 150 $mg/m^2$/day. In one embodiment, the particular dosage is about 180 $mg/m^2$/day. In one embodiment, the particular dosage is about 200 $mg/m^2$/day. In one embodiment, the particular dosage is about 220 $mg/m^2$/day. In one embodiment, the particular dosage is about 240 $mg/m^2$/day. In one embodiment, the particular dosage is about 250 $mg/m^2$/day. In one embodiment, the particular dosage is about 260 $mg/m^2$/day. In one embodiment, the particular dosage is about 280 $mg/m^2$/day. In one embodiment, the particular dosage is about 300 $mg/m^2$/day. In one embodiment, the particular dosage is about 320 $mg/m^2$/day. In one embodiment, the particular dosage is about 350 $mg/m^2$/day. In one embodiment, the particular dosage is about 380 $mg/m^2$/day. In one embodiment, the particular dosage is about 400 $mg/m^2$/day. In one embodiment, the particular dosage is about 450 $mg/m^2$/day. In one embodiment, the particular dosage is about 500 $mg/m^2$/day. In certain embodiments, the particular dosage is up to about 100 $mg/m^2$/day. In one embodiment, the particular dosage is up to about 120 $mg/m^2$/day. In one embodiment, the particular dosage is up to about 140 $mg/m^2$/day. In one embodiment, the particular dosage is up to about 150 $mg/m^2$/day. In one embodiment, the particular dosage is up to about 180 $mg/m^2$/day. In one embodiment, the particular dosage is up to about 200 $mg/m^2$/day. In one embodiment, the particular dosage is up to about 220 $mg/m^2$/day. In one embodiment, the particular dosage is up to about 240 $mg/m^2$/day. In one embodiment, the particular dosage is up to about 250 $mg/m^2$/day. In one embodiment, the particular dosage is up to about 260 $mg/m^2$/day. In one embodiment, the particular dosage is up to about 280 $mg/m^2$/day. In one embodiment, the particular dosage is up to about 300 $mg/m^2$/day. In one embodiment, the particular dosage is up to about 320 $mg/m^2$/day. In one embodiment, the particular dosage is up to about 350 $mg/m^2$/day. In one embodiment, the particular dosage is up to about 380 $mg/m^2$/day. In one embodiment, the particular dosage is up to about 400 $mg/m^2$/day. In one embodiment, the particular dosage is up to about 450 $mg/m^2$/day. In one embodiment, the particular dosage is up to about 500 $mg/m^2$/day. In one embodiment, the particular dosage is up to about 750 $mg/m^2$/day. In one embodiment, the particular dosage is up to about 1000 $mg/m^2$/day.

In one embodiment, the amount of azacitidine administered in the methods provided herein may range, e.g., between about 5 mg/day and about 2,000 mg/day. In one embodiment, the range is between about 10 mg/day and about 2,000 mg/day. In one embodiment, the range is between about 20 mg/day and about 2,000 mg/day. In one embodiment, the range is between about 50 mg/day and about 1,000 mg/day. In one embodiment, the range is between about 100 mg/day and about 1,000 mg/day. In one embodiment, the range is between about 100 mg/day and about 500 mg/day. In one embodiment, the range is between about 150 mg/day and about 500 mg/day. In one embodiment, the range is between about 150 mg/day and about 250 mg/day. In certain embodiments, the particular dosage is about 10 mg/day. In one embodiment, the particular dosage is about 20 mg/day. In one embodiment, the particular dosage is about 50 mg/day. In one embodiment, the particular dosage is about 75 mg/day. In one embodiment, the particular dosage is about 100 mg/day. In one embodiment, the particular dosage is about 120 mg/day. In one embodiment, the particular dosage is about 150 mg/day. In one embodiment, the particular dosage is about 200 mg/day. In one embodiment, the particular dosage is about 250 mg/day. In one embodiment, the particular dosage is about 300 mg/day. In one embodiment, the particular dosage is about 350 mg/day. In one embodiment, the particular dosage is about 400 mg/day. In one embodiment, the particular dosage is about 450 mg/day. In one embodiment, the particular dosage is about 500 mg/day. In one embodiment, the particular dosage is about 600 mg/day. In one embodiment, the particular dosage is about 700 mg/day. In one embodiment, the particular dosage is about 800 mg/day. In one embodiment, the particular dosage is about 900 mg/day. In one embodiment, the particular dosage is about 1,000 mg/day. In one embodiment, the particular dosage is about 1,200 mg/day. In one embodiment, the particular dosage is about 1,500 mg/day. In certain embodiments, the particular dosage is up to about 10 mg/day. In one embodiment, the particular dosage is up to about 20 mg/day. In one embodiment, the particular dosage is up to about 50 mg/day. In one embodiment, the particular dosage is up to about 75 mg/day. In one embodiment, the particular dosage is up to about 100 mg/day. In one embodiment, the particular dosage is up to about 120 mg/day. In one embodiment, the particular dosage is up to about 150 mg/day. In one embodiment, the particular dosage is up to about 200 mg/day. In one embodiment, the particular dosage is up to about 250 mg/day. In one embodiment, the particular dosage is up to about 300 mg/day. In one embodiment, the particular dosage is up to about 350 mg/day. In one embodiment, the particular dosage is up to about 400 mg/day. In one embodiment, the particular dosage is up to about 450 mg/day. In one embodiment, the particular dosage is up to about 500 mg/day. In one embodiment, the particular dosage is up to about 600 mg/day. In one embodiment, the particular dosage is up to about 700 mg/day. In one embodiment, the particular dosage is up to about 800 mg/day. In one embodiment, the particular dosage is up to about 900 mg/day. In one embodiment, the particular dosage is up to about 1,000 mg/day. In one embodiment, the particular dosage is up to about 1,200 mg/day. In one embodiment, the particular dosage is up to about 1,500 mg/day.

In one embodiment, the amount of azacitidine in the pharmaceutical composition or dosage form provided herein may range, e.g., between about 5 mg and about 2,000 mg. In one embodiment, the range is between about 10 mg and about 2,000 mg. In one embodiment, the range is between about 20 mg and about 2,000 mg. In one embodiment, the range is between about 50 mg and about 1,000 mg. In one embodiment, the range is between about 50 mg and about 500 mg. In one embodiment, the range is between about 50 mg and about 250 mg. In one embodiment, the range is between about 100 mg and about 500 mg. In one embodiment, the range is between about 150 mg and about 500 mg. In one embodiment, the range is between about 150 mg and about 250 mg. In certain embodiments, the particular amount is about 10 mg. In one embodiment, the particular amount is about 20 mg. In one embodiment, the particular amount is about 50 mg. In one embodiment, the particular amount is about 75 mg. In one embodiment, the particular amount is about 100 mg. In one embodiment, the particular amount is about 120 mg. In one embodiment, the particular amount is about 150 mg. In one embodiment, the particular amount is about 200 mg. In one embodiment, the particular amount is about 250 mg. In one embodiment, the particular amount is about 300 mg. In one embodiment, the particular amount is about 350 mg. In one embodiment, the particular amount is about 400 mg. In one embodiment, the particular amount is about 450 mg. In one embodiment, the particular amount is about 500 mg. In one embodiment, the particular amount is about 600 mg. In one embodiment, the particular amount is about 700 mg. In one embodiment, the particular amount is about 800 mg. In one embodiment, the particular amount is about 900 mg. In one embodiment, the particular amount is about 1,000 mg. In one embodiment, the particular amount is about 1,200 mg. In one embodiment, the particular amount is about 1,500 mg. In certain embodiments, the particular amount is up to about 10 mg. In one embodiment, the particular amount is up to about 20 mg. In one embodiment, the particular amount is up to about 50 mg. In one embodiment, the particular amount is up to about 75 mg. In one embodiment, the particular amount is up to about 100 mg. In one embodiment, the particular amount is up to about 120 mg. In one embodiment, the particular amount is up to about 150 mg. In one embodiment, the particular amount is up to about 200 mg. In one embodiment, the particular amount is up to about 250 mg. In one embodiment, the particular amount is up to about 300 mg. In one embodiment, the particular amount is up to about 350 mg. In one embodiment, the particular amount is up to about 400 mg. In one embodiment, the particular amount is up to about 450 mg. In one embodiment, the particular amount is up to about 500 mg. In one embodiment, the particular amount is up to about 600 mg. In one embodiment, the particular amount is up to about 700 mg. In one embodiment, the particular amount is up to about 800 mg. In one embodiment, the particular amount is up to about 900 mg. In one embodiment, the particular amount is up to about 1,000 mg. In one embodiment, the particular amount is up to about 1,200 mg. In one embodiment, the particular amount is up to about 1,500 mg.

In one embodiment, azacitidine can be delivered as a single dose such as, e.g., a single bolus injection, or oral tablets or pills; or over time such as, e.g., continuous infusion over time or divided bolus doses over time. In one embodiment, azacitidine can be administered repetitively if necessary, for example, until the patient experiences stable disease or regression, or until the patient experiences disease progression or unacceptable toxicity. Stable disease or lack thereof is determined by methods known in the art such as evaluation of patient's symptoms, physical examination, visualization of the tumor that has been imaged using X-ray, CAT, PET, or MRI scan and other commonly accepted evaluation modalities.

In one embodiment, azacitidine can be administered once daily or divided into multiple daily doses such as twice daily, three times daily, and four times daily. In one embodiment, the administration can be continuous (i.e., daily for consecutive days or every day), intermittent, e.g., in cycles (i.e., including days, weeks, or months of rest when no drug is administered). In one embodiment, azacitidine is administered daily, for example, once or more than once each day for a period of time. In one embodiment, azacitidine is administered daily for an uninterrupted period of at least 7 days. In some embodiments, azacitidine is administered up to 52 weeks. In one embodiment, azacitidine is administered intermittently, i.e., stopping and starting at either regular or irregular intervals. In one embodiment, azacitidine is administered for one to six days per week. In one embodiment, azacitidine is administered on alternate days. In one embodiment, azacitidine is administered in cycles (e.g., administered daily or continuously for a certain period interrupted with a rest period). In one embodiment, azacitidine is administered daily for two to eight consecutive weeks, then a rest period with no administration for up to one week; or e.g., daily administration for one week, then a rest period with no administration for up to three weeks).

In one embodiment, the frequency of administration ranges from about daily to about monthly In one embodiment, azacitidine is administered once a day. In another embodiment, azacitidine is administered twice a day. In yet another embodiment, azacitidine is administered three times a day. In still another embodiment, azacitidine is administered four times a day. In one embodiment, azacitidine is administered once every other day. In one embodiment, azacitidine is administered twice a week. In one embodiment, azacitidine is administered once every week. In one embodiment, azacitidine is administered once every two weeks. In one embodiment, azacitidine is administered once every three weeks. In one embodiment, azacitidine is administered once every four weeks.

In one embodiment, azacitidine is administered once per day from one day to six months. In one embodiment, azacitidine is administered from one week to three months. In one embodiment, azacitidine is administered from one week to four weeks. In one embodiment, azacitidine is administered from one week to three weeks. In one embodiment, azacitidine is administered from one week to two weeks. In one embodiment, azacitidine is administered once per day for about one week. In one embodiment, azacitidine is administered once per day for about two weeks. In one embodiment, azacitidine is administered once per day for about three weeks. In one embodiment, azacitidine is administered once per day for about four weeks. In one embodiment, azacitidine is administered once per day for about 6 weeks. In one embodiment, azacitidine is administered once per day for about 9 weeks. In one embodiment, azacitidine is administered once per day for about 12 weeks. In one embodiment, azacitidine is administered once per day for about 15 weeks. In one embodiment, azacitidine is administered once per day for about 18 weeks. In one embodiment, azacitidine is administered once per day for about 21 weeks. In one embodiment, azacitidine is administered once per day for about 26 weeks. In certain embodiments, azacitidine is administered intermittently. In certain embodiments, azacitidine is administered intermittently in the amount of between about 50 mg/m$^2$/day and about 2,000 mg/m$^2$/day. In certain embodiments, azacitidine is administered continuously. In certain embodiments, azacitidine is administered continuously in the amount of between about 50 mg/m$^2$/day and about 1,000 mg/m$^2$/day.

In certain embodiments, azacitidine is administered to a patient in cycles (e.g., daily administration for one week, then a rest period with no administration for up to three weeks). Cycling therapy involves the administration of an active agent for a period of time, followed by a rest for a period of time, and repeating this sequential administration. Cycling therapy can reduce the development of resistance, avoid or reduce the side effects, and/or improves the efficacy of the treatment.

In one embodiment, a method provided herein comprises administering azacitidine in 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, or greater than 40 cycles. In one embodiment, the median number of cycles administered in a group of patients is about 1. In one embodiment, the median number of cycles is about 2. In one embodiment, the median number of cycles is about 3. In one embodiment, the median number of cycles is about 4. In one embodiment, the median number of cycles is about 5. In one embodiment, the median number of cycles is about 6. In one embodiment, the median number of cycles is about 7. In one embodiment, the median number of cycles is about 8. In one embodiment, the median number of cycles is about 9. In one embodiment, the median number of cycles is about 10. In one embodiment, the median number of cycles is about 11. In one embodiment, the median number of cycles is about 12. In one embodiment, the median number of cycles is about 13. In one embodiment, the median number of cycles is about 14. In one embodiment, the median number of cycles is about 15. In one embodiment, the median number of cycles is about 16. In one embodiment, the median number of cycles is about 17. In one embodiment, the median number of cycles is about 18. In one embodiment, the median number of cycles is about 19. In one embodiment, the median number of cycles is about 20. In one embodiment, the median number of cycles is about 21. In one embodiment, the median number of cycles is about 22. In one embodiment, the median number of cycles is about 23. In one embodiment, the median number of cycles is about 24. In one embodiment, the median number of cycles is about 25. In one embodiment, the median number of cycles is about 26. In one embodiment, the median number of cycles is about 27. In one embodiment, the median number of cycles is about 28. In one embodiment, the median number of cycles is about 29. In one embodiment, the median number of cycles is about 30. In one embodiment, the median number of cycles is greater than about 30 cycles.

In one embodiment, azacitidine is administered to a patient at a dose provided herein over a cycle of 28 days which consists of a 7-day treatment period and a 21-day resting period. In one embodiment, azacitidine is administered to a patient at a dose provided herein each day from day 1 to day 7, followed with a resting period from day 8 to day 28 with no administration of azacitidine. In one embodiment, azacitidine is administered to a patient in cycles, each cycle consisting of a 7-day treatment period followed with a 21-day resting period. In particular embodiments, azacitidine is administered to a patient at a dose of about 50, about 60, about 70, about 75, about 80, about 90, or about 100 mg/m$^2$/day, for 7 days, followed with a resting period of 21 days. In one embodiment, azacitidine is administered intravenously. In one embodiment, azacitidine is administered subcutaneously.

In other embodiments, azacitidine is administered orally in cycles. In one embodiment, azacitidine is administered daily in single or divided doses for about one week. In one embodiment, azacitidine is administered daily for about two weeks. In one embodiment, azacitidine is administered daily for about three weeks. In one embodiment, azacitidine is administered daily for about four weeks. In one embodiment, azacitidine is administered daily for about five weeks. In one embodiment, azacitidine is administered daily for about six weeks. In one embodiment, azacitidine is administered daily for about eight weeks. In one embodiment, azacitidine is administered daily for about ten weeks. In one embodiment, azacitidine is administered daily for about fifteen weeks. In one embodiment, azacitidine is administered daily for or about twenty weeks. The administration is followed by a rest period of about 1 day to about ten weeks. In one embodiment, the methods provided herein contemplate cycling treatments of about one week. In one embodiment, the methods provided herein contemplate cycling treatments of about two weeks. In one embodiment, the methods provided herein contemplate cycling treatments of about three weeks. In one embodiment, the methods provided herein contemplate cycling treatments of about four weeks. In one embodiment, the methods provided herein contemplate cycling treatments of about five weeks. In one embodiment, the methods provided herein contemplate cycling treatments of about six weeks. In one embodiment, the methods provided herein contemplate cycling treatments of about eight weeks. In one embodiment, the methods provided herein contemplate cycling treatments of about ten weeks. In one embodiment, the methods provided herein contemplate cycling treatments of about fifteen weeks. In one embodiment, the methods provided herein contemplate cycling treatments of about twenty weeks. In some embodiments, azacitidine is administered daily in single or divided doses for about one week. In one embodiment, azacitidine is administered daily for about two weeks. In one embodiment, azacitidine is administered daily for about three weeks. In one embodiment, azacitidine is administered daily for about four weeks. In one embodiment, azacitidine is administered daily for about five weeks. In one embodiment, azacitidine is administered daily for about six weeks. In one embodiment, the resting period of about 1, 3, 5, 7, 9, 12, 14, 16, 18, 20, 22, 24, 26, 28, 29, or 30 days. In some embodiments, the rest period is 1 day. In some embodiments, the rest period is 3 days. In some embodiments, the rest period is 7 days. In some embodiments, the rest period is 14 days. In some embodiments, the rest period is 28 days. The frequency, number and length of dosing cycles can be increased or decreased.

In one embodiment, COMPOUND 2 is administered orally once a day. In one embodiment, COMPOUND 2 is administered on days 1-28 of each 28-day cycle. In one embodiment, 50 mg of COMPOUND 2 is administered orally once a day. In another embodiment, 100 mg of COMPOUND 2 is administered orally once a day. IN yet another embodiment, 200 mg of COMPOUND 2 is administered orally once a day. In one embodiment, azacitidine is administered subcutaneously for 7 days. In one embodiment, azacitidine is administered on days 1-7 of each 28-day cycle. In one embodiment, 75 mg/m2/day of azacitidine is administered on days 1-7 of each 28-day cycle.

EXAMPLES

Example 1

Effect of Combination of COMPOUND 2 and Azacitidine on EPO-differentiation in AML cells EPO differentiation assay in TF1-IDH1$^{R132H}$ cells. Measures of cell differentiation, growth and death were evaluated in TF1-IDH1$^{R132H}$ cells, using an in vitro EPO differentiation assay and dose-schedule paradigms represented in FIG. 1. Cells were treated with vehicle, AZA alone, COMPOUND 2 alone, or the combination of AZA+COMPOUND 2. In the sequential schedule, cells were pre-treated with AZA for three days before addition of COMPOUND 2. In the concurrent schedule, cells were co-treated with AZA and COMPOUND 2 throughout the assay. Endpoints assessed assays were: cell pellet color evaluation (hemoglobinization assay); HBG and KLF1 RNA by RT-qPCR; CD235a-positive cell populations by flow cytometry (differentiation markers); and Growth and apoptosis by IncuCyte Zoom real-time imaging.

Compounds: COMPOUND 2 was used as a 10 mM stock solution in DMSO. The stock was aliquoted as 20 µl batches and stored at −20° C. The running stock was thawed and kept at room temperature in the dark for use in ongoing experiments.

Azacitidine (AZA) was stored in a desiccator at 4° C. The required quantity was weighed in a Mettler covered weighing balance and reconstituted in RNase and DNase free water to give a 10 mM running stock. The solution was aliquoted as 30 µl batches and stored at −20° C. A fresh 10 mM AZA vial was thawed each time for an experiment and discarded after use.

A 100× master stock for each compound was made fresh each time it was required from frozen stocks i.e. 100 µM stock was prepared by adding 10 µl of 10 mM stock in 990 µl of media. From this 100× stock, the required volume was added to cells for a given desired final concentration.

Cell lines: Engineered TF-1 erythroleukemia cells overexperessing the IDH1$^{R132H}$ allele were grown in RPMI containing HEPES and L-glutamine (Lonza 12-115F), 10% FBS (HyClone SH30088.03), Pen/Strep (Life Technologies 15070-063), G418: final concentration 500 µg/ml (Life Technologies 10131-027), GM-CSF: final concentration 5 ng/ml (R&D 215-GM-050). G418 and GM-CSF were added fresh to media each time cells were passaged. The media was changed every 2-3 days (by pelleting cells and resuspending in fresh media, or by adding 2 ml of cells to 10 ml of fresh media. When treating cells with compound, the media was always changed by pelleting cells to ensure proper compound concentration).

Assays. EPO differentiation assay: TF1/pLVX and TF1 IDH1$^{R132H}$ cells (100,000 cells/ml) were pretreated for 7 days with COMPOUND 2, AZA or a combination (medium changed every 2 days) and washed three times with PBS to remove residual GM-CSF. Cells were then induced to differentiate using EPO (2 unit/ml) in the presence or absence of COMPOUND 2. Induction continued for 7 days and the cell pellets were collected and imaged for hemoglobinization content (as a surrogate for differentiation into blood lineage).

HBG and KLF1 qPCR: The RNA was isolated from cells by RNAeasy kit (Qiagen) and 500 ng RNA was used to make cDNA (Superscript VILO kit, Life technologies) and followed by real-time qPCR to detect fetal hemoglobin (HBG) and KLF-1 gene expression using Taqman probes obtained from Applied Biosciences.

Results. Enhanced EPO-induced differentiation with AZA+COMPOUND 2 combinations.

Measures of cell differentiation, growth and death were evaluated in TF1-IDH1$^{R132H}$ cells, using an in vitro EPO differentiation assay and dose-schedule paradigms represented in FIG. 1. Cells were treated with vehicle, AZA alone, COMPOUND 2 alone, or the combination of AZA+COMPOUND 2. In the sequential schedule, cells were pre-treated with AZA for three days before addition of COMPOUND 2. In the concurrent schedule, cells were co-treated with AZA and COMPOUND 2 throughout the assay.

Figure 2:
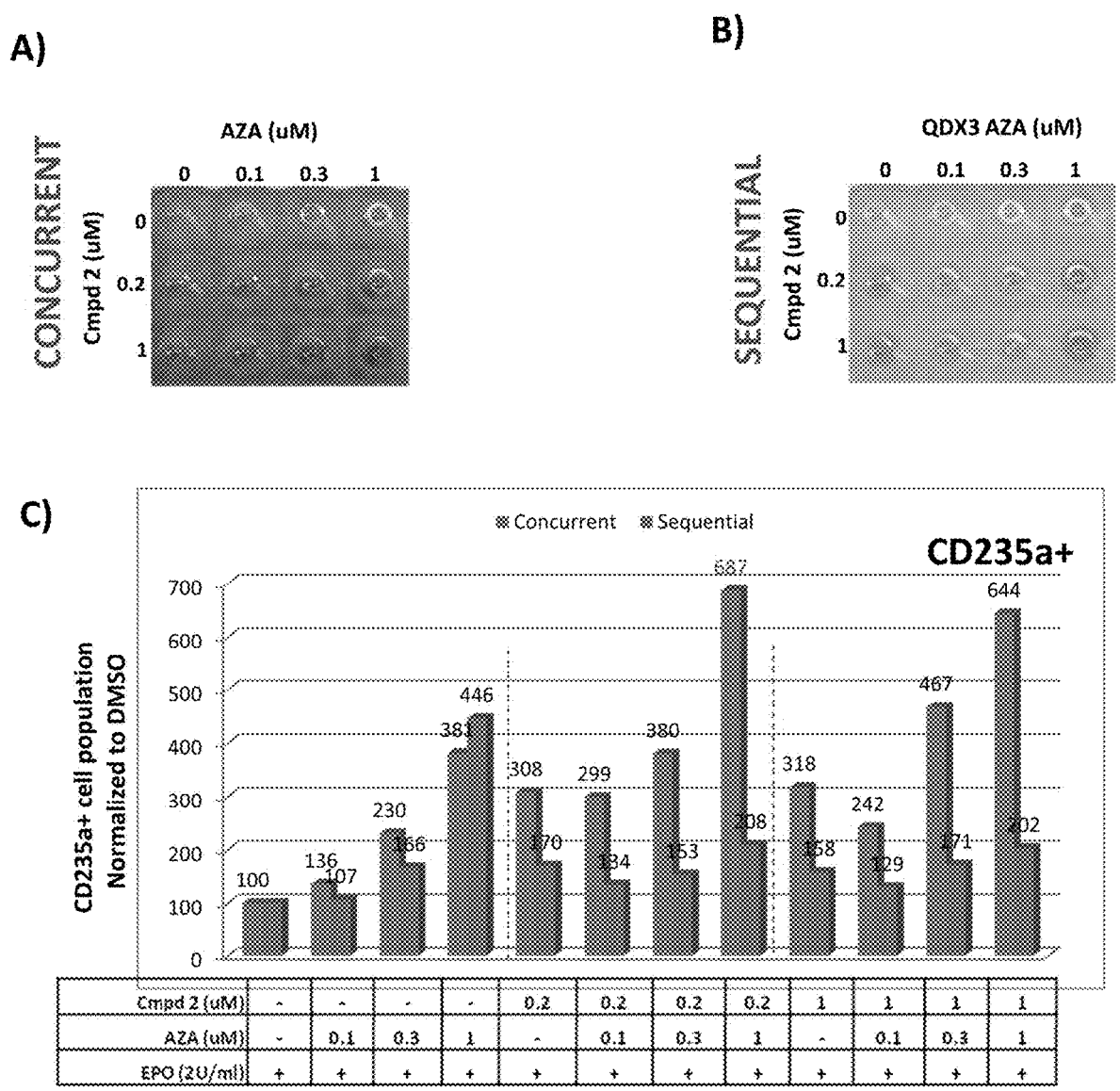
FIG. 2A depicts the effect of azacitidine, COMPOUND 2 and a concurrent combination of azacitidine and COMPOUND 2 on cell pellet color, with red color indicating hemoglobinization. Azacitidine had little or no effect on cell pellet color; however, with the azacitidine+COMPOUND 2 combination, coloration/hemoglobinization was noticeably greater than with COMPOUND 2 alone.
FIG. 2B depicts similar differentiation effect with a sequential schedule of azacitidine and COMPOUND 2.
FIG. 2C depicts effect of concurrent and sequential schedules on differentiation marker CD235a (Glycophorin A). Enhanced CD235a expression was observed in cells treated with the concurrent combination of azacitidine+COMPOUND 2, as compared to single agents.
Figure 3:
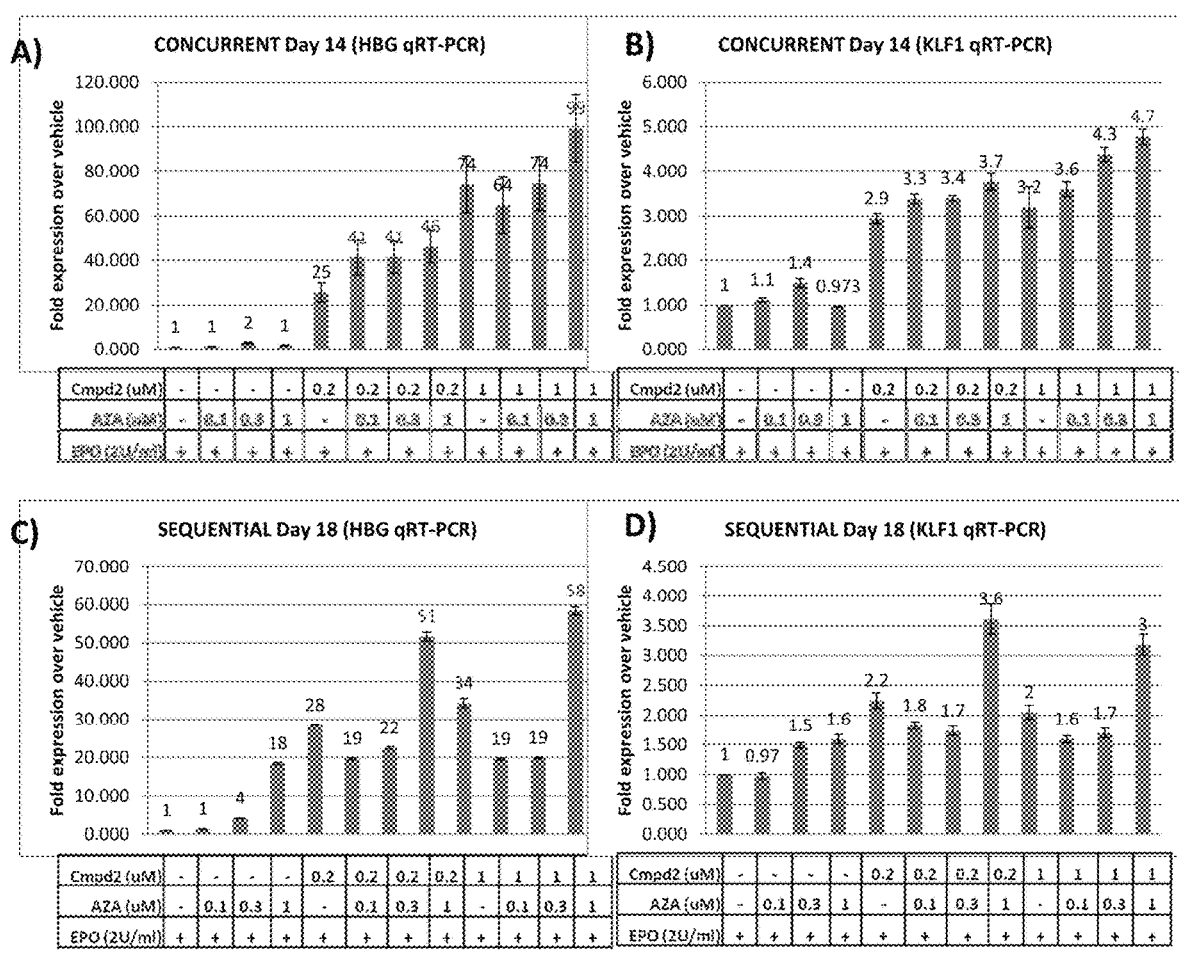
FIG. 3A depicts the effect on RNA expression of differentiation marker HBG with single agents azacitidine and COMPOUND 2, and concurrent combination of azacitidine+COMPOUND 2.
FIG. 3B depicts the effect on RNA expression of differentiation marker KLF1 with single agents azacitidine and COMPOUND 2, and concurrent combination of azacitidine+COMPOUND 2.
FIG. 3C depicts the effect on RNA expression of differentiation marker HBG with single agents AZA and COMPOUND 2, and sequential combination of azacitidine+COMPOUND 2.
FIG. 3D depicts the effect on RNA expression of differentiation marker KLF1 with single agents azacitidine and COMPOUND 2, and concurrent combination of azacitidine+COMPOUND 2.

Similar trends were observed with both concurrent and sequential schedules on differentiation endpoints of hemoglobinization (FIG. 2A, 2B), CD235 marker expression (FIG. 2C), and KLF1 (Kruppel-like factor 1) and HBG (hemoglobin gene A/B) RNA levels (FIG. 3). With the concurrent schedule, single agent COMPOUND 2 increased hemoglobin production in a dose-dependent manner, as evidenced by increased red color of cell pellets with 0.2 and 1.0 µM COMPOUND 2, as well as increased erythroid differentiation marker CD235a (Glycophorin A) (FIG. 2C). Single agent AZA had little or no effect on cell pellet color; however, with AZA+COMPOUND 2 combination, coloration/hemoglobinization was noticeably greater than with COMPOUND 2 alone (FIG. 2A). This was accompanied by enhanced CD235a expression on cells treated with the combination as compared to single agents (FIG. 2C). Enhanced effects with the combination were most apparent at the highest AZA concentration of 1 uM. Enhanced differentiation was also observed with the sequential schedule on the hemoglobinization endpoint (FIG. 2B), but not CD235a expression (FIG. 2C).

With the concurrent schedule, dose-dependent increases in RNA expression of differentiation marker HBG were observed with single agent COMPOUND 2, and concurrent combination of AZA+COMPOUND 2 (0.2 µM) resulted in potentiation (FIG. 3A). For example, COMPOUND 2 (0.2 µM) and AZA (1.0 µM) single agents showed 25-fold and 1-fold increases in HBG gene expression, respectively (FIG. 3A); while the combination of AZA (1.0 µM)+COMPOUND 2 (0.2 µM) resulted in a 46-fold increase (FIG. 3A). Dose-dependent increases in RNA expression of differentiation marker KLF1 were also observed with single agent COMPOUND 2; although enhanced activity with AZA was less apparent than for HBG expression (FIG. 3B). Enhanced differentiation on HBG RNA Expression was also observed with the sequential schedule at the 1 µM AZA concentration (FIG. 2C).

Figure 4:
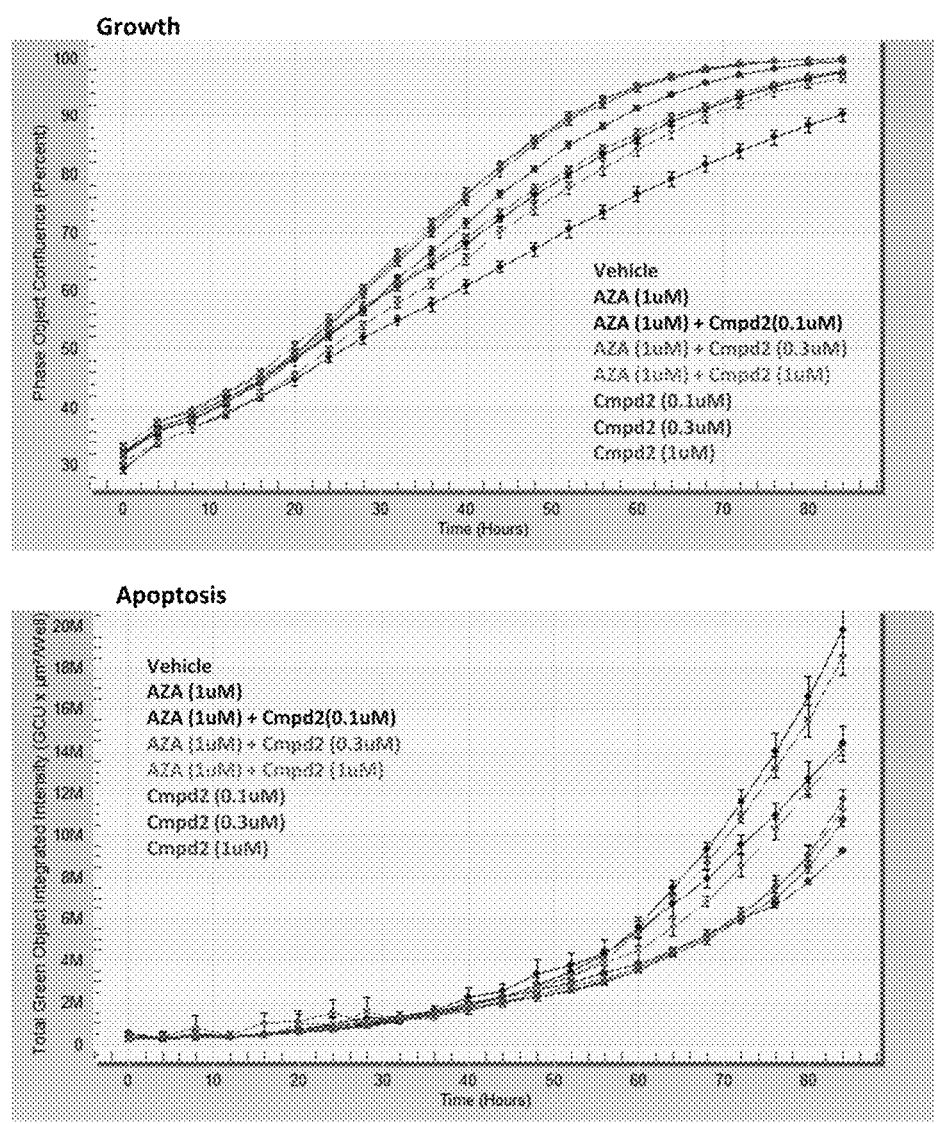
FIG. 4 depicts the effect of the combination of azacitidine and COMPOUND 2 on real time growth and apoptosis of TF-1 R132H cells.

Enhanced cell death with AZA+COMPOUND 2 concurrent combination. In order to track cell growth and death in real-time, a real-time analysis was performed using IncuCyte Zoom (FIG. 4). TF-1-IDH1$^{R132H}$ cells were treated with DMSO, single agent AZA (1 µM), single agent COMPOUND 2 (0.1, 0.3 or 1.0 µM), or the combination of AZA+COMPOUND 2 at each concentration.

Growth: AZA slowed growth of TF-1-IDH1$^{R132H}$ cells, while COMPOUND 2 as a single agent slightly promoted cell growth compared to the DMSO control. Cells treated with combinations of AZA+COMPOUND 2 grew comparably to the DMSO control (slower than COMPOUND 2 single agent, faster than AZA single agent).

Apoptosis: Single agent COMPOUND 2 had no effect on induction of apoptosis. At late time points (>60 hrs), single agent AZA increased apoptosis above the DMSO control. Cells treated with combinations of AZA+COMPOUND 2 (0.1 and 0.3 µM COMPOUND 2) had greater induction of apoptosis than single agent AZA, showing potentiation.

DISCUSSION. AML is a complex disease with a differentiation block phenotype. The differentiation block can be caused by mutations in genes that control cellular memory/epigenetic state (e.g. DNMT3A, TET2, IDH1/2 and ASXL1) (Ley et al., (2010). DNMT3A mutations in acute myeloid leukemia. N Engl J Med 363, 2424-2433; Patel et al., (2012). Prognostic relevance of integrated genetic profiling in acute myeloid leukemia. N Engl J Med 366, 1079-1089). To restore differentiation to leukemic hematopoietic stem cells, the differentiation program needs to be re-wired to overcome the epigenetic effects of these founder mutations.

In this study we have demonstrated the benefits of combining AZA+COMPOUND 2 in a model system of IDH-1 mutant AML, namely, a TF1-IDH1$^{R132H}$ cell line. The findings are summarized below:

Concurrent AZA+COMPOUND 2 combination enhanced differentiation and death, as shown by increased hemoglobinization beyond that of single agents, potentiation of COMPOUND 2 effect on HBG mRNA expression, and potentiation of AZA effect on apoptosis.

Sequential AZA+COMPOUND 2 treatment enhanced differentiation, as shown by the increase in hemoglobinization beyond that of single agents, and greater than additive increase in mRNA expression of HBG gene.

Together these results indicate a novel combination paradigm for combining AZA and COMPOUND 2 to benefit IDH1-mutant AML patients, and more particularly IDH1$^{R132H}$-mutant AML patients. Based on this mechanism, the combination can be translated to other IDH1-mutant cancers, and in particular, IDH1$^{R132H}$-mutant cancers.

Example 2

Phase 1b/2 Open-Label, Randomized Study of 2 Combinations of Isocitrate Dehydrogenase (IDH) Mutant Targeted Therapies Plus Azacitidine: Oral COMPOUND 2 Plus Subcutaneous Azacitidine and Oral COMPOUND 1 Plus SC Azacitidine in Subjects with Newly Diagnosed Acute Myeloid Leukemia Harboring an IDH1 or an IDH2 Mutation, Respectively, Who are not Candidates to Receive Intensive Induction Chemotherapy Indication: Treatment of patients 18 years and older with newly diagnosed acute myeloid leukemia (AML) harboring an IDH1 or an IDH2 mutation who are not candidates to receive intensive induction chemotherapy (IC).

Key Objectives—Phase 1b (Dose-Escalation Stage)
Primary Objectives
To assess the safety and tolerability of the combination treatments of oral COMPOUND 2 plus subcutaneous (SC) azacitidine and oral 2-methyl-1-[(4-[6-(trifluoromethyl)pyridin-2-yl]-6-{[2-(trifluoromethyl)pyridin-4-yl]amino}-1,3,5-triazin-2-yl)amino]propan-2-ol (hereinafter COMPOUND 1) plus SC azacitidine in subjects with newly diagnosed AML harboring an IDH1 or an IDH2 mutation, respectively, who are not candidates to receive intensive IC.

To establish the recommended Phase 2 dose (RP2D) of oral COMPOUND 2 and oral COMPOUND 1 when administered with SC azacitidine.

Secondary Objective
To assess the preliminary efficacy of the combination treatments of oral COMPOUND 2 plus SC azacitidine and oral COMPOUND 1 plus SC azacitidine in subjects with newly diagnosed AML harboring an IDH1 or an IDH2 mutation, respectively, who are not candidates to receive intensive IC.

Phase 2 (Randomized Stage)
Primary Objective
To assess the efficacy of the combination treatments of oral COMPOUND 2 plus SC azacitidine and oral COMPOUND 1+SC azacitidine versus SC azacitidine in subjects with newly diagnosed AML harboring an IDH1 or an IDH2 mutation, respectively, who are not candidates to receive intensive IC.

Secondary Objectives
To evaluate the safety of oral COMPOUND 2 and oral COMPOUND 1 when administered with SC azacitidine.

To characterize the pharmacokinetics (PK) of oral COMPOUND 2, COMPOUND 1, and SC azacitidine when administered in combination.

To evaluate the PK and PD relationships of oral COMPOUND 2 and oral COMPOUND 1 when administered with SC azacitidine with the suppression of 2-hydroxyglutarate (2-HG) levels in bone marrow and plasma samples. To evaluate the effect of oral COMPOUND 2 and oral COMPOUND 1 when administered with SC azacitidine versus SC azacitidine alone on health-related quality-of-life (HRQoL) outcomes.

Study Design
This Phase 1b/2 study is an open-label, randomized, multicenter trial to evaluate the safety and efficacy of oral COMPOUND 2+SC azacitidine and oral COMPOUND 1+SC azacitidine in subjects with newly diagnosed AML harboring an IDH1 or an IDH2 mutation, respectively. The study population consists of subjects who are not candidates to receive intensive IC. The study comprises a Phase 1b dose-escalation stage and a Phase 2 randomized stage.

Phase 1b Dose-Finding Stage

The Phase 1b stage is an open-label dose-finding study to evaluate the safety and tolerability of the combinations of oral COMPOUND 2 and oral COMPOUND 1 with SC azacitidine to define the RP2Ds of these 2 agents when administered in combination with SC azacitidine. The preliminary clinical activities of the oral COMPOUND 2+SC azacitidine and the oral COMPOUND 1+SC azacitidine regimens will also be assessed.

The Phase 1b stage consists of 3 periods: 1) screening; 2) treatment; and 3) follow-up.

Subject screening procedures will occur during the screening period within 28 days prior to the start of study treatment. The diagnosis of AML with an IDH mutation will be based on local review of both hematopathology and IDH gene mutation testing of bone marrow aspirate and/or peripheral blood samples. Subjects eligible for enrollment must not be candidates to receive intensive IC, based on the investigator's judgment, due to the presence of co-morbidities, declining performance status, or other factors. Subjects with newly diagnosed AML harboring an IDH1 mutation will be assigned to the oral COMPOUND 2+SC azacitidine arm, and subjects with newly diagnosed AML harboring an IDH2 mutation will be assigned to the oral COMPOUND 1+SC azacitidine arm. In the rare case in which a subject is diagnosed with an AML associated with dual IDH1 and IDH2 mutations, assignment to the oral COMPOUND 2 or COMPOUND 1 treatment arm will be based on a joint investigator and medical monitor decision and documented in the source.

During the treatment period a standard 3+3 design will be used. A Dose Review Team (DRT), consisting of a medical monitor, lead safety physician, biostatistician, other functional area representatives or designees, as appropriate, and all active site investigators and/or designees (at sites with a subject who has received study drug), will review all adverse events (AEs) experienced by subjects during Cycle 1 of each dose level to determine whether the maximum tolerated dose (MTD) of oral COMPOUND 2 or COMPOUND 1 when administered in combination with SC azacitidine has been exceeded. One dose level of oral COMPOUND 2 (500 mg daily) and 2 dose levels of oral COMPOUND 1 (100 mg daily and 200 mg daily) are planned to be evaluated. Dose levels lower than 500 mg daily for oral COMPOUND 2 and lower than 100 mg daily for oral COMPOUND 1 will be evaluated if these doses in combination with SC azacitidine are found to exceed the MTD during Cycle 1. Dose interruptions/delays and dose reductions may be used to manage toxicities. Subjects may receive study treatment until disease progression/relapse, study treatment becomes intolerable, or the subject wishes to discontinue study treatment for any reason. Response to treatment will be assessed by the investigators according to the modified International Working Group (IWG) AML Response Criteria (Cheson, et al. J Clin Oncol 2003; 21(24):4642-9). Hematologic improvement (HI) will be assessed according to the IWG myelodysplastic syndromes HI criteria (Cheson et al, Blood 2006; 108(2):419-25). Subjects are to undergo end-of-treatment evaluations when study treatment is discontinued. The reason for treatment discontinuation will be recorded in the electronic case report form (eCRF) pages and in the source document.

All subjects discontinued from study treatment for any reason other than withdrawal of consent for follow-up will continue to be assessed for AEs, concomitant medications, concomitant procedures, transfusions, healthcare resource utilization, response, hematologic improvement, subsequent AML therapies, and survival.

All subjects discontinued from study treatment for any reason except withdrawal of consent for follow-up or disease progression will continue to be assessed during the Follow-up period of the study for response until disease progression.

All subjects discontinued from study treatment for any reason except withdrawal of consent for follow-up will continue to be assessed for subsequent AML therapies, and survival.

The study will be conducted in compliance with the International Conference on Harmonization (ICH) Good Clinical Practices (GCPs) guidelines.

Phase 2 Randomized Stage

The Phase 2 stage is an open-label randomized study to evaluate the efficacy of the combinations of oral COMPOUND 2 and oral COMPOUND 1 with SC azacitidine versus SC azacitidine alone in order to assess the overall response rate (ORR), event-free survival (EFS), and morphologic complete remission (CR).

The Phase 2 stage will also consist of 3 periods: 1) screening; 2) treatment; and 3) follow-up.

As with Phase 1b, subject screening procedures will occur during the screening period within 28 days prior to the start of study treatment, but the diagnosis of AML will be performed locally for enrollment and confirmed based on a subsequent central review. The IDH mutation will be assessed centrally using samples of both bone marrow aspirate and/or peripheral blood. Subjects eligible for enrollment are those who are not candidates to receive intensive IC, based on the investigator's judgment, due to the presence of co-morbidities, declining performance status, or other factors.

Following review of eligibility, subjects with newly diagnosed AML harboring an IDH1 or IDH2 mutation will be randomized in a 2:1 ratio to 1 of 3 arms. Subjects with IDH1 mutation will be randomized to receive oral COMPOUND 2+SC azacitidine (Arm 1) versus SC azacitidine (Arm 3) in a 2:1 ratio; and subject with IDH2 mutation will be randomized to receive oral COMPOUND 1+SC azacitidine (Arm 2) versus SC azacitidine (Arm 3) in a 2:1 ratio. Arms 1 and 2 will randomize a minimum of 50 subjects, and Arm 3 will randomize a minimum of 25 IDH1 and 25 IDH2 (50 subjects total in Arm 3) (150 subjects total in all arms). In the rare case in which a subject is diagnosed with an AML associated with dual IDH1 and IDH2 mutations, randomization to the oral COMPOUND 2 or COMPOUND 1 treatment arm will be based on an investigator and medical monitor decision.

Subjects will be stratified by cytogenetics (better or intermediate versus poor cytogenetic risk.

Study treatment will start the same day as randomization. Assessments during study treatment include efficacy, safety, HRQoL, healthcare resource utilization, pharmacokinetics, pharmacodynamics, and correlative studies.

A retrospective central review of all bone marrow aspirates and/or biopsies, peripheral blood smears, and cytogenetics collected during the study will be conducted by personnel blinded to subject treatment. The central assessments will be used in the statistical analyses. Disagreement between central and local assessments will be adjudicated by a third party reviewer and the adjudicated assessment will be used in the statistical analyses.

Response to treatment and HI will be assessed by the investigators and retrospectively by a blinded Independent Response Assessment Committee (IRAC) according to modified IWG AML Response Criteria (Cheson, J Clin Oncol 2003; 21(24):4642-9) and IWG myelodysplastic syndromes HI criteria (Cheson, et al, Blood 2006; 108(2):419-25), respectively.

Dosing interruptions, dosing delays or dose modifications may occur for managing toxicities and/or augmenting treatment response during study treatment and.

The discontinuation of COMPOUND 2, COMPOUND 1, or azacitidine for subjects in the combination arms of the study is allowed. Subjects may continue treatment with single agent COMPOUND 2, COMPOUND 1, or azacitidine if in the investigator's assessment the subject continues to show clinical benefit and all protocol-specified criteria for continuing study treatment are met. Study treatment will be discontinued if the subject has progressive disease or receives alternative therapies.

The decision to discontinue a subject, which will not be delayed or refused by the sponsor, remains the responsibility of the treating physician. However, prior to discontinuing a subject, it is recommended that the investigator contact the medical monitor and forward appropriate supporting documents for review and discussion.

All subjects who have received at least one dose of study treatment should undergo End of Treatment (EOT) evaluations when study treatment is discontinued. The reason for discontinuation will be recorded in the electronic case report form (eCRF) pages and in the source document.

All subjects discontinued from study treatment for any reason other than withdrawal of consent for follow-up will continue to be assessed for AEs, concomitant medications, concomitant procedures, transfusions, healthcare resource utilization, response, hematologic improvement, subsequent AML therapies, and survival.

All subjects discontinued from study treatment for any reason except withdrawal of consent for follow-up or disease progression will continue to be assessed during the Follow-up period of the study for response until disease progression.

All subjects discontinued from study treatment for any reason except withdrawal of consent for follow-up will continue to be assessed for subsequent AML therapies, and survival.

The study will be conducted in compliance with International Conference on Harmonization (ICH) Good Clinical Practices (GCPs).

Length of Study

The full length of the study is expected to be approximately 60 months including recruitment, screening, treatment, and follow up for Phase 1b and Phase 2. Recruitment is expected to take 7 months for Phase 1b, and 17 months for Phase 2. For a single subject, the expected duration of the Phase 1b segment of the study is approximately 13 months, including a screening period for up to 28 days, and the expected duration of the Phase 2 segment of the study is approximately 25 months, including a screening period for up to 28 days.

The End of Trial is defined as either the date of the last visit of the last subject to complete the post-treatment follow-up, or the date of receipt of the last data point from the last subject that is required for primary, secondary, and/or exploratory analysis, as pre-specified in the protocol, whichever is the later date.

The trial will continue until the required amount of EFS events for full statistical power occur.

Study Treatments

COMPOUND 2 and COMPOUND 1 are administered orally once a day (QD) on Days 1-28 of each 28-day cycle. Subjects should be instructed to take their daily dose at approximately the same time each day ±4 hours. Each dose should be taken with a glass of water and consumed over as short a time as possible. Subjects should be instructed to swallow tablets whole and to not chew the tablets. Fasting is required for 2 hours prior to and 1 hour following COMPOUND 2 or COMPOUND 1 administration. Water is allowed during fasting.

Azacitidine will be administered SC for 7 days of each 28-day treatment cycle starting on Day 1 during both Phase 1b and Phase 2. During the Phase 2 stage, subjects randomized to the azacitidine alone arms will receive azacitidine 75 mg/m$^2$/day SC for 7 days of each 28-day cycle. All randomized subjects will receive azacitidine 75 mg/m$^2$/day SC for 7 days every 28 days until the end of the study, unless they are discontinued from the treatment. In addition, subjects may receive best supportive care as needed, including antibiotics and transfusions, per investigator discretion. In the event that 2 or fewer doses are missed during the 7-day dosing period, dosing should continue so the subject receives the full 7 days of therapy. If 3 or more days are missed during the 7-day dosing period, the investigator should contact the sponsor and a decision on dosing will be made on a case-by-case basis.

Phase 1b:

Phase 1b will use a 3+3 design. For COMPOUND 2 one dose level will be explored enrolling 3 subjects. Cohort 1 will be initiated with oral COMPOUND 2 500 mg once a day and azacitidine 75 mg/m$^2$/day SC for 7 days of each 28-day cycle starting on Day 1 of each cycle. A Cohort −1 will be explored at 250 mg once a day and azacitidine 75 mg/m$^2$/day SC for 7 days of each 28-day cycle if 2 or more subjects in Cohort 1 have a dose-limiting toxicity (DLT) in Cohort 1.

For COMPOUND 1 two dose levels will be explored. Cohort 1 will be initiated with oral COMPOUND 1 100 mg once a day and azacitidine 75 mg/m$^2$/day SC for 7 days of each 28-day cycle starting on Day 1 of each cycle. If no DLTs are observed, the RP2D will be confirmed by the DRT and the 100 mg dose will be used as the starting dose for the Phase 2 segment of the study. Dose escalation to Cohort 2 will also be initiated with oral COMPOUND 1 200 mg once a day and azacitidine 75 mg/m$^2$/day SC for 7 days of each 28-day cycle starting on Day 1 of each cycle to explore the tolerability of the combination at this dose level. A Cohort −1 with oral COMPOUND 1 50 mg daily and azacitidine 75 mg/m$^2$/day SC for 7 days of each 28-day cycle starting on Day 1 of each cycle will be explored if 2 or more subjects have a DLT in Cohort 1.

The DRT will evaluate all toxicities of each subject after 1 cycle and determine whether further dose modifications are needed for individual subjects.

Phase 2:

COMPOUND 2 Combination Arm:

Subjects with an IDH1 mutation will receive COMPOUND 2 at the RP2D orally QD on Days 1-28 of each 28-day cycle+azacitidine 75 mg/m$^2$/day SC for 7 days of each 28-day cycle.

COMPOUND 1 Combination Arm:

Subjects with an IDH2 mutation will receive COMPOUND 1 at the RP2D orally QD on Days 1-28 of each 28-day cycle+azacitidine 75 mg/m$^2$/day SC for 7 days of each 28-day cycle.

Azacitidine Alone Arm:

Subjects with either an IDH1 or IDH2 mutation will receive azacitidine 75 mg/m$^2$/day SC for 7 days of each 28-day cycle.

Overview of Key Efficacy Assessments

Efficacy

Serial blood and bone marrow sampling will be used to determine response to therapy starting at Cycle 2. Response will be assessed locally during Phase 1b. During Phase 2, response will be assessed locally and confirmed centrally according to the modified IWG criteria based on the reported hematology laboratory parameters, peripheral blood smear, bone marrow aspirates and/or biopsies, and cytogenetics.

Subjects who discontinue study treatment prior to relapse or progression will complete monthly site visits until confirmation of relapse or progression. For subjects who have discontinued study treatment due to relapse or progression, monthly follow up can be performed by site visits or phone calls. Subjects will be followed until they have died, are lost to follow up, withdraw consent for further data collection, or until study closure.

Overview of Other Key Assessments

Safety

Safety assessments include adverse events, physical examination, Eastern Cooperative Oncology Group (ECOG) performance status, vital signs, echocardiogram (ECHO) or multi-gated acquisition (MUGA) scan, electrocardiogram (ECG), cardiac markers, urinalysis, coagulation, hematology, serum chemistry, transfusions, pregnancy testing (for females of child bearing potential (FCBP) only), and concomitant medications or procedures.

Plasma PK/PD of COMPOUND 2 and COMPOUND 1

The PK profile of COMPOUND 2/COMPOUND 1 and azacitidine combinations will be evaluated by plasma concentrations and PK parameters of COMPOUND 2/COMPOUND 1 and azacitidine combinations in the Phase 2 segment. Plasma concentrations of 2-HG will be evaluated in relation to plasma concentrations of COMPOUND 2 or COMPOUND 1 over time.

Investigational Product Accountability

Oral COMPOUND 2 and COMPOUND 1 are dispensed on Day 1 of each treatment cycle and accounted for after completion of each treatment cycle.

Azacitidine will be administered SC by study site personnel. Accurate recording of all IP, including preparation and dosing, will be made in the appropriate section of the subject's CRF and source documents.

Statistical Methods

Phase 1b:

Statistical analyses in Phase 1b will be primarily descriptive in nature. Tabulations will be produced for disposition, demographic and baseline disease characteristics, safety, PK, PD, and clinical activity parameters. Categorical data will be summarized by frequency distributions (numbers and percentages of subjects) and continuous data will be summarized by descriptive statistics (mean, standard deviation, median, minimum, and maximum). Data will be summarized by dose level and overall when appropriate.

Phase 2:

The primary efficacy endpoint of Overall Response Rate (ORR) in Phase 2 includes responses of CR, CRp, morphologic leukemia-free state [MLFS], CRi, and PR, according to modified IWG AML response criteria. The treatment difference in ORR will be tested using the Fisher's exact test in the ITT population. This test will provide the pivotal p-value for the comparison of the ORRs of oral COMPOUND 2+SC azacitidine versus pooled azacitidine mono therapy group which includes subjects with IHD1 or IDH2 mutations and who are randomized to the azacitidine mono therapy, and ORRs of oral COMPOUND 1+SC azacitidine versus pooled azacitidine mono therapy group separately.

A maximum of 150 subjects will be randomized in this study with 50 IDH1 subjects in the oral COMPOUND 2+SC azacitidine arm, 50 IDH2 subjects in the oral COMPOUND 1+SC azacitidine arm, and a combined 50 IDH1 or IDH2 subjects in the azacitidine mono therapy arm (pooled azacitidine mono therapy). The comparisons will be conducted separately for oral COMPOUND 2+SC azacitidine versus pooled azacitidine mono therapy and COMPOUND 1+azacitidine versus pooled azacitidine mono therapy. Assuming an ORR of 30% in the pooled azacitidine mono therapy arm and an ORR of 50% for both oral COMPOUND 1+SC azacitidine arm and oral COMPOUND 2+SC azacitidine arm, this designed sample size (50 per treatment arm) for each comparison will provide 78% power to detect an 20% improvement in ORR and demonstrate a statistically significant difference in ORR at a Type I error rate of 0.2 (two-sided). The multiple comparison was not considered in the sample size calculation.

Inclusion Criteria

Subjects must satisfy the following criteria to be enrolled in the study:

Subject is ≥18 years of age at the time of signing the informed consent form (ICF).

Subject must understand and voluntarily sign an ICF prior to any study-related assessments/procedures being conducted.

Subject is willing and able to adhere to the study visit schedule and other protocol requirements.

Subject has previously untreated AML primary (ie, de novo) or secondary (progression of MDS or myeloproliferative neoplasms ([MPN], or therapy-related) AML according to the WHO classification with ≥20% leukemic blasts in the bone marrow: Have an IDH1 or IDH2 gene mutation (R132, R140, or R172); Validated local testing may be used to confirm eligibility for Phase 1, but central testing must be performed to confirm eligibility for Phase 2; By the investigator's assessment who are not candidates to receive intensive IC.

Subject has an Eastern Cooperative Oncology Group (ECOG) performance status of 0, 1 or 2.

Subject has adequate organ function defined as: Serum aspartate aminotransferase/serum glutamic oxaloacetic transaminase (AST/SGOT) and alanine aminotransferase (ALT/SGPT)≤3×ULN, unless considered due to leukemic organ involvement; Serum total bilirubin <1.5×ULN. Higher levels are acceptable if these can be attributed to ineffective erythropoiesis, Gilbert's syndrome (eg, a gene mutation in UGT1A1), or leukemic organ involvement; Serum creatinine <2×ULN or creatinine clearance >30 mL/min based on the Cockroft-Gault glomerular filtration rate (GFR) estimation: (140−Age)×(weight in kg)×(0.85 if female)/72×serum creatinine.

Agree to serial bone marrow aspirate/biopsies.

Females of childbearing potential (FCBP)* may participate, providing they meet the following conditions: Agree to abstain from sexual intercourse or to use at least two effective contraceptive methods (oral, injectable, patch, or implantable hormonal contraceptive; tubal ligation; intrauterine device; synthetic double-barrier contraceptive with spermicide; or vasectomized partner) at screening and throughout the study, and for 4 months following the last study treatment (6 months following the last dose of azacitidine in Canada); and have a negative serum β-subunit of human chorionic gonadotropin (β-hCG) pregnancy test (sensitivity of at least 25 mIU/mL) at screening; and have a negative serum or urine (investigator's discretion under local regulations) β-hCG pregnancy test (sensitivity of at least 25 mIU/mL) within 72 hours prior to the start of study treatment in the Treatment Period (note that the screening serum pregnancy test can be used as the test prior to the start of study treatment in the Treatment Period if it is performed within the 72-hour timeframe).

Male subjects with a female partner of childbearing potential must agree to abstain from sexual intercourse or to the use of at least 2 effective contraceptive methods (eg, synthetic condoms with spermicide, etc) at screening and throughout the course of the study and should avoid fathering a child during the course of the study and for 4 months following the last study treatment (6 months following the last dose of azacitidine in Canada).

Exclusion Criteria

The presence of any of the following will exclude a subject from enrollment:

Subject is suspected or proven to have acute promyelocytic leukemia based on morphology, immunophenotype, molecular assay, or karyotype Subject has AML secondary to chronic myelogenous leukemia (CML).

Subject has received a targeted agent against an IDH1 or IDH2 mutation.

Subject has received prior systemic anticancer therapy, HSCT, or radiotherapy for AML. Note that hydroxyurea is allowed prior to the start of study treatment for the control of leukocytosis in subjects with white blood cell (WBC) counts >30×10$^9$/L (however, hydroxyurea should not be given within 72 hours prior to and after administration of azacitidine). For subjects with secondary AML (eg, MDS or MPN) treatment for prior cancer is not exclusionary; full treatment information will be collected within the CRF.

Subject has received prior treatment with azacitidine or decitabine for MDS.

Subject has or is suspected of having central nervous system (CNS) leukemia. Evaluation of cerebrospinal fluid is only required if CNS involvement by leukemia is suspected during screening.

Subject has immediate life-threatening, severe complications of leukemia such as uncontrolled bleeding, pneumonia with hypoxia or shock, and/or disseminated intravascular coagulation.

Subject has significant active cardiac disease within 6 months prior to the start of study treatment, including New York Heart Association (NYHA) class III or IV congestive heart failure; acute coronary syndrome (ACS); and/or stroke; or left ventricular ejection fraction (LVEF)<40% by echocardiogram (ECHO) or multi-gated acquisition (MUGA) scan obtained within 28 days prior to the start of study treatment.

Subject has prior history of malignancy, other than MDS, MPN, or AML, unless the subject has been free of the disease for ≥1 year prior to the start of study treatment. However, subjects with the following history/concurrent conditions are allowed: basal or squamous cell carcinoma of the skin; carcinoma in situ of the cervix; carcinoma in situ of the breast; incidental histologic finding of prostate cancer (T1a or T1b using the tumor, node, metastasis clinical staging system).

Subject is known seropositive for or has active viral infection with human immunodeficiency virus (HIV), or active infection with hepatitis B virus (HBV) or hepatitis C virus (HCV)

Subject is known to have dysphagia, short-gut syndrome, gastroparesis, or other conditions that limit the ingestion or gastrointestinal absorption of drugs administered orally Subject has uncontrolled hypertension (systolic blood pressure [BP] >180 mmHg or diastolic BP >100 mmHg)

Subject is taking the following sensitive CYP substrate medications that have a narrow therapeutic range are excluded from the study unless the subject can be transferred to other medications at least 5 half-lives prior to the start of study treatment: phenytoin (CYP2C9), S-mephenytoin (CYP2C19), thioridazine (CYP2D6), theophylline, and tizanidine (CYP1A2).

Subject is taking the breast cancer resistance protein (BCRP) transporter-sensitive substrate rosuvastatin; subject should be excluded from the study unless he/she can be transferred to other medications at least 5 half-lives prior to the start of study treatment Subject has active uncontrolled systemic fungal, bacterial, or viral infection (defined as ongoing signs/symptoms related to the infection without improvement despite appropriate antibiotics, antiviral therapy, and/or other treatment).

Subject has known or suspected hypersensitivity to any of the components of study therapy.

Subject is taking medications that are known to prolong the QT interval unless he/she can be transferred to other medications within ≥5 half-lives prior to the start of study treatment. (If equivalent medication is not available, QTc will be closely monitored)

Subject has QTc interval (ie, Fridericia's correction [QTcF]) ≥450 ms or other factors that increase the risk of QT prolongation or arrhythmic events (eg, heart failure, hypokalemia, family history of long QT interval syndrome) at screening.

Female subject who is pregnant or lactating.

Subject has any significant medical condition, laboratory abnormality, or psychiatric illness that would prevent the subject from participating in the study.

Subject has any condition, including the presence of laboratory abnormalities, that places the subject at unacceptable risk if he/she were to participate in the study.

Subject has any condition that confounds the ability to interpret data from the study.

In certain embodiments, AML patients treated with COMPOUND 2 and azacitidine, for example undergoing the clinical protocol provided herein, will show a treatment response. In some embodiments, the treatment response is a Complete Response (CR), a Morphologic Leukemia-free State (MLFS), a Morphologic Complete Remission with Incomplete Neutrophil Recovery (CRi), Morphologic Complete Remission with Incomplete Platelet Recovery (CRp), or a Partial Remission (PR), according to modified IWG AML response criteria. In some embodiments, the treatment response is a hematologic improvement, for example, an improvement in Neutrophil Response (Hi-N), Platelet response (HI-P), and/or Erythroyd Response (HI-E), according to IWG MDS HI criteria. In certain embodiments, AML patients treated with COMPOUND 2 and azacitidine in the methods provide herein will show an improvement in event-free survival (EFS), duration of response, HRQoL and/or overall survival.

Having thus described several aspects of several embodiments, it is to be appreciated various alterations, modifications, and improvements will readily occur to those skilled in the art. Such alterations, modifications, and improvements are intended to be part of this disclosure, and are intended to be within the spirit and scope of the invention. Accordingly, the foregoing description and drawings are by way of example only.

The invention claimed is:

1. A method of treating acute myelogenous leukemia (AML) characterized by the presence of a mutant allele of IDH1, comprising administering to a subject in need thereof a mutant isocitrate dehydrogenase 1 (IDH1) inhibitor and azacitidine, wherein the mutant IDH1 inhibitor is (S)-N-((S)-1-(2-chlorophenyl)-2-((3,3-difluorocyclobutyl)amino)-2-oxoethyl)-1-(4-cyanopyridin-2-yl)-N-(5-fluoropyridin-3-yl)-5-oxopyrrolidine-2-carboxamide, having the following formula:

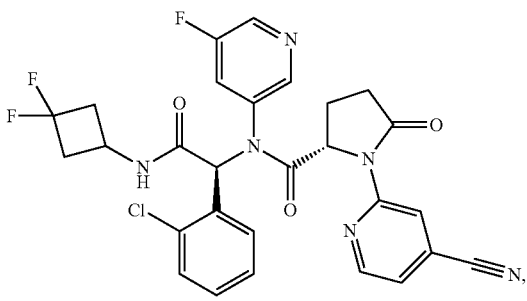 [SMILES: N#Cc1ccnc(N2C(=O)CC[C@H]2C(=O)N(c2cncc(F)c2)[C@H](C(=O)NC2CC(F)(F)C2)c2ccccc2Cl)c1]

or a pharmaceutically acceptable salt thereof (COMPOUND 2), and wherein the mutant allele of IDH1 has a mutation selected from R132H, R132C, R132L, R132V, R132S and R132GF.

2. The method of claim 1, wherein the dose of COMPOUND 2 is about 20 to 2000 mg/day.

3. The method of claim 1, wherein the dose of COMPOUND 2 is about 50 to 500 mg/day.

4. The method of claim 1, wherein the dose of COMPOUND 2 is about 50 mg/day.

5. The method of claim 1, wherein the dose of COMPOUND 2 is about 75 mg/day.

6. The method of claim 1, wherein the dose of COMPOUND 2 is about 100 mg/day.

7. The method of claim 1, wherein the dose of azacitidine is about 50 to about 500 mg/m$^2$/day.

8. The method of claim 1, wherein the dose of azacitidine is about 50 to about 200 mg/m$^2$/day.

9. The method of claim 1, wherein the dose of azacitidine is about 50 mg/m$^2$/day.

10. The method of claim 1, wherein the dose of azacitidine is about 60 mg/m$^2$/day.

11. The method of claim 1, wherein the dose of azacitidine is about 75 mg/m$^2$/day.

12. The method of claim 1, wherein COMPOUND 2 and azacitidine are administered concurrently.

13. The method of claim 1, wherein COMPOUND 2 and azacitidine are administered sequentially.

14. The method of claim 1, wherein the dose of COMPOUND 2 is about 500 mg/day.

15. The method of claim 1, wherein the azacitidine is administered in cycles.

16. The method of claim 15, wherein the azacitidine is administered subcutaneously for 7 days of each 28-day treatment cycle.

17. The method of claim 1, wherein the AML is previously untreated AML.

18. The method of claim 1, wherein the AML is newly diagnosed AML.

19. A pharmaceutical composition, comprising (S)-N-((S)-1-(2-chlorophenyl)-2((3,3-difluorocyclobutyl)amino)-2-oxoethyl)-1-(4-cyanopyridin-2-yl)-N-(5-fluoropyridin-3-yl)-5-oxopyrrolidine-2-carboxamide or a pharmaceutically acceptable salt thereof, and azacitidine.

20. A method of treating AML characterized by the presence of a mutant allele of IDH1 comprising administering to a patient in need thereof the pharmaceutical composition of claim 19, wherein the mutant allele of IDH1 has a mutation selected from R132H, R132C, R132L, R132V, R132S and R132GF.

* * * * *